(12) United States Patent
Jardemark et al.

(10) Patent No.: US 8,232,074 B2
(45) Date of Patent: Jul. 31, 2012

(54) NANOELECTRODES AND NANOTIPS FOR RECORDING TRANSMEMBRANE CURRENTS IN A PLURALITY OF CELLS

(75) Inventors: Kent Jardemark, Gothenburg (SE);
Aldo Jesorka, Gothenburg (SE);
Mattias Karlsson, Gothenburg (SE);
Jessica Olofsson, Gothenburg (SE);
Owe Orwar, Hovas (SE); Johan Pihl, Gothenburg (SE); Eskil Sahlin, Gothenburg (SE)

(73) Assignee: Cellectricon AB, Gothenburg (SE)

( * ) Notice: Subject to any disclaimer, the term of this patent is extended or adjusted under 35 U.S.C. 154(b) by 1465 days.

(21) Appl. No.: 10/688,794

(22) Filed: Oct. 15, 2003

(65) Prior Publication Data
US 2004/0182707 A1 Sep. 23, 2004

Related U.S. Application Data

(60) Provisional application No. 60/418,702, filed on Oct. 16, 2002.

(51) Int. Cl.
*C12Q 1/02* (2006.01)
*C12N 13/00* (2006.01)
*C25B 9/08* (2006.01)
*G01N 27/26* (2006.01)

(52) U.S. Cl. ....... 435/29; 435/173.5; 977/703; 977/904; 204/451; 204/601

(58) Field of Classification Search .............. 435/29, 435/173.5; 204/451, 601; 977/703, 904
See application file for complete search history.

(56) References Cited

U.S. PATENT DOCUMENTS

| | | | |
|---|---|---|---|
| 3,449,938 A | 6/1969 | Giddings | |
| 3,503,712 A | 3/1970 | Sussman | |
| 3,538,744 A | 11/1970 | Karasek | |
| 3,565,537 A | 2/1971 | Fielding | |
| 3,690,836 A | 9/1972 | Buissiere | |

(Continued)

FOREIGN PATENT DOCUMENTS

DE 19936302 A1 2/2001

(Continued)

OTHER PUBLICATIONS

Hamill et al., "Improved patch-clamp techniques for high-resolution current recording from cells and cell-free membrane patches," Pflügers Archiv 391:85-100, 1981.*

(Continued)

*Primary Examiner* — Rosanne Kosson
(74) *Attorney, Agent, or Firm* — Edwards Wildman Palmer LLP; David G. Conlin; Andrew W. Shyjan, Esq.

(57) ABSTRACT

The present invention relates to methods of measuring electrical properties of a cell using electrode devices comprising tapered nanotips having submicrometer dimensions ("nanoelectrodes") for insertion into a cell. The devices are used to measure electrical properties of the cell and, optionally, may be used to electroporate, the cell or subcellular structures within the cell. The invention also provides arrays of electrode devices having nanotips for simultaneously or sequentially measuring the electrical properties of cells (e.g., such as surface immobilized cells). The electrodes can be used to measure properties of ion channels and in HTS assays to identify drugs which affect the properties of ion channels. The invention additionally provides microfluidic systems adapted for use with the electrode devices having nanotips. In combination with the electrodes, the microfluidic systems provide cell-based biosensors for monitoring cellular responses to conditions, such as exposure to candidate drugs.

17 Claims, 23 Drawing Sheets

U.S. PATENT DOCUMENTS

Figure 2A:
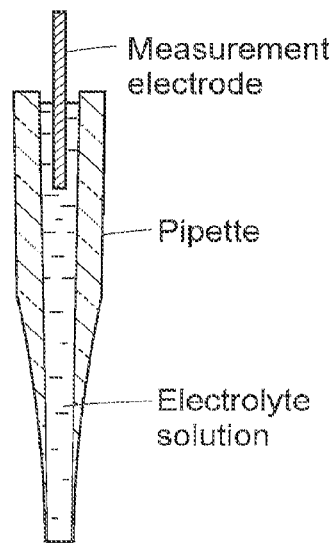

| | | | |
|---|---|---|---|
| 3,867,201 A | 2/1975 | Holmes | |
| 3,992,158 A | 11/1976 | Przybylowicz et al. | |
| 4,617,608 A | 10/1986 | Blonder et al. | |
| 4,900,663 A | 2/1990 | Wie et al. | |
| 4,935,040 A | 6/1990 | Goedert | |
| 5,078,164 A * | 1/1992 | Doellgast | 134/166 R |
| 5,116,495 A | 5/1992 | Prohaska | |
| 5,137,817 A | 8/1992 | Busta et al. | |
| 5,165,292 A | 11/1992 | Prohaska | |
| 5,208,145 A | 5/1993 | Rogers | |
| 5,376,252 A | 12/1994 | Ekstrom et al. | |
| 5,449,492 A | 9/1995 | Krishtal | |
| 5,501,662 A | 3/1996 | Hofmann | |
| 5,597,699 A | 1/1997 | Lanzara | |
| 5,800,690 A * | 9/1998 | Chow et al. | 204/451 |
| 6,123,819 A | 9/2000 | Peeters | 204/403 |
| 6,184,029 B1 | 2/2001 | Wilding et al. | |
| 6,193,647 B1 | 2/2001 | Beebe et al. | |
| 6,208,893 B1 | 3/2001 | Hofmann | |
| 6,241,666 B1 | 6/2001 | Pomeranz et al. | |
| 6,242,209 B1 | 6/2001 | Ransom et al. | |
| 6,278,895 B1 | 8/2001 | Bernard | |
| 6,294,063 B1 | 9/2001 | Becker et al. | |
| 6,326,177 B1 | 12/2001 | Schoenbach et al. | |
| 6,368,851 B1 | 4/2002 | Baumann et al. | |
| 6,455,303 B1 | 9/2002 | Orwar et al. | |
| 6,470,226 B1 | 10/2002 | Olesen et al. | |
| 6,521,430 B1 | 2/2003 | Orwar et al. | |
| 6,686,193 B2 | 2/2004 | Maher et al. | |
| 7,018,819 B2 | 3/2006 | Orwar et al. | |
| 7,109,034 B2 | 9/2006 | Orwar et al. | |
| 7,390,650 B2 | 6/2008 | Karlsson et al. | |
| 7,470,518 B2 | 12/2008 | Chiu et al. | |
| 7,563,614 B2 | 7/2009 | Orwar et al. | |
| 2001/0029320 A1 | 10/2001 | Trumbull et al. | |
| 2002/0025568 A1* | 2/2002 | Maher et al. | 435/173.6 |
| 2002/0063067 A1 | 5/2002 | Bech et al. | |
| 2002/0074227 A1 | 6/2002 | Nisch et al. | |
| 2002/0076689 A1 | 6/2002 | Farb et al. | |
| 2002/0083686 A1 | 7/2002 | Audino et al. | |
| 2002/0084410 A1* | 7/2002 | Colbert et al. | 250/306 |
| 2002/0146822 A1 | 10/2002 | Takayama et al. | |
| 2002/0182627 A1 | 12/2002 | Wang et al. | |
| 2003/0009112 A1 | 1/2003 | Hammerle et al. | |
| 2003/0014081 A1 | 1/2003 | Bernabei | |
| 2003/0022268 A1 | 1/2003 | Lepple-Wienhues | |
| 2003/0049862 A1* | 3/2003 | He et al. | 436/180 |
| 2003/0129581 A1 | 7/2003 | Owen et al. | |
| 2003/0153067 A1 | 8/2003 | Stett et al. | |
| 2004/0029101 A1 | 2/2004 | Orwar et al. | |
| 2004/0110307 A1 | 6/2004 | Karlsson et al. | |
| 2004/0112529 A1 | 6/2004 | Karlsson et al. | |
| 2004/0181343 A1 | 9/2004 | Wigstrom et al. | |
| 2004/0182707 A1 | 9/2004 | Jardemark et al. | |
| 2005/0009171 A1 | 1/2005 | Fertig et al. | |
| 2005/0026283 A1 | 2/2005 | Ormar et al. | |
| 2005/0048651 A1 | 3/2005 | Ryttsen et al. | |
| 2006/0078961 A1 | 4/2006 | Chiu et al. | |
| 2006/0223164 A1 | 10/2006 | Orwar et al. | |
| 2006/0234298 A1 | 10/2006 | Chiu et al. | |
| 2007/0155016 A1 | 7/2007 | Lee et al. | |
| 2007/0243523 A1 | 10/2007 | Ionescu-Zanetti et al. | |

FOREIGN PATENT DOCUMENTS

| | | |
|---|---|---|
| EP | 0010456 A1 | 4/1980 |
| EP | 0107631 A2 | 5/1984 |
| EP | 0347579 A2 | 12/1989 |
| EP | 376611 A2 | 7/1990 |
| EP | 0 986 758 A1 | 3/2000 |
| EP | 1145760 A2 | 10/2001 |
| FR | 1444146 A | 7/1966 |
| GB | 2 371 626 A | 7/2002 |
| WO | WO-90/04645 A1 | 5/1990 |
| WO | WO-94/20841 A1 | 9/1994 |
| WO | WO-95/23211 A1 | 8/1995 |
| WO | WO-96/00111 A1 | 1/1996 |
| WO | WO-96/10170 A1 | 4/1996 |
| WO | WO-96/13721 A1 | 5/1996 |
| WO | WO-97/05922 A2 | 2/1997 |
| WO | WO-98/00231 A1 | 1/1998 |
| WO | WO-98/55870 A1 | 12/1998 |
| WO | WO-99/24110 A1 | 5/1999 |
| WO | WO-99/24823 A1 | 5/1999 |
| WO | WO-99/66329 A1 | 12/1999 |
| WO | WO-00/20554 A1 | 4/2000 |
| WO | WO-00/34434 A1 | 6/2000 |
| WO | WO-00/34776 A1 | 6/2000 |
| WO | WO-00/62931 A1 | 10/2000 |
| WO | WO-01/09297 A1 | 2/2001 |
| WO | WO 01/18246 A1 | 3/2001 |
| WO | WO-01/25769 A2 | 4/2001 |
| WO | WO-01/43817 A1 | 6/2001 |
| WO | WO-01/48474 A1 | 7/2001 |
| WO | WO 01/59447 A1 | 8/2001 |
| WO | WO-01/94939 A1 | 12/2001 |
| WO | WO-02/03058 A2 | 1/2002 |
| WO | WO-02/04943 A2 | 1/2002 |
| WO | WO-02/10747 A2 | 2/2002 |
| WO | WO-02/24862 A2 | 3/2002 |
| WO | WO-02/33066 A1 | 4/2002 |
| WO | WO-02/065092 A2 | 8/2002 |
| WO | WO-02/066596 A2 | 8/2002 |
| WO | WO-03/013647 A2 | 2/2003 |
| WO | WO-03/046170 A1 | 6/2003 |
| WO | WO-03/046171 A1 | 6/2003 |
| WO | WO-03/068906 A1 | 8/2003 |
| WO | WO-03/089564 A1 | 10/2003 |
| WO | WO-2004/036202 A1 | 4/2004 |
| WO | WO-2004/039489 A2 | 5/2004 |
| WO | WO-2006/074350 A2 | 7/2006 |

OTHER PUBLICATIONS

International Search Report dated Mar. 10, 2004 for Application No. PCT/IB03/05044.

European Search Report in EP Application No. 03703801 dated Jun. 4, 2008.

European Search Report in EP Application No. 03751872 dated Nov. 2, 2005.

European Search Report in EP Application No. 06717606 dated Jun. 2, 2008.

European Search Report in EP Application No. 070043451 dated May 16, 2007.

European Search Report in EP Application No. 10014162 dated Aug. 16, 2011.

European Search Report in EP Application No. 10014163 dated Aug. 12, 2011.

European Search Report in EP Application No. 10014164 dated Aug. 16, 2011.

European Search Report in EP Application No. 79302339 dated Jan. 1, 1980.

Farre et al., "Screening of Ion Channel Receptor Agonists Using Capillary Electrophoresis-Patch Clamp Detection with Resensitized Detector Cells", Anal. Chem. 2001, 73, 1228-1233.

Fertig et al., "Whole Cell Patch Clamp Recording Performed on Plana Glass Chip", Biophysical Journal, vol. 82, Jun. 2002, 3056-3062.

Fishman et al., "Cell-to-Cell Scanning in Capillary Electrophoresis", Analytical Chemistry, vol. 68 No. 7, Apr. 1, 1996, 1181-1186.

Fishman et al., "Identification of receptor ligands and receptor subtypes using antagonists in a capillary electrophoresis single-cell biosensor separation system", Proc. Natl. Acad. Sci. USA, vol. 92, pp. 7877-7881, Aug. 1995.

Hamill et al., "Improved Patch-Clamp Techniques for High-Resolution Current Recording from Cells and Cell-Free Membrane Patches", Pflugers Archiv (1981) 391:85-100.

International Preliminary Examination Report dated Jul. 24, 1992.

International Preliminary Examination Report in PCT/US03/26125 dated Apr. 11, 2005.

International Preliminary Report on Patentability in PCT/IB06/04236 dated Apr. 28, 2009.

International Preliminary Report on Patentability in PCT/US06/000431 dated Aug. 7, 2007.
International Search Report in PCT/IB06/04236 dated Mar. 7, 2008.
International Search Report in PCT/SE91/00327 dated Jul. 30, 1991.
International Search Report in PCT/US03/01027 dated May 28, 2003.
International Search Report in PCT/US03/26125 dated Jan. 22, 2004.
International Search Report in PCT/US06/00431 dated Jul. 23, 2007.
Ionescu-Zanetti et al., "Mammalian electrophysiology on a microfluidic platform." Proc Natl Acad Sci U S A. Jun. 28, 2005;102(26):9112-7.
Jardemark et al., "Screening of Receptor Antagonists Using Agonist-Activated Patch Clamp Detection in Chemical Separations", Anal. Chem. 1998, 70, 2468-2474.
Klemic et al., "Micromolded PDMS planar electrode allows patch clamp electrical recordings from cells", Biosensors and Bioelectronics 17 (2002) 597-604.
McAllister et al.; "Microfabricated Microneedles for Gene and Drug Delivery"; Annu. Rev. Biomed. Eng.; 2000; 02; pp. 289-313.
Nolkrantz et al.; "Electroporation of Single Cells and tissues with an Electrolyte-filled Capillary"; Analytical Chemistry; vol. 73; No. 18; Sep. 15, 2001; pp. 4469-4477.
Orwar et al., "Patch-Clamp Detection of Neurotransmitters in Capillary Electrophoresis", Science, vol. 272, Jun. 21, 1996, 1779-1782.
Pihl et al., "Microfluidic gradient-generating device for pharmacological profiling." Analytical Chemistry Jul. 1, 2005, vol. 77, No. 13, pp. 3897-390.
Seo et al., "Integrated multiple patch-clamp array chip via lateral cell trapping junctions." Appl. Phys. Lett. 2004. 84, 1973-75.
Sinclair et al. "A Cell-Based Bar Code Reader for High-Throughput Screening of Ion Channel-Ligand Interactions", Anal. Chem. 2002, 74,6133-6138.
Stromberg et al., "Microfluidic Device for Combinatorial Fusion of Liposomes and Cells", Anal Chem. 2001, 73, 126-130.
Written Opinion in PCT/IB06/04236 dated Jul. 3, 2008.
Written Opinion in PCT/US06/000431 dated Jul. 23, 2007.

\* cited by examiner

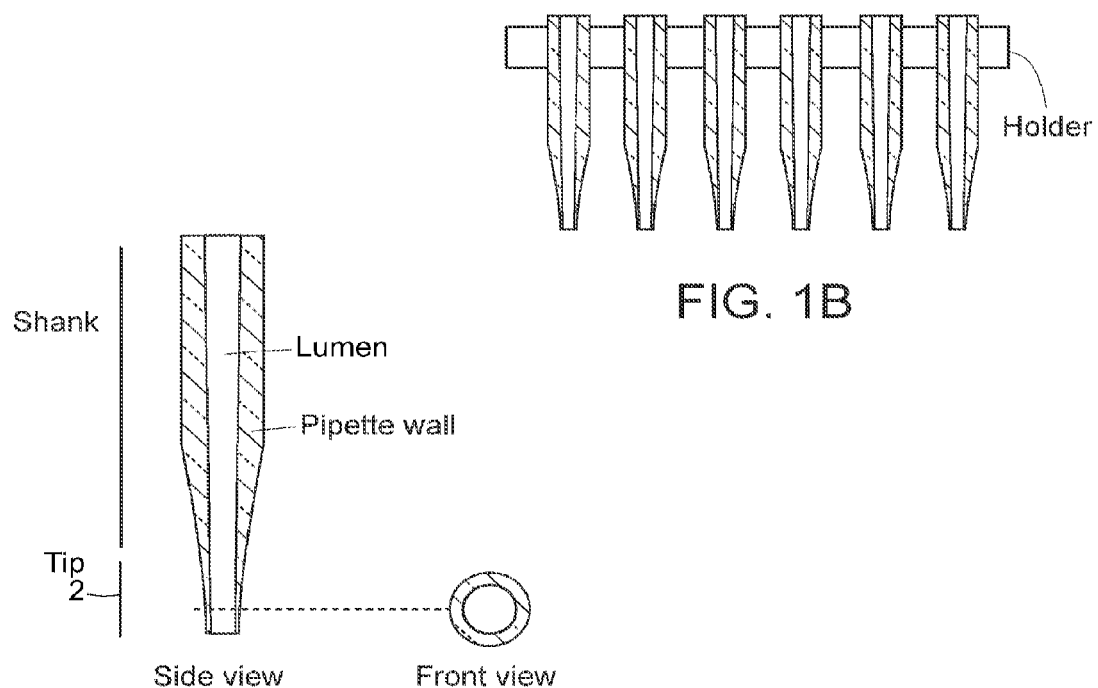
FIG. 1B
FIG. 1A
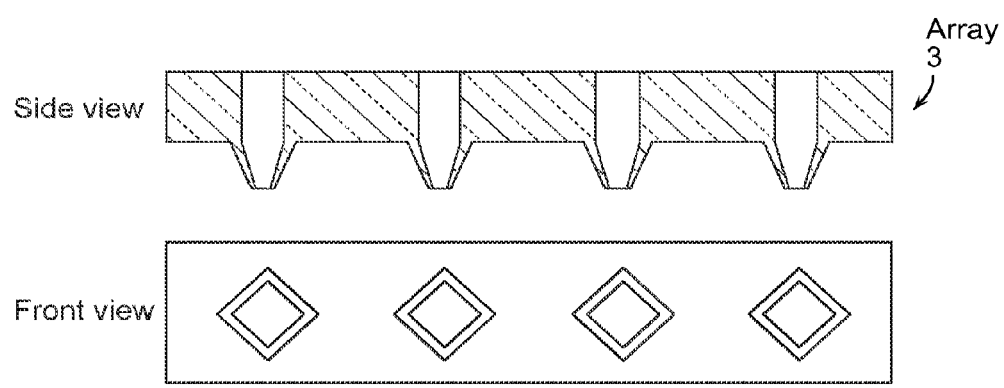
FIG. 1C

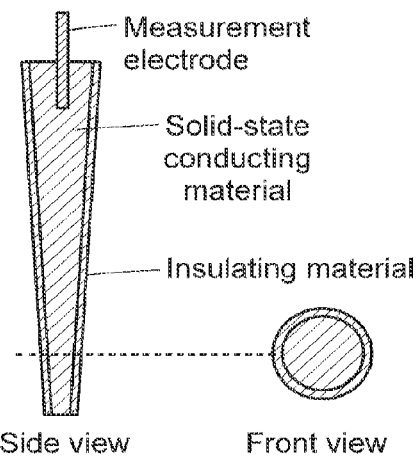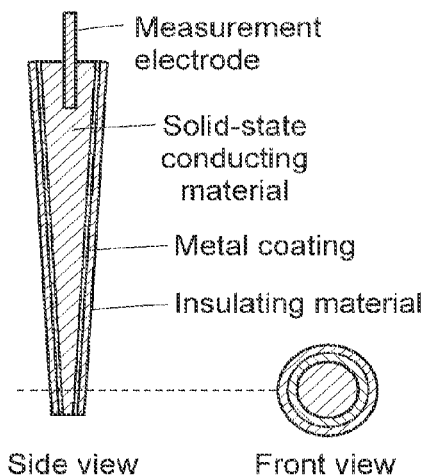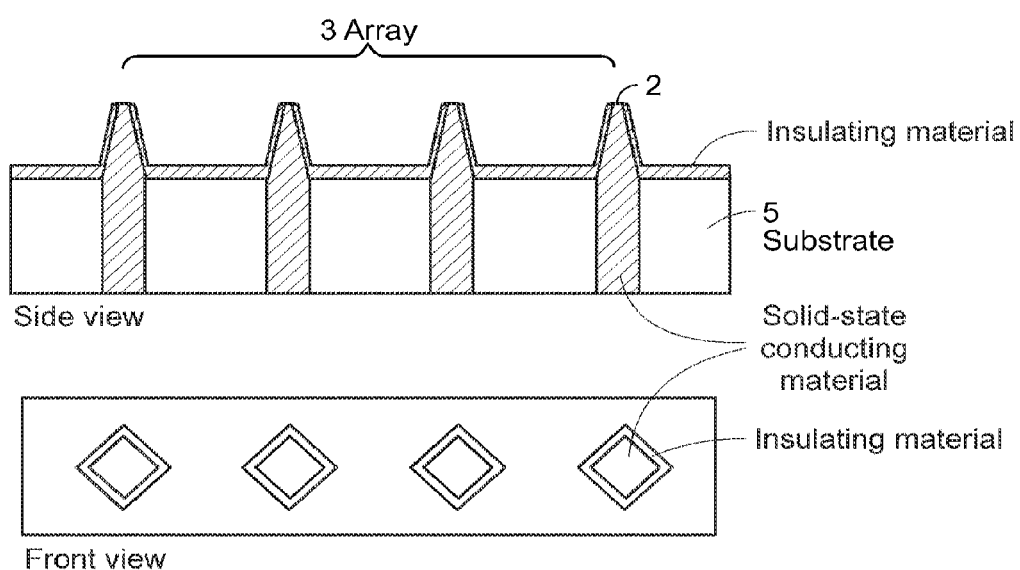

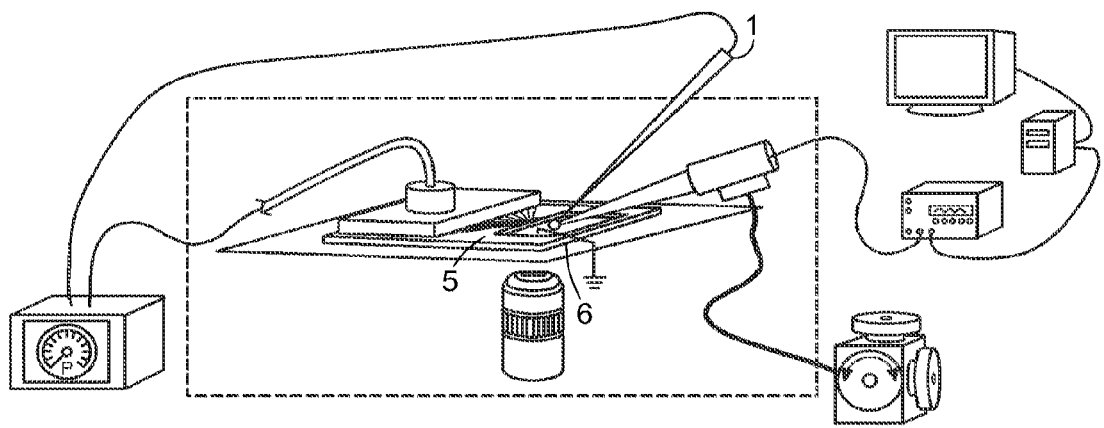
FIG. 11A
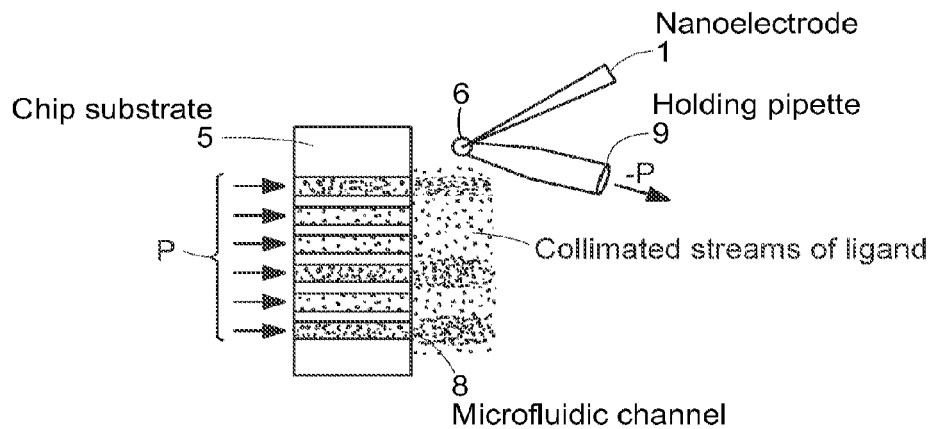
FIG. 11B
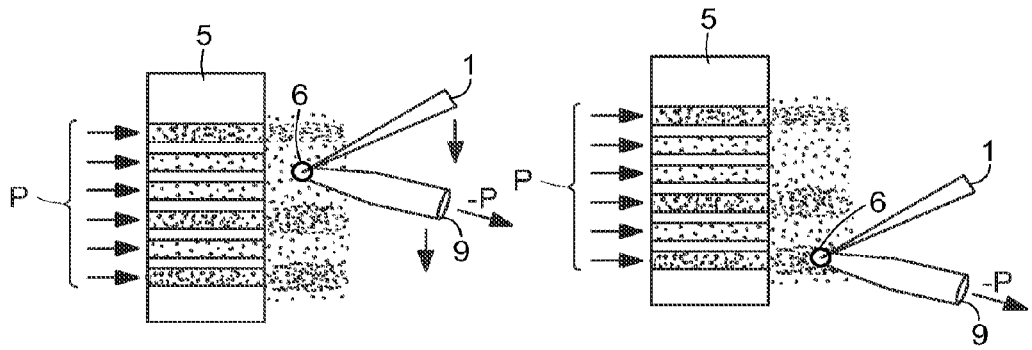
FIG. 11C
FIG. 11D

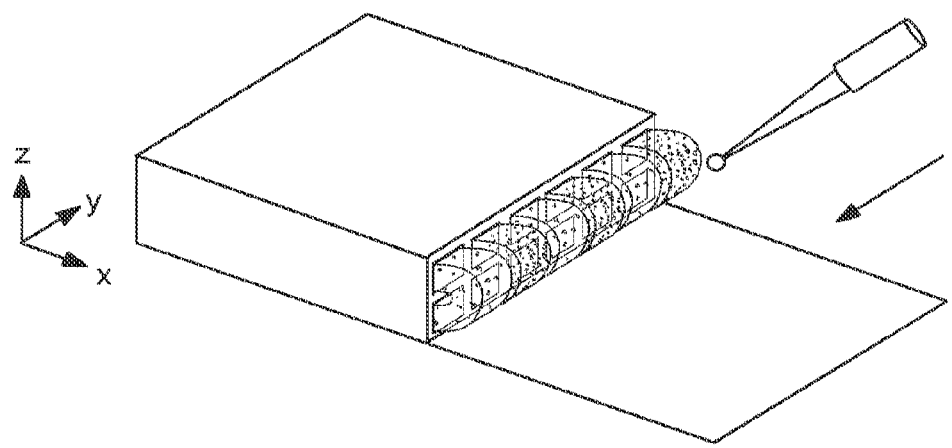
FIG. 15D
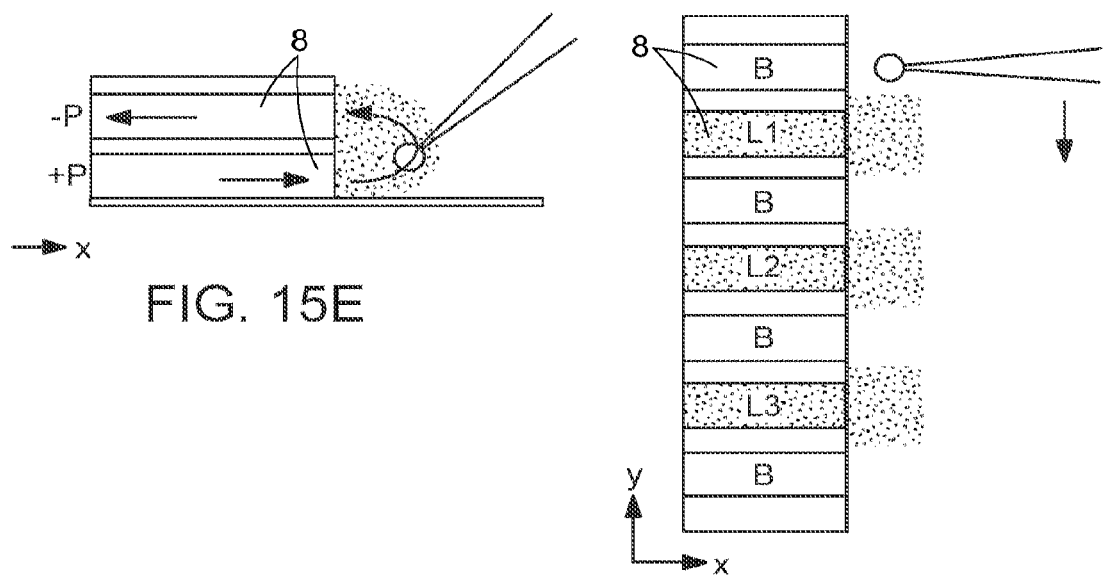
FIG. 15E
FIG. 15F

NANOELECTRODES AND NANOTIPS FOR RECORDING TRANSMEMBRANE CURRENTS IN A PLURALITY OF CELLS

RELATED APPLICATIONS

This application claims priority under 35 U.S.C. §119(e) to U.S. Provisional Application Ser. No. 60/418,702, filed Oct. 16, 2002, the entirety of which is incorporated by reference herein.

FIELD OF THE INVENTION

The invention provides systems and methods for recording transmembrane currents in a plurality of cells using nanoelectrodes. In particular, the invention relates to systems and methods for performing high-throughput electrophysiological recordings for drug discovery.

BACKGROUND OF THE INVENTION

Ion-channels are important therapeutic targets. Neuronal communication, heart function, and memory all critically rely upon the function of ligand-gated and voltage-gated ion-channels. In addition, a broad range of chronic and acute pathophysiological states in many organs such as the heart, gastrointestinal tract, and brain involve ion channels. Indeed, many existing drugs bind receptors directly or indirectly connected to ion-channels. For example, anti-psychotic drugs interact with receptors involved in dopaminergic, serotonergic, cholinergic, noradrenergic and glutamatergic neurotransmission.

Because of the importance of ion-channels as drug targets, there is a need for methods which enable high throughput screening (HTS) of compounds acting on ligand-gated and voltage-gated channels. However, existing HTS drug discovery systems targeting ion channels generally miss significant drug activity because they employ indirect methods, such as raw binding assays or fluorescence-based readouts. Although as many as ten thousand drug leads can be identified from a screen of a million compounds, identification of false positives and false negatives can still result in a potential highly therapeutic blockbuster drug being ignored, and in unnecessary and costly investments in false drug leads.

Patch clamp methods are superior to any other technology for measuring ion channel activity in cells, and can measure currents across cell membranes in ranges as low as picoAmps (see, e.g., Neher and Sakmann, *Nature* 260: 799-802; Hamill, et al., 1981, *Pflugers Arch* 391: 85-100; Sakmann and Neher, 1983, In *Single-Channel Recording* pp. 37-52, Eds. B. Sakmann and E. Neher. New York and London, Plenum Press).

Attempts have been made to use patch-clamp recordings in HTS platforms. For example, Sörensen et al., in WO 96/13721, describe a system that couples an HPLC autosampler to a micro-flow chamber in which a patch-clamped cell is placed. While the system enables multiple compounds to be assayed at a time, the system creates large dead volumes and solution exchange is generally slow compared to activation times of ion channel receptors.

Another strategy to develop patch-clamp-based HTS systems involves microfabrication of a plurality of patch-clamp-electrodes on solid supports using microfabrication techniques. Klemic, et al., in WO 01/59447, describe one such planar patch clamp electrode array comprising a plurality of electrodes for performing patch clamp recordings on a plurality of patch-clamped cells. Samples of cells and solutions are provided to the array by pouring, immersing the electrodes, or pipetting into wells containing the cells and electrodes. However, using such planar surfaces it has been difficult to obtain stable recording configurations for prolonged periods of time with good electrical properties.

In addition to difficulties observed in attempts to increase the throughput of patch clamp assays, the noise associated with recording electrodes is significant in most systems currently used and will often be the dominant source to the total noise in most electrophysiological measurements.

SUMMARY OF THE INVENTION

The invention provides systems and methods for increasing the throughput of electrophysiological measurements and for minimizing noise in measurements of the electrical properties of cells. The systems and methods described herein provide enhanced ability to measure fast responses, and minimize "space clamping" artefacts by introducing novel nanoelectrodes for use in ion channel recordings. Thus, the invention relates to improving the electrode interface between a cell and a recording amplifier where the electrode is being used to contact or penetrate a cell for registrations of electrical properties of said cell. Examples of such properties can be a change in currents through ion channels as a result of activation or deactivation of said ion channels e.g. in response to a chemical compound or a drug.

In one aspect, the invention provides an electrode device, comprising: a housing comprising walls defining a lumen and having a tip end and a seating end; a tip end for inserting into a cell; the seating end for receiving an electrode; wherein the lumen comprises an electrolyte solution, and wherein the tip end comprises a diffusion barrier for lowering the diffusion velocity of electrolytes in the electrolyte solution. The tip end may be less than than 1 μm in outer diameter. Suitable diffusion barriers include, but are not limited to, polyacryalamide, agar, PEDOT, an ion resin exchange medium, and an ion shuttle compound. An exemplary preferred ion resin exchange medium is Nafion®.

In one aspect, the electrode device comprises a housing comprising walls defining a lumen. The device has a tapered, or parallel, tip end and a seating end, the tip end for inserting into a cell, the seating end for receiving an electrode. The lumen comprises an electrically conducting polymer solution or a liquid state metal.

In another aspect, the electrode device comprises a housing comprising a seating end and a tip end and defining two, or more, lumens comprising parallel longitudinal axes. The tip end is preferably tapered for insertion into a cell and the seating end comprises two, or more, electrodes, one in each lumen.

In a further aspect, the invention provides a composite electrode comprising a housing comprising a tapered tip end for insertion into a cell and defining a lumen for contacting the cell with an electrolyte solution. The housing comprises a first and second layer of conducting material, separated from each other by an insulating layer. Preferably, the tapered tip end is less than about 1 μm in diameter.

In one preferred aspect, at least a cell-contacting surface of the electrode device is hydrophobic.

In another preferred aspect, at least a cell-contacting surface of the electrode device is hydrophilic.

In a further aspect, the invention provides solid electrically conducting nanoelectrodes. Preferably, such electrodes further comprise an electrically insulating layer. The solid conducting part can comprise a polymer, a metal, a carbon fiber, or a carbon nanotube. The electrically insulating layer can comprise a thin film of polymer or a glass housing. Preferably, the tapered tip end is less than about 5 µm in diameter and more preferably, is less than about 1 µm in diameter.

The nanoelectrodes can be injected into cells using stab-injection protocols. Preferably, the nanoelectrode tips are injected into cells by electroinjection protocols as described in M. Karlsson et al., "Electroinjection of biopolymers and colloids into single unilamellar liposomes." *Anal. Chem.* 72:5857-5862, 2000.

The invention further provides a method for measuring an electrical property of a cell comprising bringing an electrode device as described above into proximity with the cell, inserting or injecting at least the tip of the device into the cell, and recording electrical properties of the cell with the electrode device. In one preferred aspect, the cell comprises an ion channel and the electrical properties measured provide an indication of the activity of the ion channel. When dual electrodes or composite electrodes are used it is possible to exploit the different functionalities of each electrode during a single injection protocol. For example, electroporation and recording may be performed after a single injection of the electrode device.

The invention also provides nanoelectrode arrays comprising a plurality of electrodes devices as described above. Electrode devices may be of the same type or of different types to provide different functionalities in the array.

The invention additionally provides a substrate comprising a substantially planar solid material, wherein the material comprises a plurality of apertures and wherein the rims of the apertures are raised relative to the substantially planar solid material, and form an electrically conducting nanotip for inserting into or impaling a cell. Preferably, the conducting material is coated with an insulating material except at the tip of each aperture. In one aspect, the aperture comprises a lumen for receiving a conducting medium. The conducting medium can comprise, for example, an electrolyte solution, an electrically conducting polymer, a solid state metal, a carbon fiber, carbon nanotube, or a liquid state metal.

In another aspect, the substrate comprises a plurality of wells, each well comprising one of the apertures forming a nanotip.

In a further aspect, a substrate or plate is provided which comprises a plurality of solid electrode tips protruding from the plate. The tips may be hollow or solid (e.g., in the form of pins, or cylinders, which may have flat or tapered (e.g., pointed) ends for insertion into a cell).

In one aspect, at least one of the cell-contacting surfaces of the electrode devices in the array is hydrophobic. In another aspect, at least the tip of each aperture is hydrophobic.

In another aspect, at least one of the cell-contacting surfaces of the electrode devices in the array is hydrophilic. In another aspect, at least the tip of each aperture is hydrophilic.

The invention further provides a microfluidic system comprising a substrate, wherein the substrate comprises at least one measurement chamber comprising a substantially planar solid conducting material, wherein the conducting material comprises a plurality of raised apertures, each aperture comprising a nanotip for inserting into a cell, and wherein the substrate further comprises at least one microchannel with an outlet which opens into the measurement chamber.

In one aspect, the measurement chamber is circular and a plurality of microchannels are radially disposed about the chamber and comprise outlets that open into the chamber.

In another aspect, the invention provides a microfluidic system comprising a substrate, the substrate comprising at least one measurement chamber and at least one microchannel with an outlet which opens into the chamber. Preferably, the system comprises at least one electrode device as described above. In one aspect, the electrode device is an integral part of the microfluidic system, e.g., the microfluidic substrate includes one or more nanotips. In another aspect, the system comprises a plate comprising at least one nanotip, in which the at least one nanotip is fabricated to correspond in orientation and placement to at least one measurement chamber in a microfluidic substrate such that positioning the plate of tip(s) in proximity to the microfluidic substrate, positions the tip(s) in proximity to a cell or cell structure in the measurement chamber(s). For example, when used in conjunction with a plate comprising a plurality of nanotips, the center-to-center distance of the nanotips may correspond to the center-to-center distance of measurement chambers in a microfluidic substrate. In these embodiments, the microfluidic substrate may or may not itself comprise one or more nanotips. The plate electrode tips may be solid or hollow and may be single or composite electrode tips.

The system may further comprise a pressure control device for controlling positive and negative pressure applied to at least one microchannel. The system may be interfaced to an industry standard microtiter plate through one or more external tubings or capillaries which may additionally comprise one or more external valves to control fluid flow through the tubings or capillaries. In one aspect, the chamber is for measuring properties of a cell, such as the physiological responses of the cell to a fluid stream comprising an agent (e.g., a ligand, an agonist, an antagonist, a drug, a potential toxin, and the like).

Preferably, the system further comprises a scanning mechanism for scanning one or more of the substrate or the electrode device inserted into cell in an x-, y-, and/or z-direction. In one aspect, the system comprises a processor in communication with the scanning mechanism which controls one or more of: the rate of scanning, the direction of scanning, acceleration of scanning, and number of scans. Preferably, the processor provides instructions to the scanning mechanism in response to signals from the detector. The system may further comprise an amplifier in communication with the at least one electrode device for detecting changes in electrical properties of one or more cells.

Preferably, the system also comprises a user device in communication with the processor which comprises a graphical user display for interfacing with a user.

Also preferably, the substrate comprises a plurality of microchannels which deliver a plurality of substantially separate aqueous streams into the measurement chamber. In one aspect, the substrate comprises a plurality of alternating buffer delivery and agonist delivery channels, each channel comprising an outlet for delivering a substantially separate aqueous stream into the chamber. In another aspect, the system comprises a scanning mechanism for scanning a sensor (e.g., such as a cell) across the aqueous streams from the channels.

In one aspect, the invention provides a system comprising one or more nanoelectrodes and a cell chamber for receiving one or more cells. Preferably, the system comprises a positioner for positioning the one or more nanoelectrodes in proximity to the one or more cells and for inserting the one or more nanoelectrodes into the cells. In one aspect, the cells are stationary (e.g., held within wells, orifices or pores in the cell chamber or within holding pipettes), or incorporated in brain slices, cell cultures, or organotypic cultures, and the nanoelectrode(s) are moved relative to the cells. In another aspect, the nanoelectrode(s) are stationary (e.g., part of a substrate which forms the cell chamber) and the cells are bought into proximity to the nanoelectrodes (e.g., via movable holding pipettes).

The systems according to the invention is anticipated to provide close to 100% success rates in obtaining good recording configurations compared to traditional patch clamp methods or chip-based patch clamp methods (i.e., low noise in combination with small RC time constants, high success rates of seal formation, etc). Further, recordings are stable over extremely long periods of time. The nanoelectrode systems are small scale and compatible with microfluidic systems. The systems also permit spatial and temporal control of both recording as well as electrical, mechanical, optical or chemical stimulation of cells in a cell culture because large numbers of nanoelectrodes can be inserted into the cells or in close proximity to cells.

In one aspect, the invention provides a method for measuring an electrical property of a cell. The method comprises inserting a nanoelectrode into a cell membrane and recording electrical properties of the cell such as a transmembrane current and/or voltage or the capacitance of a cell. The method provides for stable and high signal-to-noise ratio recording of transmembrane currents and voltages as well as membrane capacitance. The method comprises means for simultaneous measurement of electrical properties of a plurality of cells, where the cells also can be incorporated in a cellular network.

In one aspect, the invention provides a system comprising a substrate containing a plurality of measurement chambers (e.g. greater than 10 and preferably 96, 384 or 1536 number of chambers) for containing one or more cells and for measuring electrical properties of one or more cells. Preferably, the center-to-center distance of each chamber corresponds to the center-to-center distance of wells in an industry standard microtiter or multi-well plate. In another aspect the substrate is comprised of industry standard microtiter or multi-well plates. The system also comprises at least one nanoelectrode, allowing the measurement of the electrical properties of the cell(s). Preferrably, one- or two-dimensional arrays of electrodes are used. Most preferably two-dimensional arrays of electrodes containing at least the number of electrodes corresponding to the number of measurement chambers in the substrate are used. In a further aspect, the one or more nanoelectrodes comprised within the system can be moved by the use of a micropositioner in an x-, y-, and/or z-direction to bring the nanoelectrode(s) into proximity to a cell within the measurement chamber. Alternatively, or additionally, the nanoelectrode(s) may be part of the measurement chamber, e.g., fabricated on the base of the measurement chamber. In this arrangement, each measurement chamber prefferably contains at least one nanoelectrode. In one aspect, this system is used for high throughput electrophysiological analysis of ion channel-drug candidate interactions. To perform such HTS assays, drug solutions needs to be dispensed into each recording well. For example, in a 96 well format where at least one cell in each well is contacted by a nanoelectrode it might be desirable to administer a different drug to each of the 96 wells. Drugs can be dispensed or pipetted into said wells using pipetting and dispenser techniques known in the art. Alternatively, drugs can be administered to e.g. 96 different wells using microfluidic means. For example, an industry-standard 96 well plate can be modified to contain microfluidic channels that transport drug solutions to said wells in a controllable fashion.

The invention additionally provides microfluidic systems and methods for rapid, programmable, and sequential delivery of aqueous streams to one or more cells. The system comprises one or more nanoelectrodes which can be placed in proximity to the one or more cells for insertion into the cell(s). The nanoelectrodes are used to measure electrical properties of the cell(s). In one aspect, the systems are used for high throughput electropysiological analysis of ion channel-drug candidate interactions.

In one aspect, the invention provides microfluidic systems for altering the solution environment around a cell or portion of a cell, and methods for using the same. In contrast to prior art microfluidic systems, the time interval between sample plug deliveries is minimized, e.g., on the order of microseconds and seconds, permitting rapid analysis of compounds (e.g., such as drugs or small molecules).

In one aspect, the invention provides a system comprising a substrate for changing the solution environment around a cell or portion of a cell. The substrate comprises a measurement chamber for containing one or more cells and for measuring electrical properties of the one or more cells. Preferably, the substrate further comprises a plurality of channels. Each channel comprises an outlet for delivering a substantially separate aqueous stream into the chamber. In one aspect, the outlets are substantially parallel, i.e., arrayed linearly in a single plane. The dimensions of the outlets can vary; however, the diameter of a plurality of outlets is, preferably, at least about the diameter of a cell. Preferably, a plurality, if not all, of the microchannels, sequentially and programmably delivers a fluid stream into the chamber.

In a preferred aspect, each channel of the substrate comprises at least one inlet for receiving solution from a reservoir, conforming in geometry and placement on the substrate to the geometry and placement of wells in a multi-well plate. For example, the substrate can comprise 96-1536 reservoirs, each connected to an independent channel on the substrate. Preferably, the center-to-center distance of each reservoir corresponds to the center-to-center distance of wells in an industry standard microtiter or multi-well plate.

In a further aspect, the substrate comprises one or more treatment chambers or microchambers for delivering a treatment to a cell placed within the treatment chamber. The treatment can comprise exposing the cell to a chemical or compound, (e.g. drugs or dyes, such as calcium ion chelating fluorogenic dyes), exposing the cell to an electrical current (e.g., electroporation, electrofusion, and the like), or exposing the cell to light (e.g., exposure to a particular wavelength of light). A treatment chamber can be used for multiple types of treatments that may be delivered sequentially or simultaneously. For example, an electrically treated cell also can be exposed to a chemical or compound and/or exposed to light. Treatment can be continuous over a period of time or intermittent (e.g., spaced over regular or irregular intervals). The cell treatment chamber can comprise a channel with an outlet for delivering a treated cell to the measurement chamber or directly to a micropositioner for positioning the cell within the chamber.

Preferably, the base of the cell measurement chamber is optically transmissive and in one aspect, the system further comprises a light source (e.g., such as a laser) in optical communication with the chamber. The light source can be used to continuously or intermittently expose a cell to light of the same or different wavelengths. The measurement chamber and/or channels additionally can be equipped with control devices. For example, the measurement chamber and/or channels can comprise temperature sensors, pH sensors, pressure sensors and the like, for providing signals relating to chamber and/or channel conditions to a system processor.

The measurement chamber can be adapted for receiving one or more cells. In one aspect, the measurement chamber comprises one or more cells in suspension. In another aspect, the measurement chamber comprises at least one adherent cell(s) associated with the base and or a wall of the chamber, or a brain slice, a cell culture, or a organotypic culture. A cell may be stably associated with a location of the measurement chamber. For example, the measurement chamber can comprise one or more compartments, such as wells, orifices or pores, which receive a cell and which prevent a cell from moving any substantial distance (e.g., more than twice the diameter the cell) within the compartment. In one aspect, one or more cell holders (e.g., such as capillaries or micropipettes) are in proximity to the cell measurement chamber and a cell is held in a relatively stationary position with the cell measurement chamber. Alternatively, the cell can be held in position using focused electrical or magnetic fields. A cell holder may comprise an opening that is about the diameter of a cell (e.g., from about 5 μm to about 500 μm, and preferably about 10 μm). By containing at least a portion of the cell in the opening, e.g., maintaining a loose seal between the cell and the opening, the cell is maintained in a relatively stationary position relative to a nanoelectrode. In addtion, cells, or at least a portion of a cell, can be held at a desired coordinate by the use of optical trapping techniques, by the use of electrical fields (e.g. dielectrophoresis) or by the use of hydrodynamic focusing.

The cell or cell membrane fraction within the measurement chamber can comprise an ion channel, including, but not limited to, a presynaptically-expressed ion channel, a postsynaptically-expressed ion channel, a ligand-gated receptor/ion-channel complex, a voltage-gated channel, and the like. In a further aspect, the cell comprises a receptor, such as a G-Protein-Coupled Receptor (GPCR), or an orphan receptor for which no ligand is known, or a receptor comprising a known ligand.

A cultured cell can be used and can be selected from the group consisting of CHO cells, NIH-3T3 cells, and HEK-293 cells. The cell can be recombinantly engineered to express a sensing molecule such as an ion channel or receptor. Many other different cell types also can be used, for example, mammalian cells (e.g., including, but not limited to human cells, primate cells, bovine cells, swine cells, other domestic animals, and the like); bacterial cells; protist cells; yeast cells; plant cells; invertebrate cells, including insect cells; amphibian cells; avian cells; fish cells; and the like. The cell can also be included in a brain slice from a rat, a normal mouse, or a mutant (knockout) mouse, as well as it can be included in a cell culture or in a organotypic culture.

A portion of a cell such as a cell membrane fraction can be placed within the measurement chamber. Cell membrane fractions can be isolated from any of the cells described above, or can be generated by aggregating a liposome or other lipid-based particle with a sensing molecule, such as an ion channel or receptor, using methods routine in the art.

The cell or portion of the cell can be positioned in the chamber using a holding pipette or a capillary coupled to a micropositioner or by other means as discussed above. In one aspect, the cell holder is used to both position a cell in proximity to a nanoelectrode and to maintain the cell in a relatively stationary position within the cell measurement chamber once it is positioned. In addition, a cell, or at least a portion of a cell, can be held at a desired coordinate by the use of optical trapping techniques, by the use of electrical fields (e.g. dielectrophoresis) or by the use of hydrodynamic focusing. In one aspect, the one or more nanoelectrodes comprised within the system can be moved in an x-, y-, and/or z-direction to bring the nanoelectrode(s) into proximity to a cell within the measurement chamber. The cell may be held relatively stationary within a cell holder (e.g., capillary, micropipette) or within a compartment (e.g., well, orifice, pore) at the base of the measurement chamber. Alternatively, or additionally, the nanoelectrode may be part of the measurement chamber, e.g., fabricated on the base of the measurement chamber.

Any of the nanoelectrodes described above may be used in the system. Preferably, the surface chemistry and/or surface geometry of the nanoelectrode are optimized as described above to provide a high electrical resistance seal between the nanoelectrode and the cell. More preferably, an array of nanoelectrodes is provided. The array may be moveable as a unit in x-, y-, z-directions or individual nanoelectrodes in the array may move independently. However, in one aspect the array is fixed and fabricated on the base of the measurement chamber. In one preferred aspect, a plurality of cells are arrayed on a substrate and an array of electrode devices are positioned in register with the cells. The electrode devices can be inserted into the plurality of cells in a single parallel experiment. Alternatively, a plurality of cells can be arrayed on a substrate and impaled on a plurality of nanoelectrodes fabricated on the substrate.

In another aspect, the system comprises a substrate that comprises at least one measurement chamber, a plurality of channels, and at least one cell treatment chamber. Preferably, each channel comprises an outlet for delivering a fluid stream into the chamber, and the cell treatment chamber is adapted for delivering an electrical current to a cell placed within the cell treatment chamber. In one aspect, the cell treatment chamber further comprises a channel with an outlet for delivering a cell to the measurement chamber. The system can be used to rapidly, sequentially, and programmably change the solution environment e.g. to provide different drugs around a cell that has been electroporated and/or electrofused, long-term challenged with a drug and/or otherwise treated within the cell treatment chamber. Alternatively, or additionally, the measurement chamber also can be used as a treatment chamber and in one aspect, the measurement chamber is in electrical communication with one or more electrodes for continuously or intermittently exposing a cell to an electric field.

In one aspect, a system according to the invention further comprises a scanning mechanism for changing the position of a cell relative to the outlets of the microchannels. The scanning mechanism can translate the substrate containing the microchannel outlets relative to a stationary cell, or can translate the cell relative to a stationary substrate, or can move both cell and substrate at varying rates and directions relative to each other. In one aspect, the cell is positioned relative to an outlet using a micropositioner which is coupled to a micromanipulator. Thus, the micromanipulator and micropositioner can be used to move the cell across a plurality of fluid streams exiting the outlets of the channels. Alternatively, or additionally, producing pressure drops sequentially across adjacent microchannels also can regulate scanning.

Preferably, the scanning mechanism is in communication with a processor and translation occurs in response to instructions from the processor (e.g., programmed instructions or instructions generated as a result of a feedback signal (e.g., from an amplifier and the like)). In one aspect, the processor controls one or more of: the rate of scanning, the direction of scanning, acceleration of scanning, and number of scans. For example, the system can be used to move cells in the chamber to user-selected, or system-selected coordinates, for specified (e.g., programmable) lengths of time. Preferably, the system processor also can be used to locate the position of one or more cells in the chamber, e.g., in response to previous scanning actions and/or in response to optical signals from the cells detected by the system detector. In one aspect, the system further comprises a user device in communication with the processor which comprises a graphical user display for interfacing with a user. For example, the display can be used to display coordinates of object(s) within the chamber, or optical data or other data obtained from the chamber.

The invention additionally provides a substrate comprising a measurement chamber for receiving one or more cells which comprise a receptor or ion channel. In one aspect, the system sequentially exposes one or more cells for short periods of time to one or several ligands that bind to the receptor/ion channel and to buffer without ligand for short periods of time. For example, sequential exposure of a cell to these different solution conditions for short periods of time can be achieved by pipetting or by scanning the cell across interdigitated channels that alternate delivery of one or several ligands and buffer. The flow of buffer and sample solution is preferably a steady state flow at constant velocity.

However, in another aspect, the system delivers pulses (e.g., pulsatile on/off flow) of buffer to a receptor/ion channel through a superfusion capillary positioned in proximity to both the cell and to an outlet through which a fluid is streaming. For example, the system can comprise a micropositioner for positioning a cell in proximity to the outlet and a capillary comprising an outlet in sufficient proximity to the micropositioner to deliver a buffer from the capillary to the cell. A scanning mechanism can be used to move both the capillary and cell simultaneously, to maintain the appropriate proximity of the capillary to the cell. The capillary also can be coupled to a pumping mechanism to provide pulsatile delivery of buffer to the cell. In another aspect, the flow rate of buffer from the one or more superfusion capillaries in proximity to one or more cells can be higher or lower than the flow rate of fluid from the channels.

The invention further provides a substrate that comprises a circular measurement chamber for receiving one or more cells, comprising a cylindrical wall and a base. In one aspect, the substrate comprises a plurality of channels comprising outlets whose openings are radially disposed about the circumference of the wall of the chamber (e.g., in a spokes-wheel configuration), for delivering fluid streams into the chamber. Preferably, the substrate also comprises at least one output channel for draining waste from the chamber. In one aspect, at least one additional channel delivers buffer to the chamber. Preferably, the angle between the at least one additional channel for delivering buffer and the output channel is greater than 10°. More preferably, the angle is greater than 90°. The channel "spokes" may all lie in the same plane, or at least two of the spokes may lie in different planes.

Rapid, programmed exchange of solutions in the chamber is used to alter the solution environment, e.g., change of solutions containing different drugs around one or more cells placed in the measurement chamber and multiple output channels can be provided in this configuration. For example, there may be an output channel for each channel for delivering sample/buffer. The number of channels for delivering also can be varied, e.g., to render the substrate suitable for interfacing with an industry standard microtiter plate. For example, there may be 96 to 1536 channels for delivering samples. In another aspect, there may be an additional, equal number of channels for delivering buffer (e.g., to provide interdigitating fluid streams of sample and buffer).

The invention also provides a multi-layered substrate for changing the solution environment around one or more cells, comprising: a first substrate comprising channels for delivering fluid to the one or more cells, a filter layer for retaining one or more cells which are in proximity to the first substrate; and a second substrate comprising a waste reservoir for receiving fluid from the filter layer. One or more cells can be provided between the first substrate and the filter layer. Preferably, the system further comprises a mechanism for creating a pressure differential between the first and second substrate to force fluid flowing from channels in the first substrate through the filter and into the waste reservoir, i.e., providing rapid fluid exchange through the filter (i.e., cell) layer.

The invention additionally provides a substrate that comprises a measurement chamber for receiving one or more cells, a first channel comprising an outlet intersecting with the chamber, and a plurality of sample delivery channels intersecting with the first channel. The first channel also is connected to a buffer reservoir (e.g., through a connecting channel). In one aspect, the longitudinal axes of the sample delivery channels are parallel with respect to each other, but are angled with respect to the longitudinal axis of the first channel (e.g., providing a "fish bone" shape). Rapid flow of solution through the first channel and/or sample channels can be achieved through a positive pressure mechanism in communication with the buffer reservoir and/or sample channels. Passive one-way valves can be provided at the junction between sample delivery channels and the first channel to further regulate flow rates. In one aspect, at least one of the sample reservoirs is sealed by a septum that can comprise a needle or tube inserted therein.

The invention further provides a substrate that comprises a chamber for receiving a cell, a plurality of delivery channels comprising outlets for feeding sample or buffer into the chamber, and a plurality of drain channels comprising inlets opposite the outlets of the delivery channels. The longitudinal axes of the delivery channels can be in the same, or a different plane, from the longitudinal axes of the drain channels. In one aspect, the plurality of drain channels is on top of the plurality of inlet channels (i.e., the substrate is three-dimensional).

Any of the systems described above can further comprise a pressure control device for controlling positive and negative pressure applied to at least one microchannel of the substrate. In systems where substrates comprise both delivery channels as well as output channel(s), the system preferably further comprises a mechanism for applying a positive pressure to at least one delivery channel while applying a negative pressure to at least one output channel. Preferably, hydrostatic pressure at at least one of the channels can be changed in response to a feedback signal received by the processor. In addition, fluid can also be delivered or withdrawn from the channels to the chamber by a number of different methods, including by electrophoresis and/or by electroosmosis and/or by pumping.

The system can thus regulate when, and through which channel, a fluid stream is delivered or withdrawn from the measurement chamber. For example, after a defined period of time, a fluid stream can be withdrawn from the chamber through the same channel through which it entered the system or through a different channel. When a drain channel is adjacent to a delivery channel, the system can generate a U-shaped fluid stream that can efficiently recycle compounds delivered through delivery channels.

As described above, multiple delivery channel configurations can be provided: straight, angled, branched, fish-bone shaped, and the like. In one aspect, each delivery channel comprises one or more intersecting channels whose longitudinal axes are perpendicular to the longitudinal axis of the delivery channels. In another aspect, each delivery channel comprises one or more intersecting channels whose longitudinal axes are at an angle with respect to the delivery channel.

In general, any of the channel configurations described above are interfaceable with containers for delivering samples to the reservoirs or sample inlets (e.g., through capillaries or tubings connecting the containers with the reservoirs/inlets). In one aspect, at least one channel is branched, comprising multiple inlets. Preferably, the multiple inlets interface with a single container. However, multiple inlets also may interface with several different containers.

Further, any of the substrates described above can be interfaced to a multi-well plate (e.g., a microtiter plate) through one or more external tubings or capillaries. The one or more tubings or capillaries can comprise one or more external valves to control fluid flow through the tubings or capillaries. In one aspect, a plurality of the wells of the multi-well plates comprises known solutions. The system also can be interfaced with a plurality of microtiter plates; e.g., the plates can be stacked, one on top of the other. Preferably, the system further comprises a micropump for pumping fluids from the wells of a microtiter plate or other suitable container(s) into the reservoirs of the substrate. More preferably, the system programmably delivers fluids to selected channels of the substrate through the reservoirs.

In one aspect, the longitudinal axes of the channels are substantially parallel. The channels can be arranged in a linear array, in a two-dimensional array, or in a three-dimensional array, can comprise treatment chambers, measurement chambers, reservoirs, and/or waste channels, and can be interfaced with container(s) or multi-well plate(s) as described above. In one aspect, output channels can overlay input channels (i.e., in a three-dimensional configuration). Preferably, the longitudinal axis of at least one output or drain channel is parallel, but lying in a different plane, relative to the longitudinal axis of at least one input channel. By applying a positive pressure to an input channel at the same time that a negative pressure is applied to an adjacent output or drain channel, a U-shaped fluid stream can be generated within the chamber. In this way, a nanoelectrode impaled cell within the chamber can be exposed to a compound in a fluid stream from an inlet channel which can, for example, be recycled by being withdrawn from the chamber through the adjacent output or drain channel. The U-shaped fluid streams can, preferably, be used to create local well-defined regions of fluid streams with specific composition in a large-volume reservoir or open volume.

Preferably, the cell is scanned sequentially across the at least two aqueous fluid streams, thereby altering the aqueous solution environment around the object. Scanning can be performed by moving the substrate and/or the object, or, can be mediated by pressure drops applied to the channels.

The measurement chamber can comprise a plurality of nanoelectrode-impaled cells; preferably, each cell is scanned across at least two streams. Scanning can be performed by a scanning mechanism controlled by a processor as described above. The chamber can, additionally have inlets and outlets for adding and withdrawing of solution. For example, fresh buffer solution can be added to the recording chamber by using a peristaltic pump. Each cell is also momentarily perfused by buffer from a pipet positioned in the vicinity of: the somata of cell, the dendrites of a cell, or the axon of a cell.

Cells may be exposed to a fluid stream during or prior to a recording event and the electrical properties of the cell in response to this exposing can be determined. In one aspect, a cell is exposed to a candidate modulator of ion channel activity. By providing an array of cells which can be exposed to different doses of an agent, a dose-response curve can be determined for any candidate modulator.

The nanoelectrodes may also be used to electroporate cells, e.g., to introduce a cell-impermeable molecules into the cells. Preferably, an electrical property of the cell is measured after introduction of the molecule into the cell. In one aspect, the cell impermeable molecule is a pharmaceutical agent, a marker or a dye.

In one aspect, the method further comprises modifying one or more scanning parameters, such as the rate of scanning, the direction of scanning, acceleration of scanning, and number of scans. Scanning parameters can be modified in response to a feedback signal, such as a signal relating to the response of an object to one or more of aqueous streams. Scanning also can be coordinated with other system operations. For example, scanning can be coordinated with exposure of a cell to an electrical current, i.e., inducing pore formation in a cell membrane, as the cell is scanned past one or more sample outlets.

Hydrostatic pressure at one or more channels also can be varied by the processor according to programmed instructions and/or in response to a feedback signal. In one aspect, hydrostatic pressure at each of the plurality of channels is different.

In another aspect, the viscosity of fluids in at least two of the channels is different. In yet another aspect, fluid within at least two of the channels is at a different temperature. In a further aspect, the osmolarity of fluid within at least two of the channels is different. In a still further aspect, the ionic strength of fluid within at least two of the channels is different. Fluid in at least one of the channels also can comprise an organic solvent. By changing these parameters at different outlets, cellular responses can be optimized to maximize sensitivity of detection and minimize background. In some aspects, parameters also can be varied to optimize certain cell treatments being provided (e.g., such as electroporation or electrofusion).

The invention also provides a method for rapidly changing the solution environment around a nanoscopic or microscopic object which comprises rapidly exchanging fluid in a measurement chamber comprising the nanoscopic or microscopic object. In one aspect, fluid exchange in the chamber occurs within less than about 1 minute, preferably, with less than about 30 seconds, less than about 20 seconds, less than about 10 seconds, less than about 5 seconds, or less than about 1 second. In another aspect, fluid exchange occurs within milliseconds. In another aspect fluid exchange occurs within nanoseconds.

In one aspect, the method comprises providing a measurement chamber comprising one or more cells wherein the chamber comprises a plurality of inlet channels for delivering a fluid into the chamber and a plurality of outlet channels for draining fluid from the chamber. Preferably, the longitudinal axes of the drain channels are at an angle with respect to the longitudinal axes of the delivery channels. In one aspect, the longitudinal axis of at least one drain channel is $\geq 90°$ with respect to the longitudinal axis of a delivery channel. Preferably, the angle is about 180°. Fluid entering the chamber is withdrawn from the chamber after a predetermined period of time or in response to a feedback signal. By controlling the velocity of fluid flow through the inlet channels and the output or drain channels, complete exchange of fluid in the chamber can occur in less than about 30 seconds, and preferably, in milliseconds.

Preferably, the velocity of fluids in the channels at an angle with respect to each other is different. In one aspect, the hydrostatic pressure of fluids in the channels at an angle with respect to each other is different. In another aspect, the viscosity of fluids in the channels at an angle with respect to each other is different. In still another aspect, the osmolarity of fluids in the channels at an angle with respect to each other is different. In a further aspect, the ionic strength of fluids in the channels at an angle with respect to each other is different. In yet a further aspect, the channels at an angle with respect to each other comprise different organic solvents.

The chamber can be circular, comprising a cylindrical wall and a base and the outlets can be radially disposed around the circumference of the wall, i.e., in a two-dimensional or three-dimensional spokes-wheel configuration. Other configurations are also possible. For example, each delivery channel can comprise an intersecting inlet channel whose longitudinal axis is perpendicular to the delivery channel.

The method can generally be used to measure responses of a cell or portion thereof to a condition in an aqueous environment by providing a cell or portion thereof in the measurement chamber of any of the substrates described above, exposing the cell or portion thereof to one or more aqueous streams for creating the condition, and detecting and/or measuring the response of the cell or portion thereof to the condition. For example, the condition may be a chemical or a compound to which the cell or portion thereof is exposed and/or can be the osmolarity and/or ionic strength and/or temperature and/or viscosity of a solution in which the cell or portion thereof is bathed.

The composition of the bulk solution in the measurement chamber in any of the substrates described above can be controlled, e.g., to vary the ionic composition of the measurement chamber or to provide chemicals or compounds to the solution. For example, by providing a superfusion system in proximity to the measurement chamber, a chemical or a compound, such as a drug, can be added to the measurement chamber during the course of an assay.

In one aspect, exposure of the cell or portion thereof to the condition occurs in the measurement chamber. However, alternatively, or additionally, exposure of the cell or portion thereof to the condition can occur in a treatment chamber which connects to the measurement chamber via one or more channels. The cell or portion thereof can be transferred to the measurement chamber in order to, by a nanoelectrode, measure a response induced by changing the conditions around the cell.

In another aspect, the invention also provides a method for generating a constantly or periodically activated ion channel in order to detect or screen for antagonists. The method comprises delivering a constant stream of an agonist to one or more cells in a cell measurement chamber through a plurality of microchannels feeding into the measurement chamber (e.g., using any of the substrates described above). Preferably, the one or more cells expresses receptor/ion channel complexes which do not desensitize, which desensitize very slowly, or whose desensitization properties are inhibited. Exposure of the one or more cells to the agonist produces a measurable response, such that the modulator is activated each time it passes a microchannel delivering agonist. Preferably, a plurality of the agonist delivering microchannels also comprise antagonist whose presence can be detected with a decrease in the measurable response (e.g., antagonism) when the cell passes by these microchannels. In one aspect, a plurality of microchannels comprise equal amounts of agonist but different concentrations of antagonist. Inhibition of the measurable response can thus be correlated with the presence of a particular dose of antagonist. In another aspect, a plurality of microchannels comprise equal amounts of agonist, but one or more, and preferably all of the plurality of microchannels, comprises different kinds of antagonists. In this way the properties and potencies of particular types of antagonists (or compounds suspected of being antagonists) can be studied.

In one aspect, a periodically resensitized receptor is provided using the superfusion system described above to deliver pulses of buffer to one or more cells in the measurement chamber, to thereby remove any bound agonist or modulator desensitizing the receptor, before the receptor is exposed to the next channel outlet containing agonists or receptor modulators. In detection of antagonists, the pulsated superfusion system can also periodically remove the constantly applied agonist. A transient peak response (which is desensitized to a steady state response) is generated when the resensitized cell is exposed to the agonist. The generation of this peak response can provide a better signal-to-noise ratio in detection of antagonists.

In another aspect, ion-channels in a cell are continuously activated or periodically activated by changing the potential across the cell-membrane. This provides a sensor for detection of compounds or drugs modulating voltage-dependent ion-channels.

Agonist, antagonist-, or modulator-induced changes of the following parameters or cell properties can be measured using nanoelectrode-impaled or nanoelectrode-contacted cells: cell surface area, cell membrane stretching, ion-channel permeability, release of internal vesicles from a cell, retrieval of vesicles from a cell membrane, levels of intracellular calcium, ion-channel-induced electrical properties (e.g., current, voltage, membrane capacitance, and the like), optical properties, viability (cytotoxicity), or modulation of intracellular cascade processes.

The systems and methods according to the invention can be used to perform high throughput screening for ion channel ligands and for drugs or ligands which act directly or indirectly on ion channels. However, more generally, the systems and methods can be used to screen for compounds/conditions which affect any extracellular, intracellular, or membrane-bound target(s). Thus, the systems and methods can be used to characterize, for example, the effects of drugs on cells. Examples of data that can be obtained for such purposes according to the present invention includes but is not limited to: dose response curves, $IC_{50}$ and $EC_{50}$ values, voltage-current curves, on/off rates, kinetic information, thermodynamic information, etc. Thus, the system can, for example, be used to characterize if an ion channel or receptor antagonists is a competitive or non-competitive inhibitor, or whether the antagonist binds to the receptor in a reversible or irreversible manner.

BRIEF DESCRIPTIONS OF THE DRAWINGS

The objects and features of the invention can be better understood with reference to the following detailed description and accompanying drawings.

FIGS. 1A-C are schematics showing nanotips for intracellular recordings according to one aspect of the invention. FIG. 1A shows an example of hollow nanotip 2 formed from a pulled capillary. FIG. 1B shows an array of pulled capillaries mounted together using a holder. FIG. 1C shows one-dimensional array 3 of microfabricated nanotips.

Figure 2B:
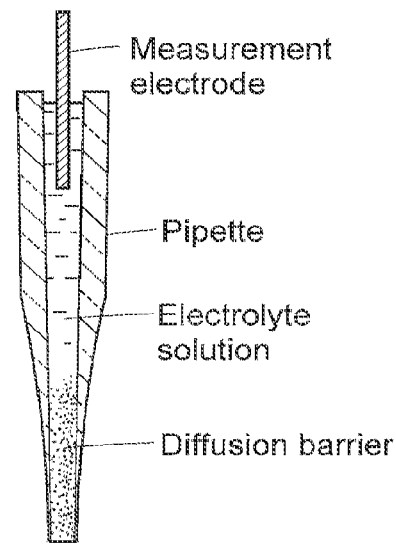
Figure 2C:
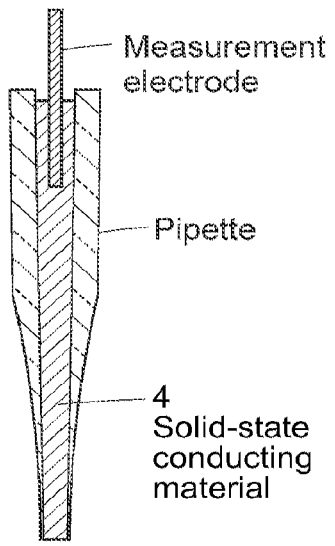
Figure 2D:
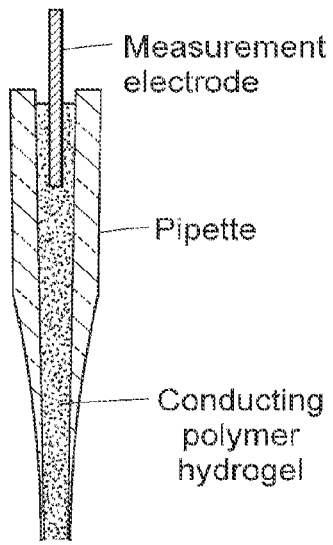

FIGS. 2A-D show nanotip-based electrode systems according to another aspect of the invention. FIG. 2A shows a nanotip filled with an electrolyte solution. The electrolyte solution is in contact with a working electrode. FIG. 2B shows a nanotip filled with an electrolyte solution and a diffusion-barrier mounted in the tip. FIG. 2C shows a nanotip filled with solid-state conducting material 4, such as a metal, a carbon fiber or a solidified conducting polymer. FIG. 2D shows a nanotip filled with a conducting polymer hydrogel.

FIGS. 3A-C illustrate conducting solid-state material based nanoelectrodes according to a further aspect of the invention. FIG. 3A shows an example of a carbon fibre electrode coated with an insulating material to reduce measurement noise. The apex of the nanotip is uncoated in order to ensure electrical contact. FIG. 3B shows a silver-coated carbon-fibre nanoelectrode. FIG. 3C shows an example of microfabricated array solid-state nanoelectrodes. FIG. 3C shows array 3 of capillaries mounted together, nanotips 2 and substrate 5.

Figure 4A:
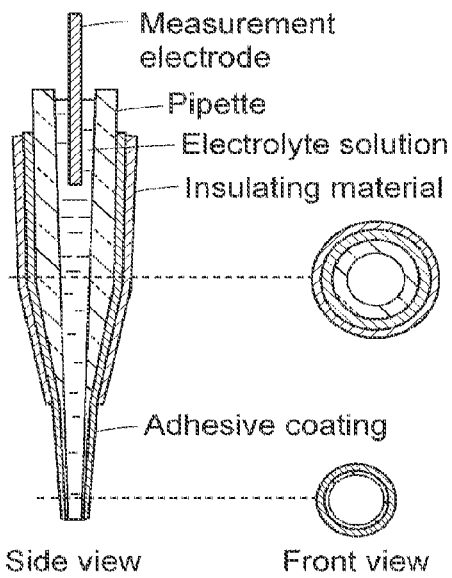
Figure 4B:
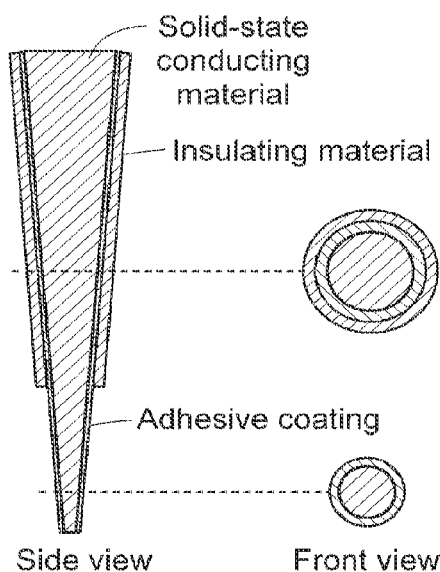
Figure 4C:
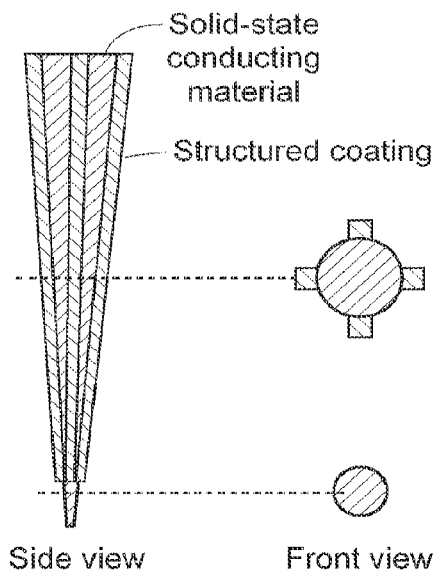

FIGS. 4A-C show differentially coated nanoelectrodes. FIG. 4A shows a nanoelectrode system that is differentially coated to improve the signal-to-noise ratio of electrophysiological registrations. The shanks of the pulled capillaries or tubing constituting the nanotips are coated with an insulating hydrophobic material in order to minimize the capacitance while the apical end of the nanoelectrode is coated with a material that promotes cell-membrane adhesion. FIG. 4B shows a differentially coated solid nanoelectrode. FIG. 4C shows a solid nanoelectrode layered with a structured coating. This coating is applied in order to increase the stiffness, mechanical stability, and durability of the electrode.

Figure 5A:
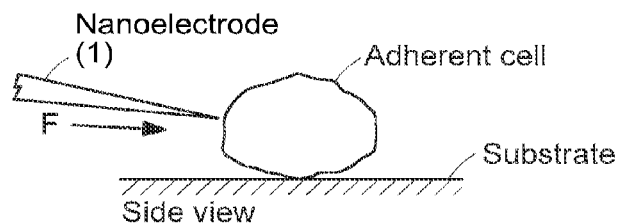
Figure 5B:
Figure 5C:
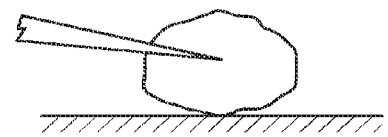
Figure 5D:
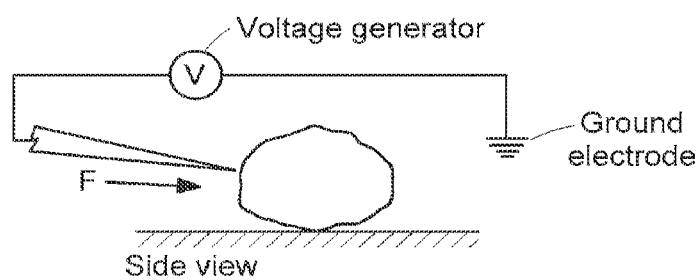
Figure 5E:
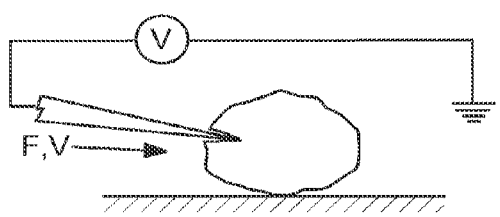
Figure 5F:
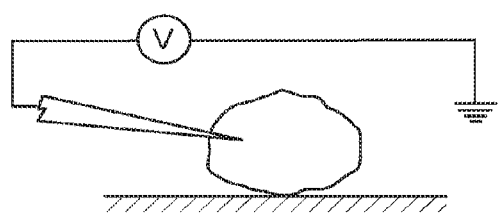

FIGS. 5A-F show methods of using nanoelectrodes according to one aspect of the invention. Nanoelectrode 1 may be inserted into cells using a stab-injection protocol as illustrated in FIGS. 5A-C. Here, only mechanical force (F) is used to break the cellular membrane. FIGS. 5D-F show use of a micro-electroinjection protocol to insert the nanoelectrodes. Here, a combination of mechanical force and electrical voltage pulses (V) are used to promote breakdown of cellular membranes facilitating nanoelectrode insertion.

Figure 6:
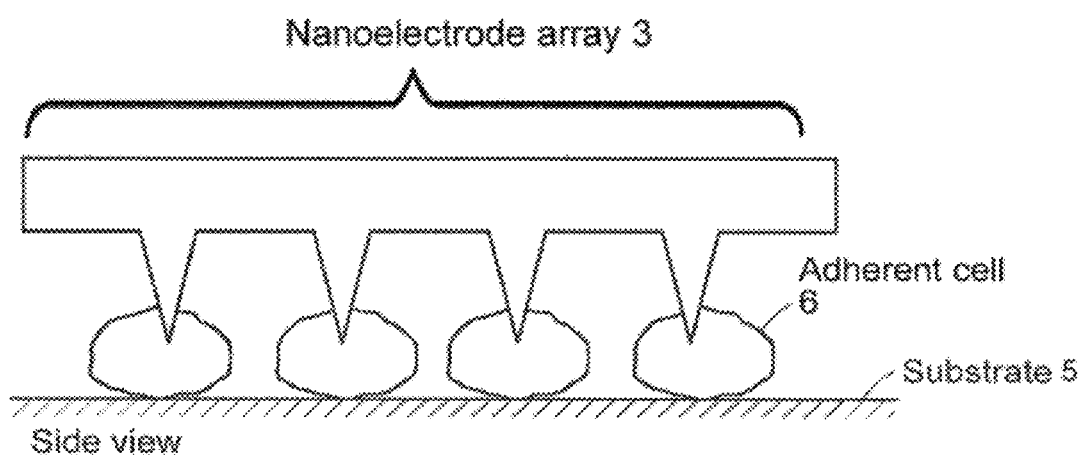

FIG. 6 illustrates parallel registration of electrical properties in a plurality of adherent cells 6 using a plurality of nanoelectrodes. Array 3 of nanoelectrodes is shown.

Figure 7A:
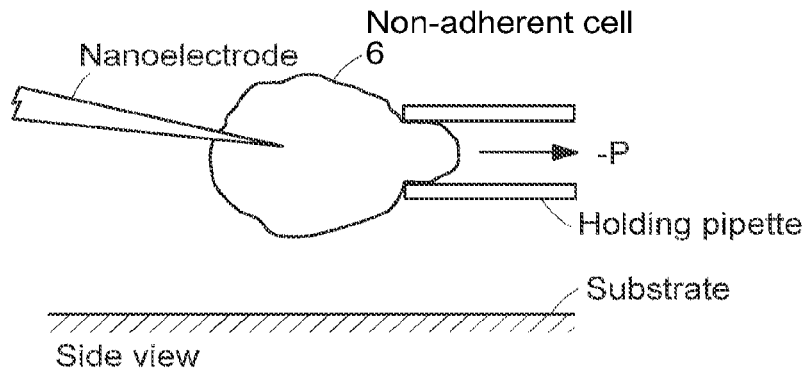
Figure 7B:
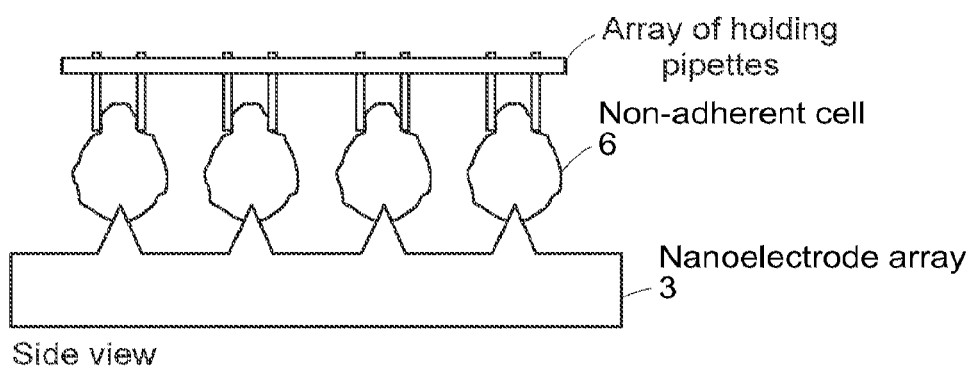
Figure 7C:
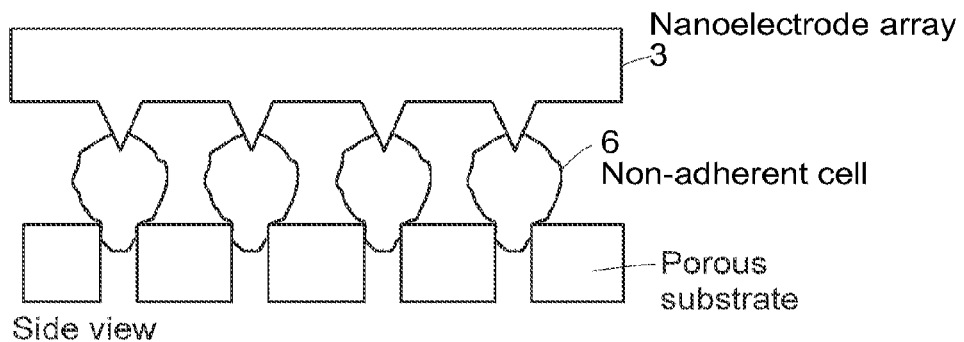

FIGS. 7A-C show the insertion of nanoelectrodes into cells grown in suspension. In one aspect, cells are held in place with holding capillaries through the application of a negative pressure on the holding pipette. FIG. 7A shows nanoelectrode insertion into cell 6 in suspension that is held in place using a holding pipette. FIG. 7B shows an array of holding pipettes for positioning cells 6 in register with array 3 of nanoelectrodes on a substrate. FIG. 7C shows the use of a porous substrate to maintain cells 6 in a relatively stationary position for insertion of array 3 of nanoelectrodes.

Figure 8A:
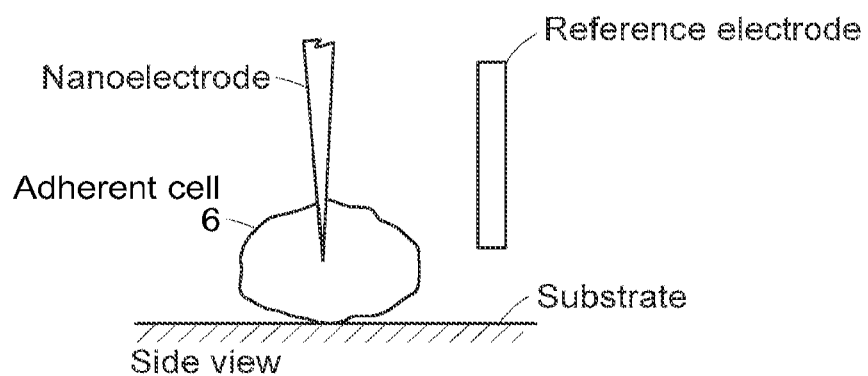
Figure 8B:
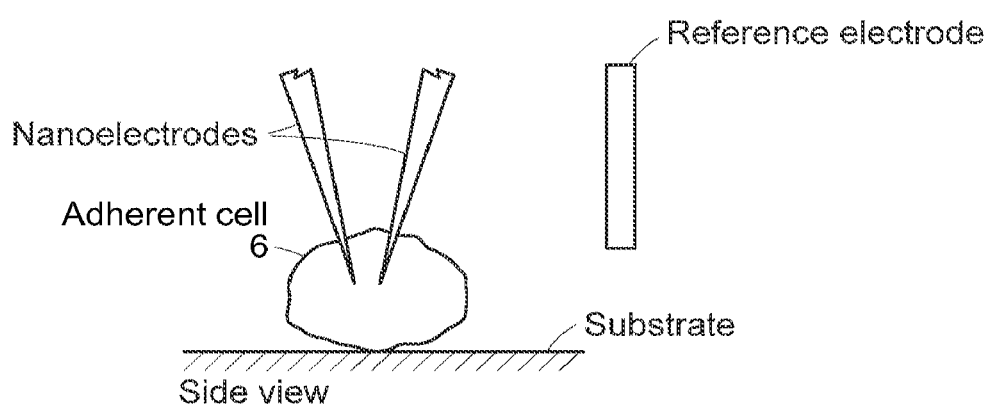

FIGS. 8A-B show different modes of electrophysiological registration. In FIG. 8A, one nanoelectrode is inserted into cell 6 while another electrode is placed outside the cell and is used as a reference electrode. FIG. 8B shows a three-electrode set-up comprising one external reference electrode and two measurement electrodes inserted into cell 6.

Figure 9A:
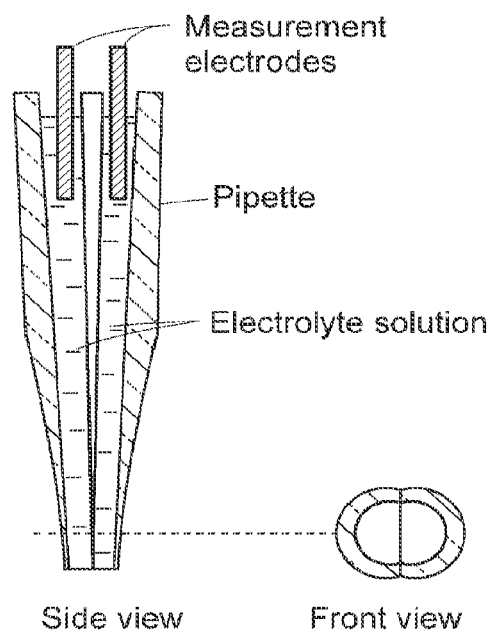
Figure 9B:
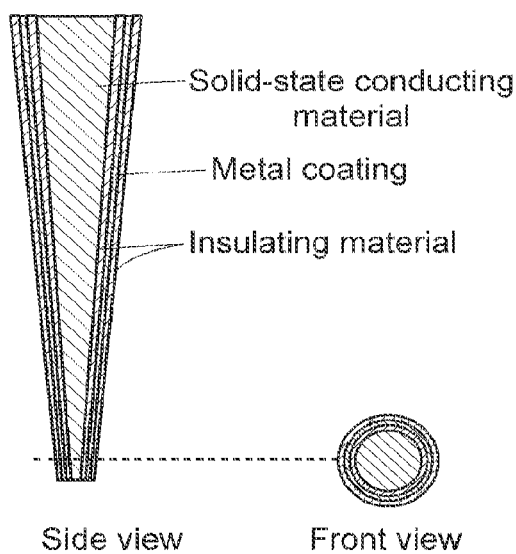

FIGS. 9A and 9B show dual barrel and sandwich nanoelectrodes, respectively. These arrangements integrate two measurement electrodes into a single unit. In FIG. 9A a dual barrel nanoelectrode is shown. In FIG. 9B, a multi-layered carbon fiber nanoelectrode is provided which is coated with an insulating layer, a metal layer and a second insulating layer. Here the carbon fiber itself constitutes one nanoelectrode and the metal layer provides the second measurement electrode.

Figures 10A, 10B:
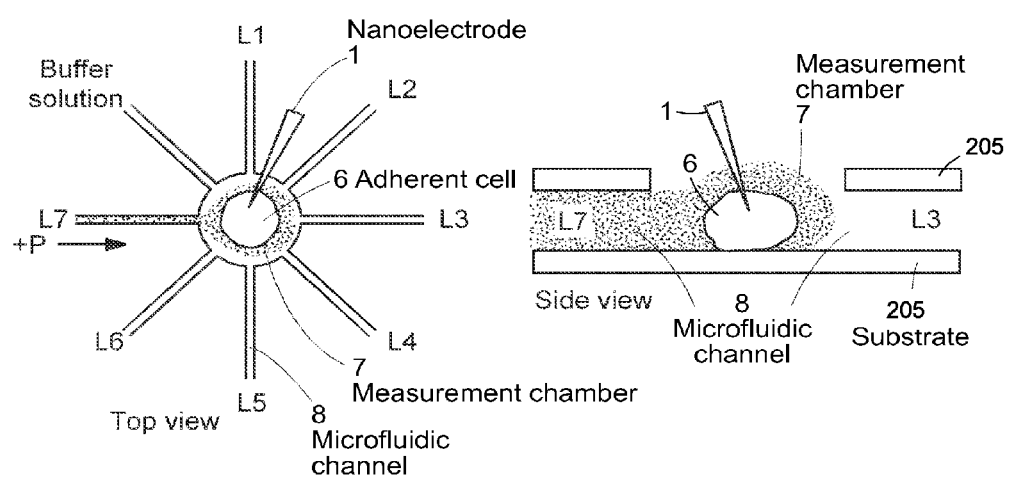
Figures 10C, 10D:
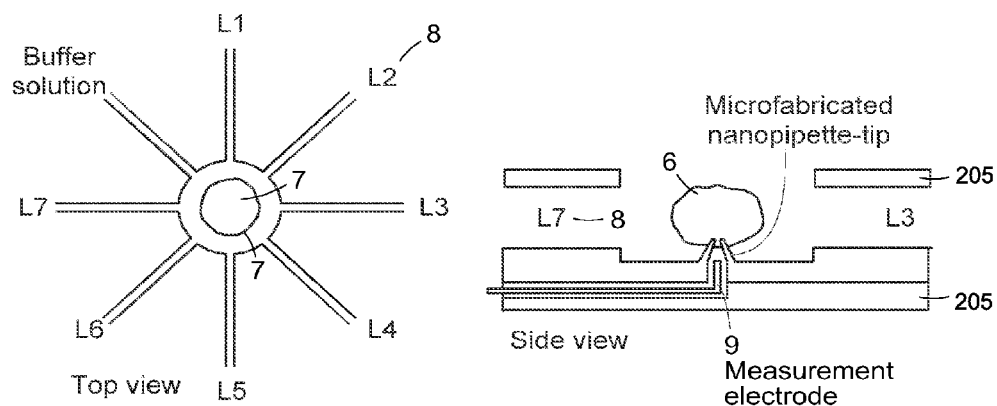

FIGS. 10A-D illustrate nanoelectrodes that are coupled to microfluidic devices. FIGS. 10A and 10B show top and side views, respectively, of a microfluidic chip having a "spokes wheel" design. As can be seen in FIG. 10A, the chip comprises a substrate with a plurality of microfluidic channels 8 whose inlets are radially disposed about the circumference of a measurement chamber 7 which contains a nanoelectrode 1-impaled or nanoelectrode 1-contacted cell 6. Solution through the channels can be regulated (e.g., by pressure and/or voltage differentials) to provide for sequential delivery of drug candidates into the measurement chamber. In order to register the action of the drug candidates on the cell, a nanoelectode is inserted into the cell to measure changes in its electrical properties. FIG. 10B shows an enlarged view of the measurement chamber 7 and the insertion of a nanoelectrode 1 into the cell 6 as it is exposed to solution flow from a microchannel 8 L7. Substrate (205) is shown. FIGS. 10C-D show top and side views, respectively, of a chip-based nano-electrode having a similar spokes wheel design. In this embodiment, the nanoelectrode is part of the chip itself (see, FIG. 10D).

FIGS. 11A-D illustrate a system for scanning a cell impaled with a nanoelectrode across multiple collimated streams containing drug candidates. As shown in FIG. 11A, substrate 305 comprising a plurality of channels 8 which feed into a cell chamber is placed in proximity to nanoelectrode 1 and holding pipette 9. Proper positioning of a cell by holding pipette 9 and/or insertion of nanoelectrode 1 into cell 6 can be visualized by making the cell chamber at least partially optically transparent so that light absorbed and/or transmitted by the cell can be measured. Nanoelectrode 1 is used to measure the electrical properties of cell 6 as it is scanned across microchannel inlets that open into the cell chamber (see, e.g., as show in FIGS. 11B-D).

Figure 12A:
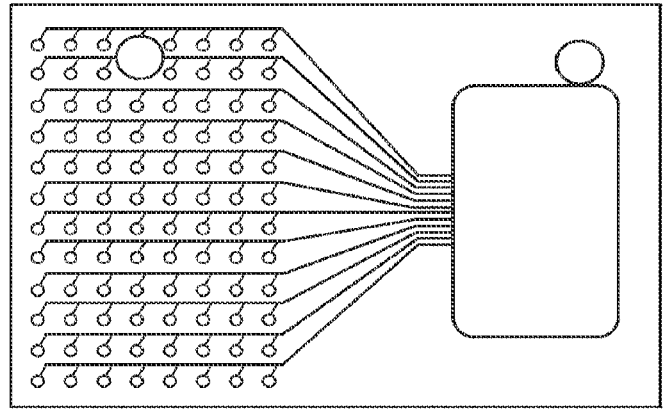
Figure 12B:
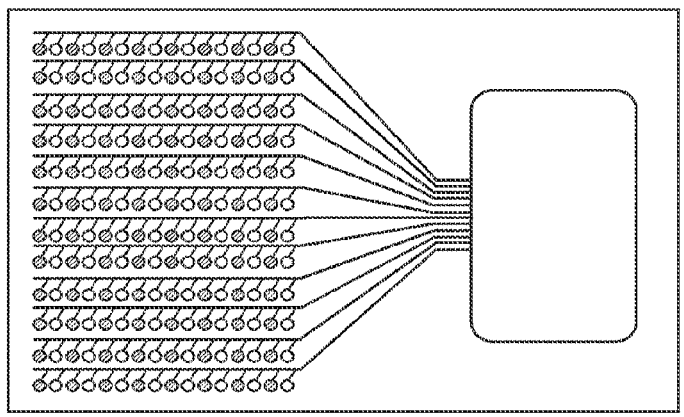
Figure 12C:
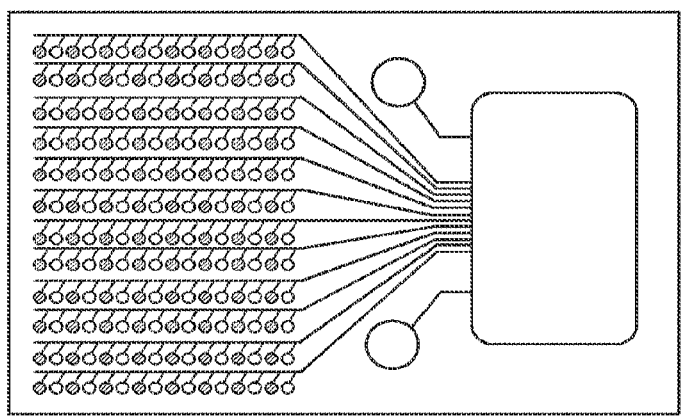

FIGS. 12A-C show top views of different embodiments of microfluidic chips according to aspects of the invention illustrating exemplary placements of reservoirs for interfacing with 96-well plates. FIG. 12A shows a chip comprising ligand reservoirs (e.g., the reservoirs receive samples of ligands from a 96-well plate). FIG. 12B shows a chip comprising alternating or interdigitating ligand and buffer reservoirs (e.g., every other reservoir receives samples of ligands from one 96-well plate, while the remaining reservoirs receive samples of buffer from another 96-well plate). As shown in FIG. 12C, additional reservoirs can be placed on chip for the storage and transfer of cells or other samples of interest.

Figure 13:
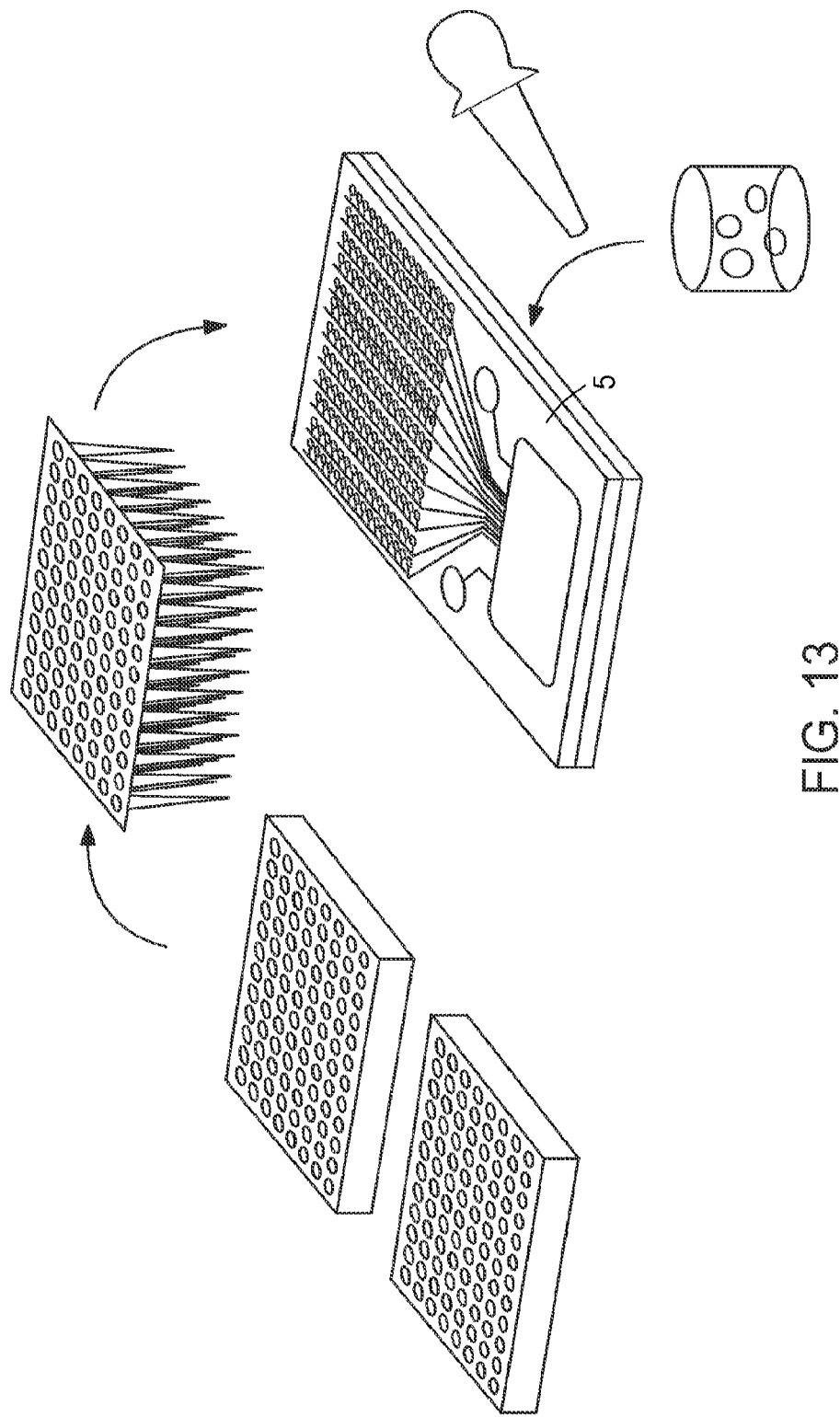

FIG. 13 is a perspective view of a kit in accordance with one aspect of the invention illustrating a process for dispensing fluids from 96-well plates onto a microfluidic chip substrate 405 comprising interdigitating reservoirs using automated array pipettors and cell delivery using a pipette.

Figure 14A:
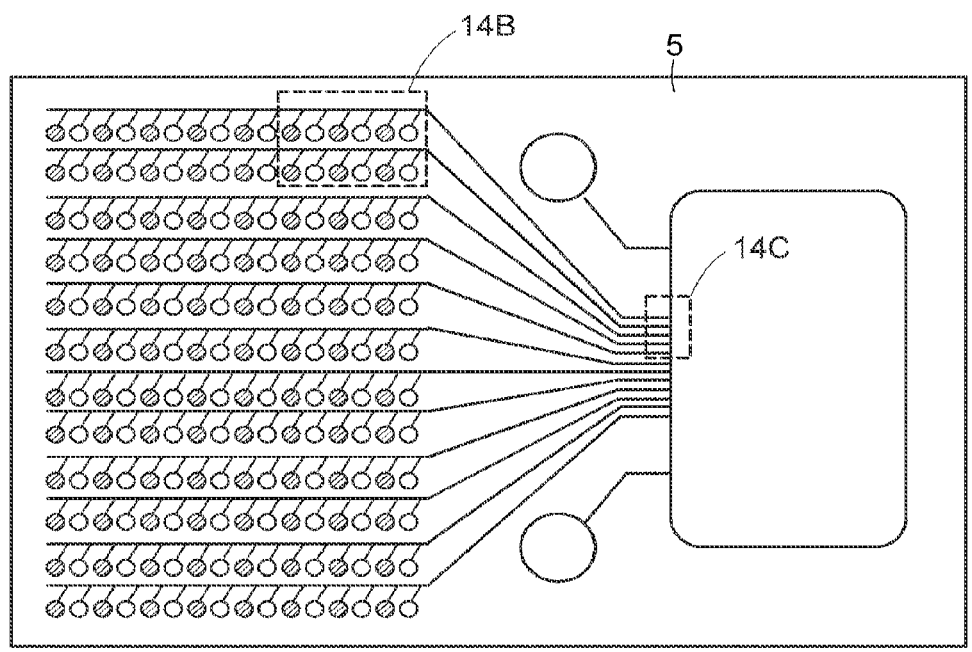
Figure 14B:
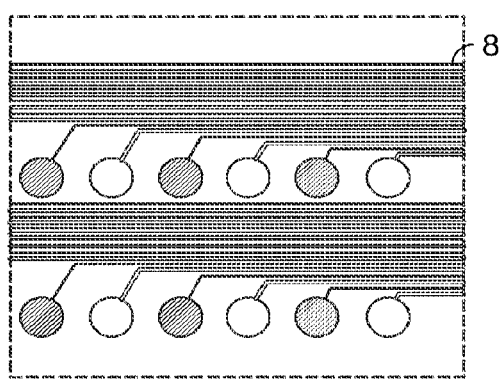
Figure 14C:
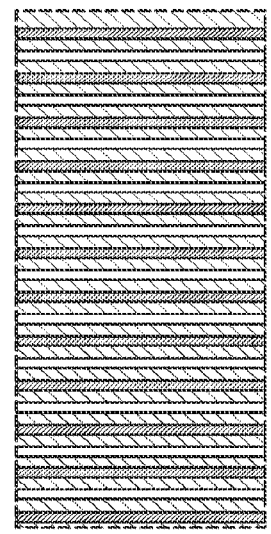

FIGS. 14A-C comprise a top view of a microfluidic chip structure for HTS of drugs according to one aspect of the invention, for scanning a sensor such as a nanoelectrode-impaled cell or cells across interdigitated ligand and buffer streams. FIG. 14A depicts the overall chip substrate 405 structure for both a 2D and 3D microfluidic system. FIG. 14B shows an enlarged view of the reservoirs of the chip and their individual connecting channels 8. FIG. 14C shows an enlarged view of interdigitating microchannel whose outlets intersect with the measurement chamber of the chip.

Figure 15A:
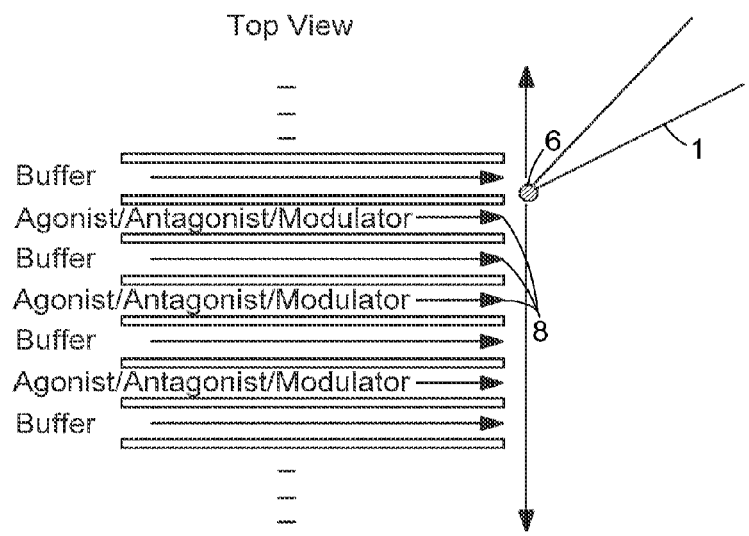
Figure 15B:
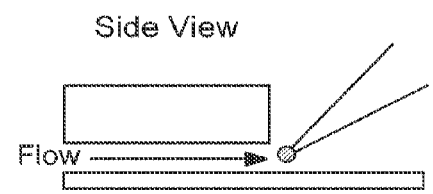
Figure 15C:
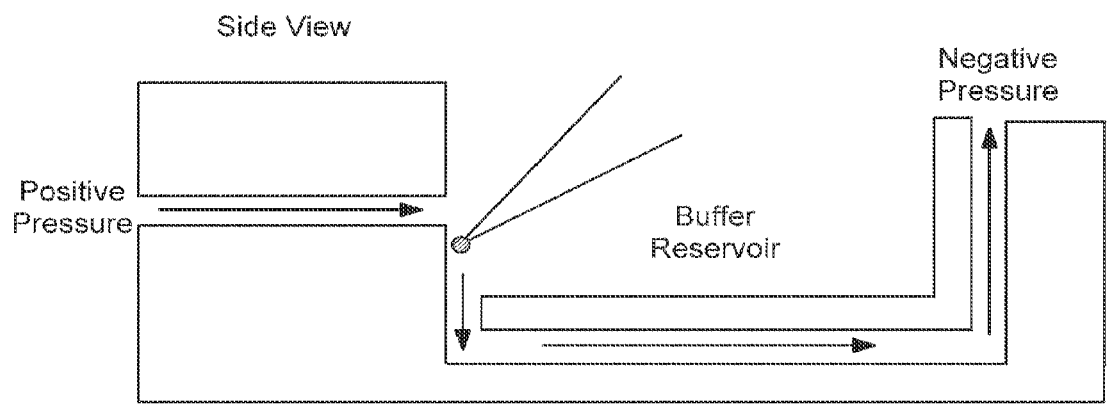

FIG. 15A schematically depicts a top view of interdigitating channels 8 of a microfluidic chip, with nanoelectrode 1-impaled or nanoelectrode 1-contacted cell 6 being moved past the outlets of the channels. FIGS. 15B and 15C depict side views of alternate embodiments of the outlets and microchannels. FIGS. 15B and 15C are side views showing a 2D and 3D microfluidic chip design, respectively. FIG. 15D is a perspective view of a 3D chip design according to one aspect of the invention, in which the chip comprises a bottom set and top set of channels. FIG. 15E is a side view of FIG. 15D, showing fluid flow can be controlled through pressure differentials so that fluid flowing out of a channel 8 in the bottom set will make a "U-turn" into an overlying channel. FIG. 15F is a top view of FIG. 15D and shows cell scanning across the "U-turn" fluid streams where microchannels 8 are shown.

Figure 16A:
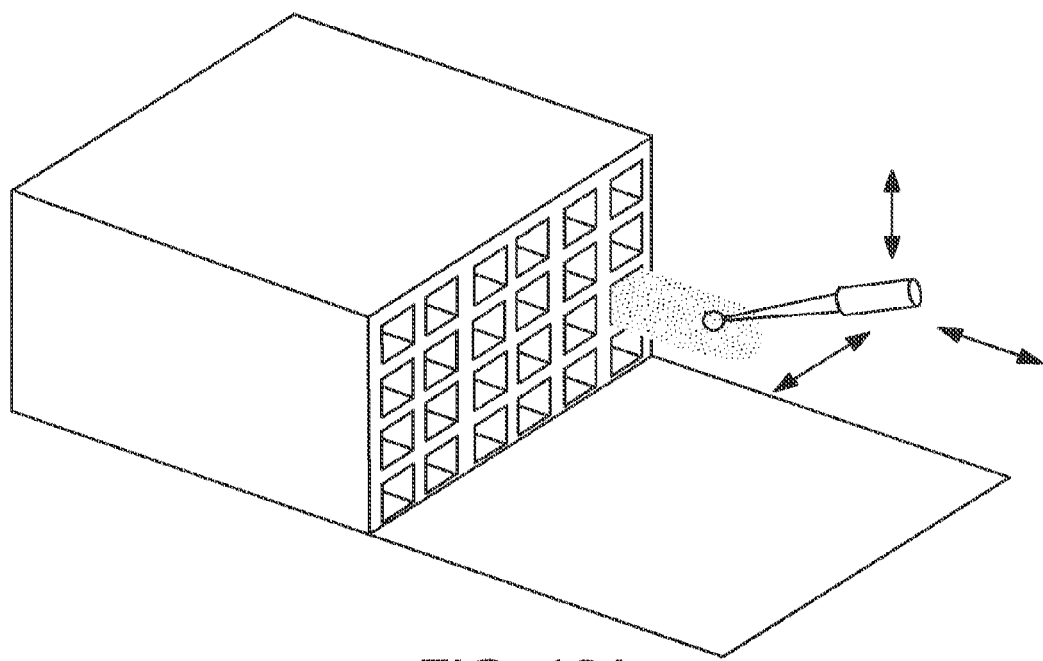
Figure 16B:
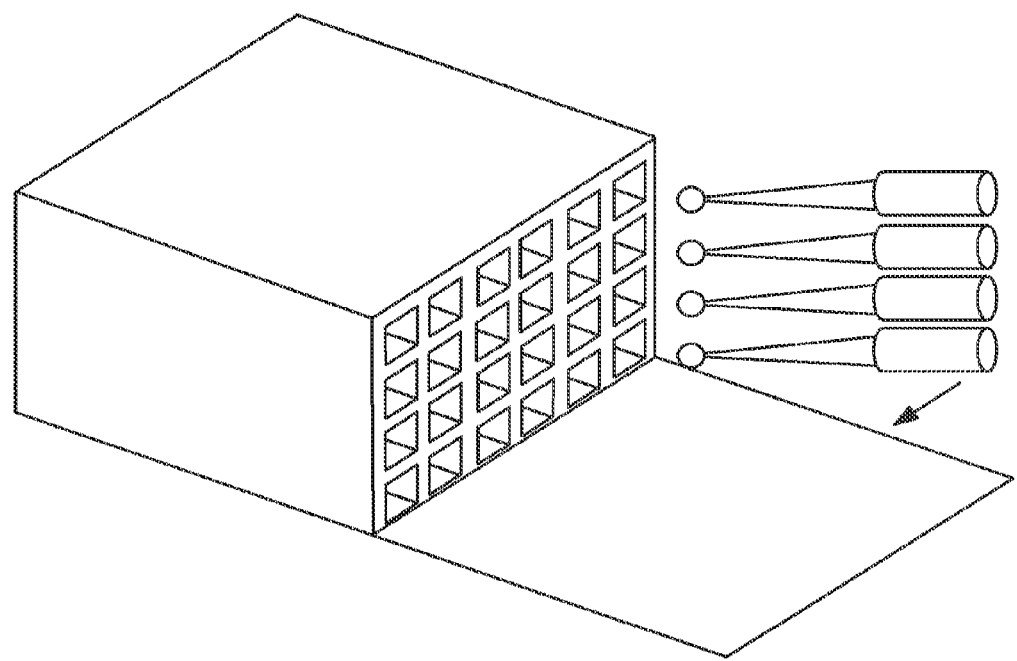

FIG. 16A is a perspective view showing a 3D array of microchannel outlet arrangements for increased throughput in HTS applications. FIG. 16B depicts the use of a microchannel array as depicted in FIG. 16A, but with a plurality of nanoelectrode-impaled or nanoelectrode-contacted cells. The arrows in the Figures indicate directions in which the nanoelectrode-impaled or nanoelectrode-contacted cell(s) can be scanned.

Figure 17A:
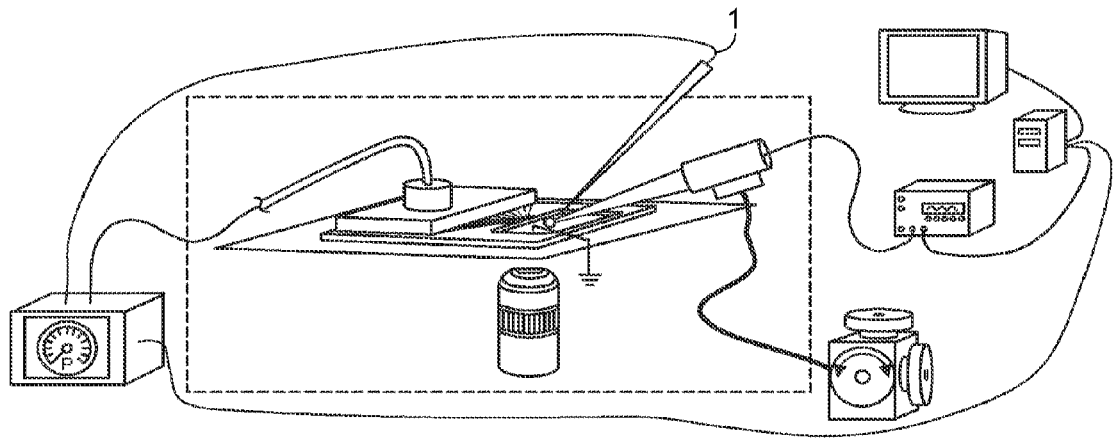
Figure 17B:
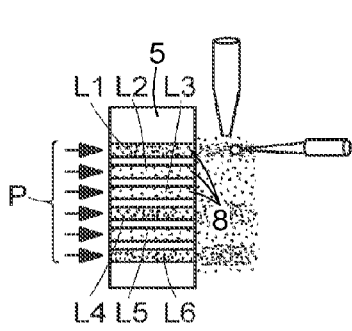
Figure 17C:
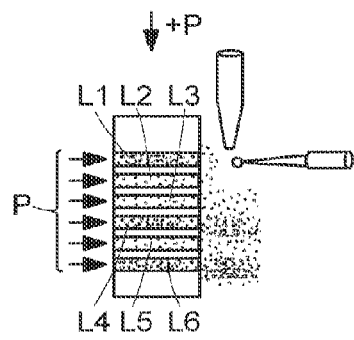
Figure 17D:
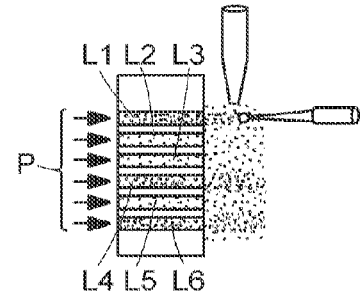
Figure 17E:
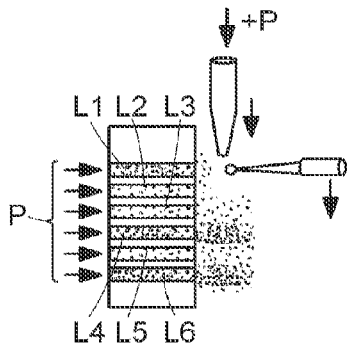
Figure 17F:
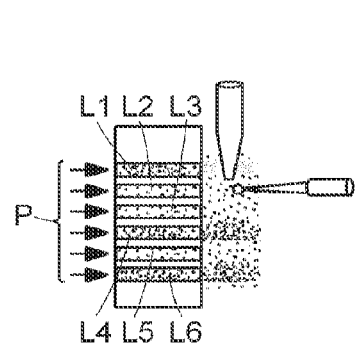
Figure 17G:
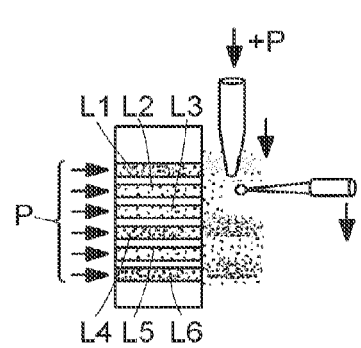
Figure 17H:
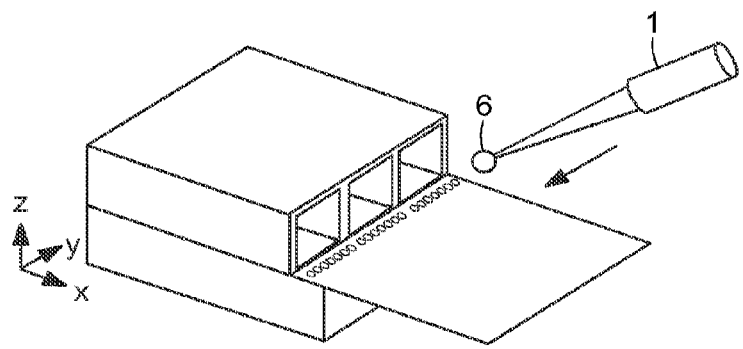
Figure 17I:
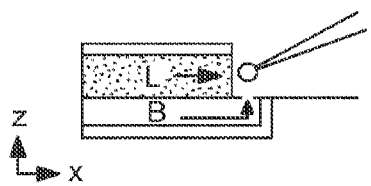
Figure 17J:
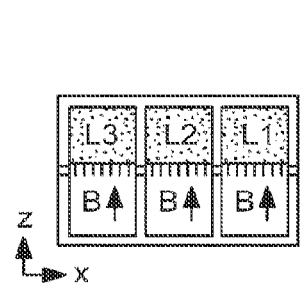
Figure 17K:
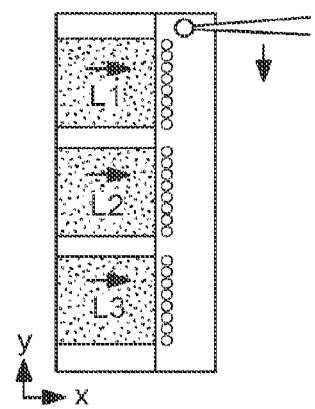
Figure 17L:
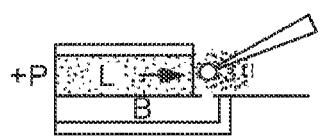
Figure 17M:
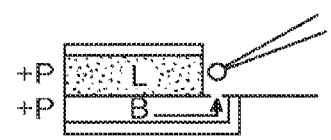
Figure 17N:
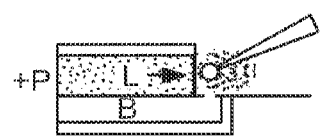

FIGS. 17A-N are schematics showing chip designs for carrying out cell scanning across ligand streams using buffer superfusion to provide a periodically resensitized sensor. FIG. 17A is a perspective view of the overall chip design and microfluidic system. Nanoelectrode 1 is shown. FIGS. 17B-G show enlarged views of the outlets of microchannels and their positions with respect to a superfusion capillary and a nanoelectrode-contacted cell, as well as a procedure for carrying out cell superfusion while scanning a nanoelectrode-contacted cell across different fluid streams. "P" indicates a source of pressure on fluid in a microchannel or capillary. Bold arrows indicate direction of movement. Substrate 505 is shown. FIGS. 17H-17N show a different embodiment for superfusing cells. As shown in the perspective view in FIG. 17H, instead of providing capillaries for delivering buffer, a number of small microchannels placed at each of the outlets of the ligand delivery channels are used for buffer delivery. As nanoelectrode 1-contacted cell 6 is moved to a ligand channel and the system detects a response, a pulse of buffer can be delivered via the small microchannels onto the cell for superfusion. The advantage to using this system is that varying the delay time between signal detection and buffer superfusion can precisely control the exposure time of the nanoelectrode-contacted cell to a ligand. FIG. 17I is a cross-section through the side of a microfluidic system used in this way showing proximity of a nanoelectrode-contacted cell to both ligand and buffer outlets. FIG. 17J is a cross section, front view of the system, showing flow of buffer streams. FIG. 17K is a cross-section through a top view of the device showing flow of ligand streams and placement of the buffer microchannels. FIGS. 1-7M show use of pressure applied to a ligand and/or buffer channel to expose a nanoelectrode-contacted cell to ligand and then buffer.

Figure 18A:
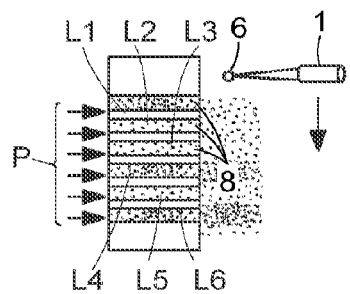
Figure 18B:
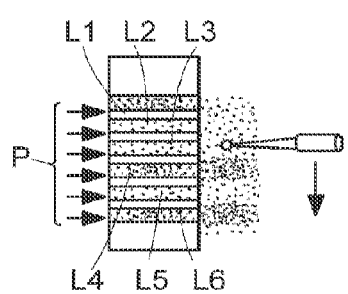
Figure 18C:
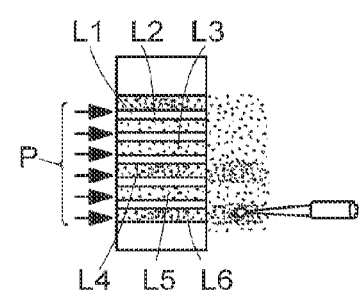
Figure 18D:
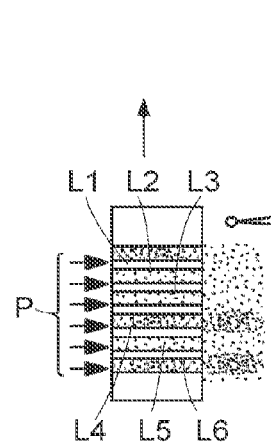
Figure 18E:
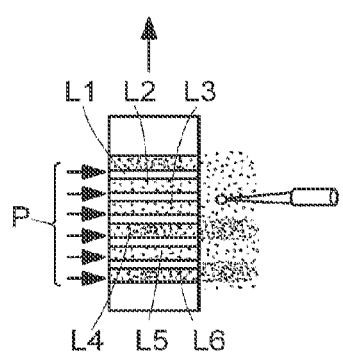
Figure 18F:
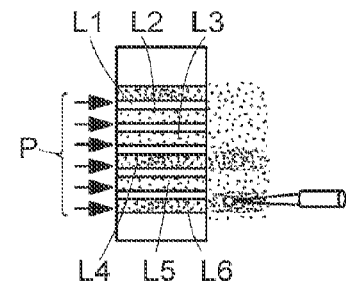
Figure 18G:
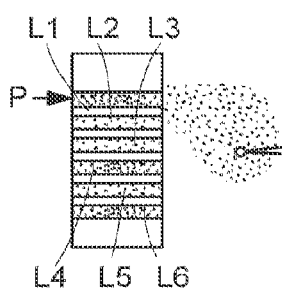
Figure 18H:
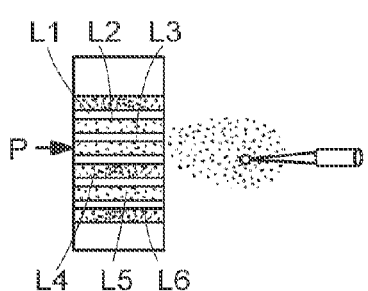
Figure 18I:
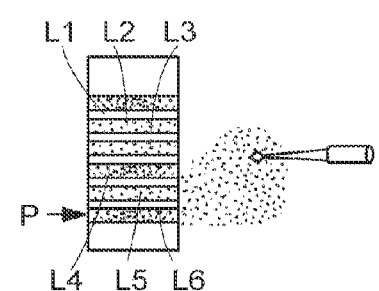

FIGS. 18A-I are top views of microchannel outlets in relationship to a nanoelectrode 1-contacted cell, 6 collectively showing different methods by which a nanoelectrode-contacted cell can be moved in relation to the fluid streams. FIGS. 18A-C show mechanical scanning of the nanoelectrode-contacted cell across stationary microchannel outlets. FIG. 18D-F show mechanical scanning of microchannel outlets relative to a stationary nanoelectrode-contacted cell. FIGS. 18G-I show a method for sweeping fluid streams across an immobilized nanoelectrode-contacted cell by controlled variation of the pressure across, and flow rates through, each individual microchannel.

Figure 19A:
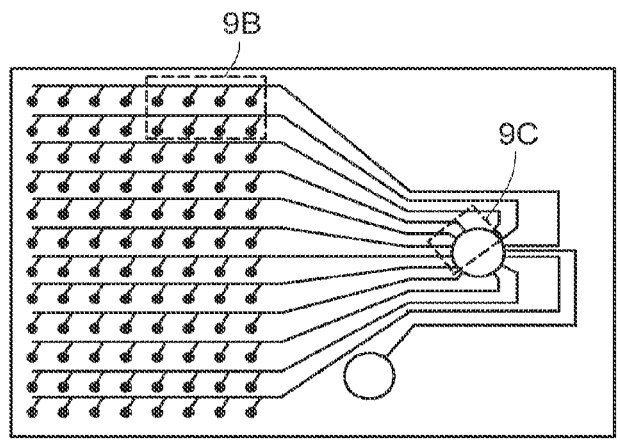
Figure 19B:
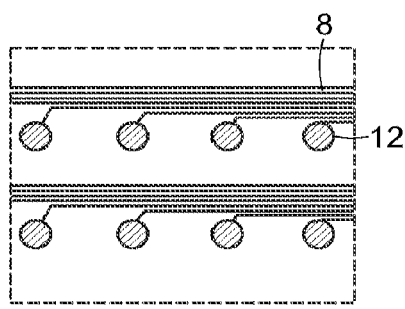
Figure 19C:
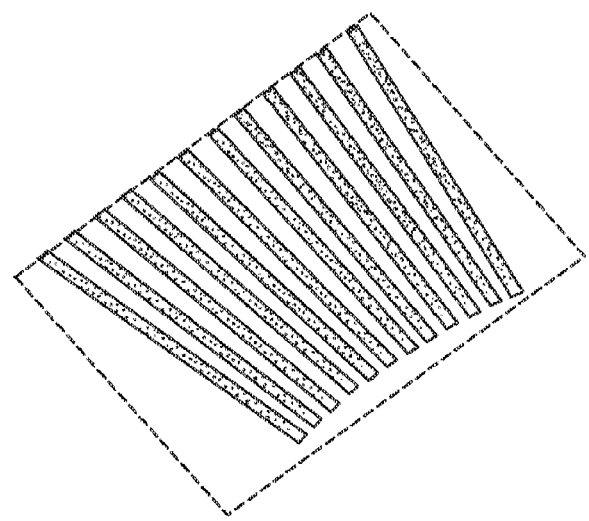

FIGS. 19A-C are top views of one design of a microfluidic chip for carrying out cycles of rapid delivery and withdrawal of compounds into and from a cell chamber for housing a nanoelectrode-contacted cell. FIG. 19A shows the overall arrangements of the microchannels feeding the cell chamber. FIG. 19B is an expanded view of reservoirs 12 and the individual channels 8 through which they are accessed. FIG. 19C shows an enlarged view of microchannel outlets that feed into the cell chamber.

Figure 20:
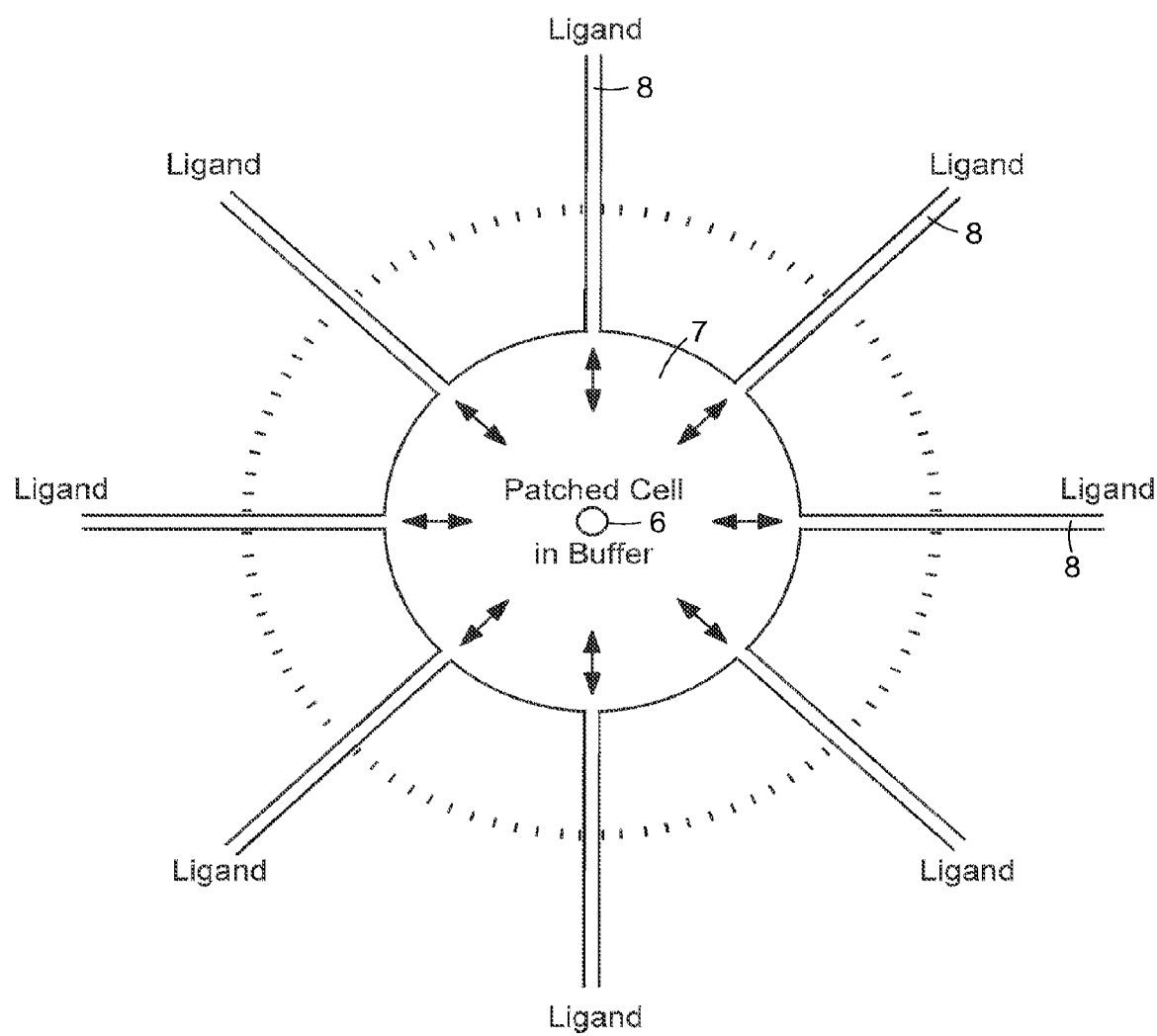

FIG. 20 is an enlarged top view of the cell chamber of FIG. 19A, depicting the arrangement of microchannels 8 around a cell chamber 7 comprising a nanoelectrode-contacted cell 6.

Figure 21A:
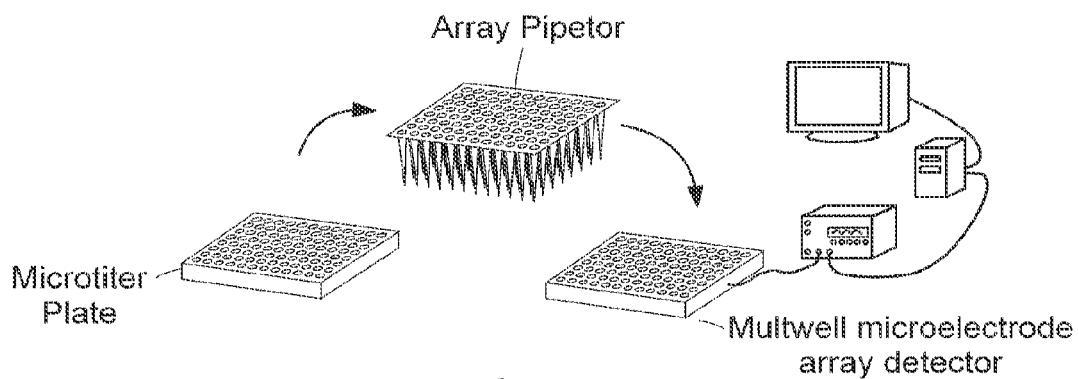
Figure 21B:
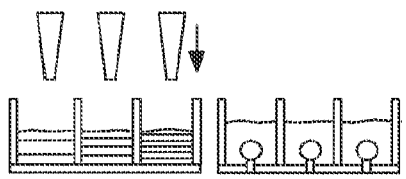
Figure 21C:
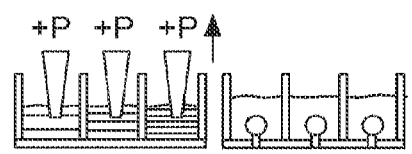
Figure 21D:
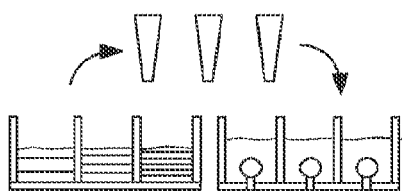
Figure 21E:
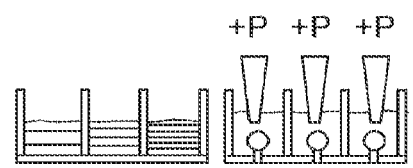
Figure 21F:
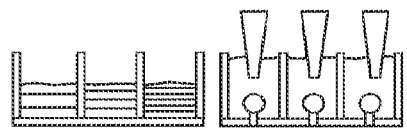

FIGS. 21A-F illustrate how multi-well type nanoelectrode arrays coupled to automated array pipetting systems can be used for increasing throughput in electrophysiological recordings. FIG. 21A shows a perspective view of a kit in accordance with one aspect of the invention illustrating a process for dispensing fluids from 96-well plates onto a multi-well type nanoelectrode array using automated array pipettors. FIGS. 21B-F shows an enlarged side view of how this aspect of the invention can be used for parallel screening of multiple compounds simultaneously.

DETAILED DESCRIPTION OF THE INVENTION

The present invention relates to methods of measuring electrical properties of a cell using electrode devices comprising tapered nanotips having submicrometer dimensions ("nanoelectrodes") for insertion into a cell. The devices are used to measure electrical properties of the cell (mediated, e.g., by ion-channels incorporated in its cell membrane) and, optionally, may be used to electroporate, the cell or subcellular structures within the cell.

The invention also provides arrays of electrode devices having nanotips for simultaneously or sequentially measuring the electrical properties of cells (e.g., such as surfaceimmobilized cells), or cells incorporated in cellular networks such as brain slices, cell cultures, and organotypic cell cultures. The electrodes can be used to measure properties of ion channels, for example, in HTS assays to identify drugs which affect the properties of ion channels.

The invention additionally provides microfluidic systems adapted for use with the electrode devices having nanotips. In combination with the nanoelectrodes, the microfluidic systems provide cell-based biosensors for monitoring cellular responses to conditions, such as exposure to candidate drugs, toxins etc.

Definitions

The following definitions are provided for specific terms which are used in the following written description.

As used herein, "an electrode device comprising a nanotip" refers to a device comprising a tip portion which is tapered to facilitate insertion of the device into a cell: "An electrode device comprising a nanotip" also refers to a device which reduces noise and improves spatial resolution in electrophysiological recordings The words nanotip and nanoelectrode are used interchangeably in the text. However, in systems comprising nanotips, the working electrode need not be of nanometer dimensions. For example, a nanotip can be filled with an electrolyte solution and the electrolyte solution can be in contact with a macroscale electrode such as a metal wire. In one aspect, a "nanotip" comprises a structure of varying diameter with a contacting end for contacting biological molecules and/or macromolecules (e.g., such as a cell or cell structure) and with its smallest diameter at the contacting end. Preferably, this "smallest diameter" is less than Preferably, the cell-contacting end comprises a diameter of less than about 500 µm, less than about 50 µm, less than about 10 µm, less than about 5 µm, or less than about 1 µm about 1 µm, and more preferably, is less than about 500 nm. As used herein, "the contacting end" refers to the surface of the nanotip which makes first contact with a biological membrane upon insertion of the nanotip into a compartment at least partially defined by a biological membrane, such as a cell or cell structure (e.g., such as an organelle), vesicle, and the like. The contacting end may be flat or tapered to facilitate insertion into the cell. Preferably, an "electrode device comprising a nanotip" comprises an electrically conducting medium (solid, liquid, or semi-solid (e.g., a gel) able to transmit electrical signals (e.g., current or voltage) from or to a cell or cell structure. Nanotips may be solid or may be hollow, comprising a housing defining a lumen. In one aspect, nanotips according to the invention comprise carbon nanotubes, such as single walled or multi-walled or scrolled nanotubes. In one preferred aspect, single-walled carbon nanotubes are used to form nanotips.

As used herein, a "biosensor" refers to a device comprising one or more molecules capable of producing a measurable response upon interacting with a condition in an aqueous environment to which the molecule is exposed (e.g., such as the presence of a compound which binds to the one or more molecules). In one aspect, the molecule(s) are immobilized on a substrate, while in another aspect, the molecule(s) are part of a cell (e.g., the sensor is a "cell-based biosensor") or are a cell structure (e.g., organelle) or comprise a compartment defined at least partially by a biological membrane.

As used herein, a "microchannel" refers to a groove, channel or trench in a substrate comprising two walls, a base, at least one inlet and at least one outlet. In one aspect, a microchannel also has a roof. The term "micro" does not imply a lower limit on size, and the term "microchannel" is generally used interchangeably with "channel". Preferably, a microchannel ranges in size from about 0.1 μm to about 1000 μm, more preferably ranging from, 1 μm to about 150 μm.

As used herein, a "cell chamber" or a "measurement chamber" refers to an area formed by walls (which may or may not have openings) surrounding a base. A chamber may be "open volume" (e.g., uncovered) or "closed volume" (e.g., covered by a coverslip, for example) and may additionally comprise outlets in one or more walls from at least one microchannel. It is not intended that the geometry of the cell chamber be a limiting aspect of the invention. One or more of the wall(s) and/or base can be optically transmissive. Generally, a measurement chamber ranges in size but is at least about 1 μm. In one aspect, the dimensions of the chamber are at least large enough to receive at least a single cell, such as a mammalian cell. The chamber also can be a separate entity from the substrate comprising the microchannels. For example, in one aspect, the measurement chamber is a Petri dish and the microchannels extend to a surface of the substrate opening into the Petri dish so as to enable fluid communication between the microchannels and the Petri dish. As used herein, the term "reservoir" and "measurement chamber" may be used interchangeably where measurements can be obtained in the reservoir/measurement chamber.

As used herein, the term "receptor" refers to a macromolecule capable of specifically interacting with a ligand molecule. Receptors may be associated with lipid bilayer membranes, such as cellular, golgi, mitochondria, or nuclear membranes, or may be present as free or associated molecules in a cell's cytoplasm or may be immobilized on a substrate. A cell-based biosensor comprising a receptor can comprise a receptor normally expressed by the cell or can comprise a receptor which is non-native or recombinantly expressed (e.g., such as in transfected cells or oocytes). A receptor can be included in a receptor/ion-channel complex or be coupled to an intracellular cascade system.

As used herein, "periodically resensitized" or "periodically responsive" refers to a macromolecule (e.g. a receptor, an ion-channel, or a receptor/ion-channel complex) which is in a specific conformational state in which this molecule can be activated by a ligand comprised in a sample. For example, in one aspect, a receptor or ion-channel is periodically resensitized by scanning it across a plurality of interdigitating channels providing alternating streams of sample (containing receptor ligands) and ligand-free buffer solution. The rate (i.e. exposure times of the cell to buffer solution and sample, respectively) at which the receptor/ion channel is scanned across the interdigitating channels is used to maintain the receptor/ion-channel in a ligand-responsive state when it is exposed to a fluid stream comprising sample. Additionally, or alternatively, the receptor/ion channel can be maintained in a periodically resensitized state by providing pulses of ligand-free buffer solution, e.g., using one or more superfusion capillaries, to the ion channel, or by providing rapid exchange of solutions in a measurement chamber comprising the ion channel.

As used herein, the term "substantially separate aqueous streams" refers to collimated streams with laminar flow.

As used herein, the term "in communication with" refers to the ability of a system or component of a system to receive input data from another system or component of a system and to provide an output response in response to the input data. "Output" may be in the form of data, or may be in the form of an action taken by the system or component of the system. For example, a processor "in communication with a scanning mechanism" sends program instructions in the form of signals to the scanning mechanism to control various scanning parameters as described above. A "detector in communication with a measurement chamber" refers to a detector in sufficient optical proximity to the measurement chamber to receive optical signals (e.g., light) from the measurement chamber. A "light source in optical communication" with a chamber refers to a light source in sufficient proximity to the chamber to create a light path from the chamber to a system detector so that optical properties of the chamber or objects contained therein can be detected by the detector.

As used herein, "a measurable response" refers to a response that differs significantly from background as determined using controls appropriate for a given technique.

As used herein, an outlet "intersecting with" a chamber or microchamber refers to an outlet that opens or feeds into a wall or base or top of the chamber or microchamber or into a fluid volume contained by the chamber or microchamber.

As used herein, "superfuse" refers to washing or flushing the external surface of an object or sensor (e.g., such as a cell).

As used herein, the term "diffusion barrier" refers to a structural or physical feature that restricts the movement of molecules (e.g., such an electrolyte solution) through an opening in a nanotip. As used herein, "movement through an opening in a nanotip" refers to movement through an electrically conducting medium within the lumen of a nanotip. In one aspect, a diffusion barrier comprises a nanotip contacting end with a diameter of less than about 500 μm, less than about 100 μm, less than about 50 μm, less than about 10 μm, less than about 5 μm, or less than about 1 μm. In another aspect, a diffusion barrier comprises a medium for lowering the diffusion of electrolytes in the electrolyte solution which is contained within the lumen of a hollow nanotip. Examples of diffusion barriers include, but are not limited to, a gel or conducting polymer that lowers the diffusionl of the electrolytes in the electrolyte solution, such as a hydrogel, e.g. polyacrylamide (e.g., doped polyacrylamide), agar, or an intrinsically conducting hydrogel like crosslinked PEDOT/PSS (Baytron P® from Bayer AG, Leverkusen), a porous structure, a membrane or the like. In another aspect, the diffusion barrier comprises an ion exchange phase, e.g., such as a negatively charged cationic exchange phase (e.g., Nafion®) or an ion shuttle compound (e.g., such as acetylacetone, hexafluoroacetylacetone, or 4-aminopent-3-en-2-one or Pyridyldiazocresol (PAC), derivative, and the like) suspended in a polymer matrix. Suitable polymer matrices include, but are not limited to, the polymer Nafion®, polymerised phospholipids or polyamides. Another approach for minimizing electrolyte leakage from the housing is to increase the viscosity of the an electrolyte solution in the housing by adding, for example, glycerol or (poly-)ethylene glycol or other suitable agent. Additional examples of diffusion barriers include non-aqueous conducting media, such as liquid-state or low melting point metals or metal alloys such as Mercury or silver/ mercury alloy, electrically conducting polymers or polymer solutions, or metal nanoparticle solutions. Such barriers may be included within the lumen of a housing or may form part of a solid nanotip.

Nanoelectrodes

The invention provides nanoelectrode devices for measuring electrical properties of a cell. In one aspect, the electrode device comprises a tip portion (a "nanotip") that is tapered, or cylindrical, to facilitate insertion of the device into a cell. The nanotip comprises a structure of varying diameter, having its smallest diameter at a cell-contacting end of the tip, i.e., the surface of the nanotip that makes the first contact with a cell during insertion of the nanotip into the cell. Preferably, the cell-contacting end of the tip has a diameter of less than about 1 µm, and more preferably, is less than about 500 nm less than about 400 nm, less than about 300 nm, less than about 100 nm, or less than about 50 nm. See, e.g., FIG. 1A). Preferably, the electrode device comprises an electrically conducting medium able to transmit electrical signals (e.g., current or voltage) from, or to, a cell.

In one aspect, the nanoelectrode device comprises a housing of glass or other suitable non-conducting materials, such as quartz, polymers, or fused silica that is filled with an electrically conductive medium. Nanotips can be generated using standard puller devices equipped with a filament to melt an elongated starting material and to stretch the material to form a tip having the appropriate dimensions. For materials with very high melting temperatures such as quartz or fused silica, puller devices equipped with a carbon dioxide laser or a Tantalum filaments are preferably used. Such fabrication methods are ideal for producing small numbers of nanoelectrodes. Alternatively, chemical or flame etching, chemical or non-chemical vapor deposition processes, thermal growth, polymerisation techniques such as electropolymerization or ion implantation can be used to microfabricate a tip of suitable dimensions.

In a further aspect, a substrate or plate is provided which comprises a plurality of solid electrode tips protruding from the plate. The tips may be hollow or solid (e.g., in the form of wires, pins, or cylinders, which may have flat or tapered (e.g., pointed) contacting ends for insertion into a cell or cell structure or other compartment at least partially defined by a biological membrane (e.g., such as a vesicle, or artifical cell). In one aspect, the nanotips comprise carbon nanotubes. Nanotubes can be generated by chemical vapor deposition using methods known in the art and can be further structured using ion milling, for example. Composite electrodes comprising carbon nanotubes and other materials also may be used. In one aspect, the substrate or plate is a polymer, e.g., including, but not limited to an elastomeric polymer, such as plastic.

In one preferred aspect, a plurality of nanoelectrode devices are assembled into an array as shown in FIG. 1B. Arrays may comprise single row or multi-rowed arrays. The electrode devices may be inserted at an end distal to a nanotip as shown in FIG. 1B or may be fabricated on a substrate as shown in FIG. 1C. The holder or substrate, or individual electrode devices, may be coupled to a micropositioner, e.g., piezo-electrically or pressure controlled, for translating the array or individual electrode device in an x-, y- or z-direction. Alternatively, the holder or substrate may be cantilevered, e.g. piezoelectrically, to allow an electrode device to be tapped against a cell membrane to facilitate insertion of at least the nanotip of an electrode device into a cell. The nanoelectrode devices might also be a part of a MEMS (microelectromechanical system) device.

A nanoelectrode device is connectable to an amplifier such as a patch clamp amplifier or a picoampmeter. In one aspect, the end of the device distal from the nanotip apex comprises a conductive region (e.g., a wire) for electrically coupling the electrode device to the amplifier. Arrayed electrode devices may be separately coupled to the amplifier, connected in clusters, or connected as a single unit to the amplifier. In one aspect, dielectric layers are provided to electrically isolate individual conductive regions and to electrically isolate individual electrode devices or clusters of devices.

In one aspect, electrode devices comprising nanotips are fabricated on a substantially planar substrate such as a chip or wafer. Non-limiting examples of different substrate materials include crystalline semiconductor materials (e.g., silicon, silicon nitride, Ge, GaAs), metals (e.g., Al, Ni), glass, quartz, crystalline or amorphous insulators, ceramics, plastics, elastomeric polymers, other polymers (e.g., a fluoropolymer, such as Teflon®, polymethylmethacrylate, polydimethylsiloxane, polyethylene, polypropylene, polybutylene, polymethylpentene, polystyrene, polyurethane, polyvinyl chloride, polyarylate, polyarylsulfone, polycaprolactone, polyestercarbonate, polyimide, polyketone, polyphenylsulfone, polyphthalamide, polysulfone, polyamide, polyester, epoxy polymers, thermoplastics, and the like), other organic and inorganic materials, and combinations thereof.

Microfabrication techniques are ideal for producing very large arrays of electrode devices. For example, electrode devices comprising nanotips can be manufactured by direct processing of a conducting solid-state material, such as shown in FIG. 1C. Suitable solid-state materials include, but are not limited to, carbon materials, indium tin oxide, iridium oxide, nickel, platinum, silver, or gold, other metals and metal alloys, solid conducting polymers or metallized carbon fibers, in addition to other solid state materials with suitable electrical and mechanical properties. In one aspect, the electrode device comprises an electrically conductive carbon material, such as basal plane carbon, pyrolytic graphite (BPG), or glassy carbon.

In one aspect, arrays are constructed on a doped semiconductor substrate by nanolithography using scanning STM or AFM probes. For example, metal clusters can be deposited either from a solution or by field evaporation from a Scanning Tunneling Microscope/Atomic Force Microscope (STM/AFM) tip onto such a substrate. The surface of the semiconductor can be oxidized so that substantially all of the surface is insulated except for tips protruding from the surface which are in contact with cells, thus minimizing electrode noise. See, e.g., as shown in in FIGS. 3A-C, for an array of solid carbon nanoelectrodes. Electrode devices may also be fabricated by chemical or flame etching, vapor deposition processes, lithography and the like.

In a further aspect of the invention, the substrate comprises a non-electrically conducting material into which holes or apertures are bored, e.g., by laser light, electrical discharges or lithography-based nanofabrication techniques such as e-beam litography. The apertures are filled with electrically conducting media and preferably a solid state conducting material, such as carbon fibers or electrically conducting polymers or metals. In one aspect, the substrate is coated with an electrically conducting material (e.g., such as a metal coating), and the rims of the apertures are raised to form tapered tips for insertion into cell membranes. In another aspect, only the raised rims of the apertures are electrically conducting. In a further aspect, only the cell-contacting surfaces of the apertures are electrically conducting. Preferably, the outer diameters of the apertures are less than about 1 µm, and more preferably, the outer diameters are less than about 500 nm.

In another embodiment, each aperture is within a well or depression in the substrate, sized to receive a cell. Preferably, the wells are less than about 100 µm in diameter, more preferably, the wells are less than about 50 µm in diameter, less than about about 25 µm in diameter, or less than about 10 µm in diameter. Wells can be formed by etching as is known in the art.

In one aspect, an electrode device according to the invention comprises a hollow housing comprising walls defining a lumen. One end of the housing comprises a tapered nanotip for insertion of the cell. Preferably, the lumen is filled with an electrically conducting medium. The electrically conducting medium can be in contact with an amplifier directly or through, e.g., a metal wire.

Suitable materials for the housing include, but are not limited to, glass, silicon, quartz, ceramics, a polymer, such as plastic, a metal, and the like. The housing may be coated with an insulating material or at least partly made of an insulating material, but preferably, the housing comprises a conducting surface at least at the nanotip (e.g., at least at the cell-contacting surface). In one aspect, the housing comprises a substantially cylindrical shank distal to the nanotip (see, e.g., as shown in FIG. 1A). In another aspect, the housing is a capillary or micropipette.

In another aspect, the housing comprises a combination of electrically conducting media within the lumen—a solid conducting medium at the end of the housing distal from the nanotip, and a non-solid conducting medium between the solid conducting medium and the nanotip. For example, the solid conducting medium may be a metallic or metallized measurement or working electrode, while the non-solid conducting medium may be a liquid, a paste, a polymer, a semi-solid medium such as a gel, a resin, and the like.

Because the non-solid medium has the potential to leak from the housing, in one preferred aspect, a diffusion barrier is provided in the tip of the housing in order to minimize leakage of solution components in the electrolyte solution when the electrode device is inserted into a cell. See, as shown in FIG. 2B. Examples of diffusion barriers include, but are not limited to, a gel or conducting polymer that lowers the diffusional velocity of the electrolytes in the electrolyte solution, such as a hydrogel, e.g. polyacrylamide (e.g., doped polyacrylamide), agar, or an intrinsically conducting hydrogel like crosslinked PEDOT/PSS (Baytron P® from Bayer AG, Leverkusen). Conductive polymers can be polymerised directly in the tip or backloaded as is routine in the art.

In another aspect, the diffusion barrier comprises an ion exchange phase, e.g., such as a negatively charged cationic exchange phase. For example, the polymer Nafion® (available from Aldrich Chemical Co., Milwaukee, Wis.) can be used and may be applied in the form of a film or a membrane, at the tip of the housing.

It is also possible to minimize electrolyte exchange by at least partially filling the housing with an ion shuttle compound suspended in a polymer matrix. Suitable ion shuttle compounds include, but are not limited to, acetylacetone, hexafluoroacetylacetone, or 4-aminopent-3-en-2-one or Pyridyldiazocresol (PAC) and derivatives. Suitable polymer matrices include, but are not limited to, the polymer Nafion®, polymerised phospholipids or polyamides.

Another approach for minimizing electrolyte leakage from the housing is to increase the viscosity of the an electrolyte solution in the housing by adding, for example, glycerol or (poly-)ethylene glycol or other suitable agent.

Still another way of circumventing the problem of electrolyte exchange is to fill the housing with a non-aqueous conducting media. Non-limiting examples of such conducting media are liquid-state or low melting point metals or metal alloys such as Mercury or silver/mercury alloy, and electrically conducting polymers or polymer solutions or a metal nanoparticle solution.

In a further aspect, the housing comprises two different types of solid electrically conducting medium. Preferably, a measurement electrode is provided at the end of the housing distal from the nanotip, while the remainder of the housing comprises a solid-state conducting material. Examples of solid-state conducting media include any suitable metal, metal alloys, carbon-metal alloys, carbon fibers, solidified conducting polymers and precipitated metal colloids See, e.g., as shown in FIGS. 2C and 2D.

Solid-state conducting media may be selected based on their ability to minimize the noise contribution of the electrode device by minimizing electrical resistance in the housing. Preferably, solid-state conducting media can be fabricated with small diameters without sacrificing strength. For example, in one preferred aspect, the solid state conducting material comprises a carbon fiber material. Methods of microfabricating carbon fiber materials are known in the art and are described in U.S. Pat. No. 4,684,336, Malinski, T. et al. *Anal. Chem. Acta.* 249:35-41 (1991); and Bailey, F. et al., *Anal. Chem.* 63:395-398 (1991), for example. The housing also may be coated with a metal coating which in turn may be coated with an insulating material (see, e.g., as shown in FIG. 3B).

Structured Electrode Devices

In one preferred aspect, as shown in FIG. 9A, the housing comprises at least two individually electrically insulated electrically conducting elements. These non-coaxial dual electrodes can be fabricated by embedding two single electrodes in a block of insulating polymer or by joining two single electrodes using double-sided insulating adhesive tape, or inserting two single electrodes in insulating tubing (such as polyimide tubing) and joining the two tubes together (e.g., by adhesive). Alternatively, dual electrodes can be etched on the outside of a cylindrical metalized surface that tapers to a point, separating the electrodes with insulating material using masking technology. Alternatively, double-barrel glass capillaries can be pulled on a filament or carbon dioxide laser puller to form dual electrode nanotips.

Preferably, in this embodiment, the housing defines two lumens, each lumen containing an electrically conducting element and defining an electrode compartment. In one aspect, the electrically conducting element comprises two different types of electrically conducting media—a solid electrically conducting medium and a non-solid electrically conducting medium. See, e.g., as shown in FIG. 9A. In another aspect, the solid electrically conducting medium comprises a measurement electrode. Preferably, the non-solid conducting medium is a liquid (e.g., an electrolyte solution, with or without a diffusion barrier), a paste, a polymer, a semi-solid medium such as a gel, a resin, a metal nanoparticle solution and the like. The two lumens may be divided by a single wall or by a double wall (e.g., fabricated from two single lumen housings placed side by side). Preferably, however the tip of the housing comprising the two lumens is less than about 1 µm, and more preferably, is less than about 500 nm.

In one aspect, the distance between the center of each solid electrically conducting medium (e.g., the center-to-center distance of two measurement electrodes) is less than 10 mm, and more preferably, is less than 100 µm, or less than 20 µm.

Sandwich electrodes also may be fabricated by providing a housing comprising layers of electrically conducting medium separated by insulating layers. For example, as shown in FIG. 9B, in one aspect a housing defining a lumen and comprising a nanotip comprises a solid state conducting material within the lumen and comprises walls made of a non-conducting, or insulating material such as glass, polymeric materials or ceramics. The non-conducting walls are coated with a conducting material such as a metal coating or a conducting polymeric coating which itself may be coated with an additional insulating layer, such as, but not exclusively, polyphenols, silicon dioxide, polysiloxanes or a fluoropolymer, e.g., such as Teflon®. Preferably, the contacting surface of the nanotip is electrically conducting and is not covered with an insulating layer. In this embodiment, rather than being side-by-side, electrode compartments are coaxial.

Dual barrel and sandwich electrode devices are especially desirable for multiple electrode registrations of a single cell or cell structure or the combination of a working electrode with a reference electrode.

For example, one electrode compartment may be used to record electrical properties of a cell or cell structure, while the other electrode may be used to stimulate a cell or to transiently electroporate a cell or cell structure and, further, optionally, to deliver a cell-impermeable solute to a cell (e.g., such as a drug or a dye). In addition, one-body multilayered, or dual barrel, electrode devices reduce cell stress and leakage by minimizing the number of injection holes needed to complete multiple operations (e.g., stimulation and recording, electroporation and recording, and the like).

Preferably, housings comprising multiple electrode compartments are electrically coupled to a reference electrode, providing a way to measure potential differences between measurement electrodes and a reference electrode and to account for background during measurements.

Duel barrel electrodes thus provide the ability to combine two very different types of electrodes which may be used on a single cell, in a single injection event. The electrodes also are generally easier to back fill.

Surface Chemistry of Nanoelectrodes

Noise associated with recording electrodes is significant and often dominant in most electrophysiological measurements. There are a variety of mechanisms by which patch pipettes (e.g., electrode devices) traditionally used in electrophysiological measurements contribute noise to the measured current in the patch-clamp technique. Dielectric noise of the pipette can be a major contributor to total noise in patch voltage clamping. The dielectric noise arising from the pipette depends on the dissipation factor (D) of the glass used to fabricate the pipette, on the pipette capacitance, and on surface chemistry of the pipette. Capacitance increases approximately linearly with increasing depth of immersion of a pipette in a cell bath solution and generally the dielectric noise for any particular type of glass and outer diameter (OD)/inner diameter (ID) ratio varies approximately as the square root of the depth of immersion.

Therefore, in one aspect, electrode devices are treated to provide optimal surface chemistries to minimize noise and to provide a good mechanical and electrical seal between a cell membrane and the electrode. Non-limiting examples of surface modifications include: hydrolyzation e.g. by UV-ozone plasma treatment or RCA-1 washing or other suitable treatment, of at least the cell-contacting surface of the nanotip, for maximizing the interaction with lipid molecule head-groups of a cell membrane; coating at least the cell-contacting surface with a coating promoting plasma membrane adhesion; coating at least the cell-contacting surface with binding partners (e.g., such as antibodies or antigen binding fragments thereof) which specifically bind to plasma membrane proteins (such binding partners may be cell-type specific or non-cell type specific); and coating at least the non-cell-contacting surface with a hydrophobic coating (e.g., by silanizing the surface with a silanizing agent such as Sylgard), promoting lipid monolayer formation. Examples of surface-modified electrode devices are shown in FIGS. 4A-B.

Moreover, structured (i.e., layered) coatings can be applied in cases when it is desirable to have extremely mechanically robust electrodes, for example in instances when stronger forces are needed to introduce an electrode device comprising a nanotip into a cell. Such coatings are particularly useful for preparing carbon fiber electrodes because the coatings enhance the stability of such electrodes and reduce the risk of breakage during application or transport. This can therefore significantly extend the lifetime of a single electrode. An example of this embodiment is shown in FIG. 4C.

In addition, to maximize seal formation, a chemically modified metal film ring can be positioned around the nanotip of the electrode device to reduce leakage at an injection site. For example, cationic lipid materials or long alkyl chain hydrocarbons can be stably associated with the metal seal (e.g., by covalent bonding). By generating attractive forces at the cell membrane, the modified metal seals may be used to stabilize the interaction between a cell membrane and a nanotip.

The small size of the tips in combination with a strong adsorption between the nanotip surface and the cell membrane assures an extremely high electrical resistance at the interface between the nanotip and cell membrane. This maximizes the amount of current that passes through the electrode device to the cell.

Maximizing Throughput: Parallel Registration Using Nanoelectrode Arrays

The combination of using nanoelectrode arrays for the registration of the electrical activity from a plurality of penetrated cells with systems as known in the art for changing the solution environment around said cells is particularly important for performing paralel high-throughput electrophysiological recordings.

Therefore in one aspect, the invention provides a system comprising a substrate that comprises a plurality of measurement chambers (e.g. greater than 10 and prefferably 96, 384 or 1536 number of chambers). Each chamber on the substrate is containing one or more cells. Preferably the center-to-center distance of each chamber on the substrate corresponds to the center-to-center distance of wells in an industry standard microtiter or multi-well plate. In addition each measurement chamber is equipped with at least one nanoelectrode device fabricated on the base of the measurement chamber as described above. Most preferably, each measurement chamber is equipped with multiple (e.g., greater than 6 and preferably greater than 30) nanoelectrodes allowing the registration of several cells in each measurement chamber simultaneously. This embodiment is illustrated in FIGS. 21A-F, for example.

The measurement chambers may be fabricated in the same material as used for manufacturing of the nanoelectrode devices or may be constituted by an other material that is bonded to the substrate comprising the nanoelectrode devices. Non-limiting examples of materials that can be used for defining the sample wells are; polystyrene, polycarbonate, PDMS, PMMA, polyethene, polyurethane, glass and silicon. Moreover, the nanoelectodes are preferrably in electrical communication with an amplifier that obtains the electrical responses generated by the cells when the nanotips of the electrode devices are inserted into cells. Most preferably, a multichannel type amplifier is used in this aspect, where each channel receives electrical responses generated by cell(s) impaled by a single nanoelectrode or a cluster of nanoelectrode located in one measurement chamber. This arrangement thus allows simultaneous recording of the electrical responses from cells located in different measurement chambers.

In order to use said substrate for parallel high-throughput electrophysiological recordings, at least one cell in each measurement chamber on the substrate is positioned and impaled by a nanoelectrode. Positioning and impaling can be achieved using movable micropositioners such as pipettes, capillaries, columns, piezoelectric cantilever systems and/or can be dispensed into a measurement chamber using a dispensor such as an nQUAD aspirate dispenser. Other methods can used to position a cell such as electrophoresis, suction, the use of voltage pulses, and the like. Most preferably all cells are manipulated onto nanoelectrodes simultaneously in a parallel fashion by the use of, for example arrays of holding pipettes coupled to a micropositioner or paralellized dielectrophoresis.

Once the nanoelectrodes are inserted into the cells to measure electrical properties (e.g. changes of voltage and current across the cell membrane) of the cell(s) the samples to be investigated are introduced into the measurement chamber(s). Preferably, the samples are manipulated and transferred, preferably, using robotic automated array pipettors as are known in the art (see, e.g., Beckman's Biomek 1000 & 2000 automated workstations, available from Beckman Coulter, Inc., Fullerton, Calif.) into the measurement chamber. In order to reduce the time of an analysis cycle, the samples are preferably superfused over the nanoelectrode impaled cells by positioning the tips of the pipettes containing the samples into the vicinity of the cells.

In one aspect, the invention provides a system comprising a one or two-dimensional array of nanoelectrodes manufactured as described above, and a substrate containing a plurality of measurement chambers where each chamber contains at least one cell. In one aspect the substrate is comprised of industry standard microtiter or multi-well plates such as 96, 384 or 1536 number of chambers. Preferably, the center-to-center distance of the nanoelectrodes in the array corresponds to the center-to-center distance of the wells in an industry standard microtiter or multi-well plate. Most preferably, the nanoelectrode array is designed in a clustered fashion where each cluster is composed of several nanoelectrodes (e.g. more than 6, or more than 30 nanoelectrodes) where the cross-sectional distance of a cluster is smaller than the cross-sectional distance of the corresponding measurement chamber and the center-to-center distance of the clusters corresponds to the center-to-center distance of the measurement chambers in the substrate. Preferably, the nanoelectodes are in electrical communication with an multichannel amplifier where each channel obtains information of the electrical properties of the cell(s) from a single nanoelectrode or a cluster of nanoelectrode, thus allowing parallel recording of the electrical responses from cells located in different measurement chambers as described above.

In order to use said nanoelectrode array for paralel high-throughput electrophysiological recordings, at least one cell in each measurement chamber on the substrate impaled by a nanoelectrode. Preferably the array of nanoelectrodes comprised within the system can be moved by the use of a micropositioner in an x-, y-, and/or z-direction to insert the nanoelectrodes into the cell(s) within the measurement chambers. In order to simplify the insertion procedure and to increase the insertion yields, the surface of the substrate in the measurement chamber is preferably micropatterned with functionalized spots promoting cell adhesion manufactured by methods as known in the art. Preferably the distances between the adhesive spots is correlating to the distances of the nanoelectrodes in the array. Preferably, the cells will spontaneously sediment, adhere and align onto the adhesive spots. If non-adherent cells are used, the substrate in the measurement chamber can comprise orifices or pipettes where cells can be trapped and held by the application of a slight negative pressure to the pipettes/orifices. In addition cells can be positioned onto adhesive spots or onto holding pipettes/orifices by any of the techniques described above.

Once the nanoelectrodes are inserted into the cell(s) to measure the electrical properties of the cell(s) the sample(s) to be investigated are introduced into the measurement chamber as described above. In order to compact the system and improve the ease of operation, the nanoelectrode array and the automated array pipettor system is preferably merged into a single unit. The benefits of this arrangement are that the nanoelectrodes are inserted into the cells and that the transfer of samples is performed in one single step of manipulation. Therefore the time of an analysis cycle can be substantially reduced. In addition, the nanoelectrode-pipettor system should be designed in such a way that the samples are introduced in close vicinity of the nanoelectrode impaled cells allowing local superfusion of sample further reducing the time of analysis In one aspect of the present invention, parallel registration using nanoelectrode arrays is preferably used in HTS applications. Here, one compound per measurement chamber is delivered to the substrate as described above and the cellular response of the compound is recorded by the nanoelectrode-amplifier system. In another aspect of the present invention, parallel registration using nanoelectrode arrays is used for performing dose-response type measurements. In this aspect one compound is delivered, by any of the techniques described above, in different concentrations, to individual measurement chambers containing nanoelectrode impaled cells. In addition, dose-response type measurements can be performed on a plurality of compounds simultaneously provided that the substrate comprises a substantial number of measurement chambers. Methods of obtaining dose-response measurements are described further in U.S. Ser. No. 60/356, 377, filed: Feb. 12, 2002).

Microfluidic Systems Comprising Nanoelectrodes

The combination of nanoelectrode-penetrated cells and microfluidics for rapidly changing the solution environment around a plurality of cells is important for performing high-throughput electrophysiological recordings.

Therefore, in one aspect, the invention provides a microfluidic system comprising a substrate that comprises a measurement chamber for containing one or more cells. A plurality of microchannels are fabricated on the substrate whose outlets intersect with, or feed into, the measurement chamber. Preferably, the system comprises one or more of the nanoelectrode devices described above.

In one aspect, the one or more nanoelectrode devices are inserted into the cell(s) to measure electrical properties (e.g. changes of voltage and current across the cell membrane) of the cell(s). The electrode devices may be fabricated directly on the substrate (e.g., on the base of the measurement chamber) or may be provided on a chip or wafer that is placed in the measurement chamber. In another aspect, one or more electrode devices are positioned in proximity to cell(s) in the measurement chamber using a micropositioner that can move the electrode device(s) or the substrate. Preferably, electrode devices are in electrical communication with an amplifier such as a patch-clamp amplifier that obtains measurements of electrical properties of the cells when the nanotips of the electrode devices are inserted into cells.

In one aspect, each microchannel of the microfluidic system comprises at least one inlet (e.g., for receiving a sample or a buffer). Preferably, the inlets receive solution from reservoirs (e.g., shown as circles in FIGS. 12A and B) that conform in geometry and placement on the substrate to the geometry and placement of wells in an industry-standard microtiter plate. The substrate is a removable component of the system and therefore, in one aspect, the invention provides kits comprising one or more substrates for use in the system, providing a user with the option of choosing among different channel geometries.

Non-limiting examples of different substrate materials include crystalline semiconductor materials (e.g., silicon, silicon nitride, Ge, GaAs), metals (e.g., Al, Ni), glass, quartz, crystalline insulators, ceramics, plastics, other polymers (e.g., a fluoropolymer, such as Teflon®, polymethylmethacrylate, polydimethylsiloxane, polyethylene, polypropylene, polybutylene, polymethylpentene, polystyrene, polyurethane, polyvinyl chloride, polyarylate, polyarylsulfone, polycaprolactone, polyestercarbonate, polyimide, polyketone, polyphenylsulfone, polyphthalamide, polysulfone, polyamide, polyester, epoxy polymers, thermoplastics, and the like), other organic and inorganic materials, and combinations thereof.

Microchannels can be fabricated on these substrates using methods routine in the art, such as deep reactive ion etching (described further below in Example 1). Channel width can vary depending upon the application, as described further below, and generally ranges from about 0.1 µm to about 1000 µm, preferably, from about 1 µm to about 500 µM, and still more preferably, from about 1 µm to about 50 µm, while the dimensions of the measurement chamber generally will vary depending on the arrangement of channel outlets feeding into the chamber. For example, where the outlets are substantially parallel to one another (e.g., as in FIGS. 12A-C), the length of the longitudinal axis of the chamber is at least the sum of the widths of the outlets that feed into the chamber. In one aspect, the width of one or more outlets of the microchannels is at least about the diameter of the cell. Preferably, the width of each of the outlets is at least about the diameter of the cell.

A cover layer of an optically transmissive material, such as glass, can be bonded to a substrate, using methods routine in the art, preferably leaving openings over any reservoirs and over the measurement chamber when interfaced with a nanoelectrode which is movable and external to the substrate itself. Preferably, the base of the measurement chamber also is optically transmissive, to facilitate the collection of optical data from one or more cells in the measurement chamber.

The microfluidic system can be used in conjunction with one or more nanoelectrode devices as described above to monitor a variety of cellular responses. As used herein, a microfluidic substrate comprising a cell or portion thereof in a measurement chamber of the substrate and one or more nanoelectrodes penetrating the cell forms a "biosensor".

Suitable cells for use in biosensors according to the invention include, but are not limited to: neurons; lymphocytes; macrophages; microglia; cardiac cells; liver cells; smooth muscle cells; skeletal muscle cells; and squid giant cells. In one aspect, mammalian cells are used. These can include cultured cells such as Chinese Hamster Ovary Cells (CHO) cells, NIH-3T3, and HEK-293 cells and can express recombinant molecules (e.g., recombinant receptors and/or ion channels). However, bacterial cells (*E. coli, Bacillus* sp., *Staphylococcus aureus*, and the like), protist cells, yeast cells, plant cells, insect and other invertebrate cells, avian cells, amphibian cells, and oocytes, also can be used, as these are well suited to the expression of recombinant molecules. Cells generally are prepared using cell culture techniques as are know in the art, from cell culture lines, or from dissected tissues (e.g brain slices) after one or more rounds of purification (e.g., by flow cytometry, panning, magnetic sorting, enzymatic treatment of tissue and the like).

A cell can be positioned in the measurement chamber using a micropositioner (which may be stationary or movable) such as a pipette, capillary, column, optical tweezer, piezoelectric cantilever systems and/or can be dispensed into a measurement chamber using a dispensor such as an nQUAD aspirate dispenser. Other methods can used to position a cell such as, suction, the use of voltage pulses (electrophoresis, dielectrophoresis, electroendoosmosis), and the like.

In one aspect, pressure-driven flow is used to manipulate the movement of cells from microfluidic channels in the substrate to the measurement chamber. Routing of cells can be affected by blocking a branch of a channel in a substrate comprising a plurality of microchannels, using valves as are known in the art (and discussed further below), thereby moving the cells along with bulk solution flow into another, selected channel or into the measurement chamber.

Additionally, or alternatively, electroosmosis can be used to produce motion in a stream containing ions, e.g., such as buffer solution, by application of a voltage differential or charge gradient between two or more electrodes. Neutral (uncharged) cells can be carried by the stream. See, e.g., as described in U.S. Published Application No. 20020049389.

Dielectrophoresis produce movement of dielectric objects, which have no net charge, but have regions that are positively or negatively charged in relation to each other. Alternating, non-homogeneous electric fields in the presence of cells cause the cells to become electrically polarized and thus to experience dielectrophoretic forces. Depending on the dielectric polarizability of the particles and the suspending medium, dielectric particles will move either toward the regions of high field strength or low field strength. The polarizability of living cells depends on the type of cell and this may provide a basis for cell separation, e.g., by differential dielectrophoretic forces. See, e.g., as described in U.S. Published Application 20020058332.

The cell chamber itself can be configured to include one or more electrical elements for creating an electrical field to aid in positioning cell(s) in proximity to an appropriate electrode compartment, e.g., to create electroosmotic flow within the cell chamber or to polarize a cell to facilitate its movement towards an electrode compartment.

A cell holder can be used to position the cell in the measurement chamber in proximity to an electrode device comprising a nanotip. Preferably, a cell holder comprises an end with an opening whose diameter is about the diameter of the cell, or less than 500 µm, and more preferably, less than about 100 µm, or less than about 50 µm. In one aspect, the diameter of the opening is slightly smaller than the cell, i.e. about 10 µm, or more preferably 5 µm. Suitable cell holders include capillaries or micropipettes and, as discussed above, cell holders can be moveable in an x-, y-, or z-direction and can be used in conjunction with electrode devices to measure the electrical properties of cells in suspension. Cells can be transiently stably associated with cell holders by moving the cell to the holder (e.g., using fluid flow, pressure differentials, electric fields, and/or optical tweezers) and applying a gentle suction on the cell holder or a small electric voltage (see, e.g., FIGS. 7A and 7B).

However, in another aspect, the measurement chamber comprises one or more compartments for receiving and keeping a cell relatively stationary with respect to an electrode device being inserted into the cell. For example, the measurement chamber can comprise a plurality of depressions, wells, orifices, or pores, which are substantially the diameter of a cell. In one aspect, an array of electrode devices is positioned in register with the compartments so that the tip of each nanoelectrode is in register with the center of a compartment (see, e.g., FIG. 7C). In a further aspect, the measurement chamber is fabricated so that there is an electrode device in each compartment.

Manipulation of Cells

The microfluidic system can be adapted for performing manipulation of cells. In one aspect, the microfluidic system provides one or more cell treatment chambers for performing one or more of: electroporation, electroinjection, and/or electrofusion. Chemicals and/or molecules can be introduced into a cell within a treatment chamber that is in electrical communication with a source of current. For example, one or more electrode devices may be placed in proximity to the chamber, or the chamber can be configured to receive an electrolyte solution through which current can be transmitted, for example, from an electrode/capillary array as described in WO 99/24110, the entirety of which is incorporated by reference herein.

Suitable molecules which can be introduced into a cell in the cell treatment chamber include, but are not limited to: nucleic acids (including gene fragments, cDNAs, antisense molecules, ribozymes, and aptamers); antibodies; proteins; polypeptides; peptides; chelates; analogs; drugs; and modified forms thereof. In a preferred aspect, the system processor controls both the delivery of molecules to the one or more cell treatment chambers (e.g., via capillary arrays as described above) and incubation conditions (e.g., time, temperature, etc.). For example, a cell can be incubated for suitable periods of times until a desired biological activity is manifested, such as a change of transcription of mRNA; change of expression of a protein; inactivation of a gene, mRNA, and/or protein; chemical tagging of a nucleic acid or protein; modification or processing of a nucleic acid or protein; inactivation of a pathway or toxin; and/or expression of a phenotype (e.g., such as a change in morphology), or intracellular blocking of an ion-channel.

The treated cells can be used to deliver molecules of interest to cells in the measurement chamber, e.g., exposing the cells to secreted molecules or molecules expressed on the surface of the treated cells. In this aspect, the system can be programmed to release a cell from a cell treatment chamber into a channel of the system intersecting with the measurement chamber, thereby exposing a cell in the measurement chamber to the secreted molecule of interest.

In one aspect, a cell is delivered from the treatment chamber to a channel whose outlet intersects with the measurement chamber. In another aspect, the scanning mechanism of the system is used to place a micropositioner in proximity to the outlet so that the micropositioner can position the cell within the measurement chamber. In another aspect, fluid flow or surface tension is used to position a cell in a suitable position.

A cell can be delivered to the measurement chamber to periodically replace a cell in the measurement chamber. In this aspect, the cell can be untreated, e.g., providing a substantially genetically and pharmacologically identical cell (i.e., within the range of normal biological variance) as a previous cell that was placed in the chamber. Alternatively, the replacement cell can be biochemically or genetically manipulated to be different from the previous sensor cell, to enable the system to monitor and correlate differences in biochemical and/or genetic characteristics of the cells with differences in sensor responses. The biochemical or genetic difference can be known or unknown.

The microfluidic system can be programmed to deliver cells from the cell treatment chamber at selected time periods based on control experiments monitoring uptake of chemicals and molecules by cells. Alternatively, the system can monitor the phenotype of cells and deliver cells when a certain phenotype is expressed. For example, in one aspect, the cell treatment chamber is in communication with an optical sensor which provides information relating to optical properties of the cell to the system processor, and in response to optical parameters indicating expression of a particular phenotype, the system can trigger release of the cell from the cell treatment chamber. Optical parameters can include the uptake of a fluorescent reporter molecule or optical parameters identified in control experiments.

In another aspect, the invention provides a system that can be used to electroporate one or more cells as well as to measure electrical properties of the one or more cells. The combination of electroporation with microfluidics and electrophysiology (or other methods for monitoring cellular responses) facilitates screening for molecules (e.g., ligands or drugs) that modulate the activity of intracellular cascade components (e.g. such as phosporylating enzymes).

In one aspect, the system is used to deliver a cell-impermeable molecule into the interior of a cell by transiently generating pores in the cell plasma membrane. In this way, the molecule can be introduced to intracellular receptors, intracellular proteins, transcriptional regulators, and other intracellular targets. The cell can be delivered to the measurement chamber and the response of the cell can be monitored (e.g., by patch clamp or by fluorescence, if the molecule is tagged with a fluorescent label). Alternatively, the measurement chamber can be modified to perform both treatment and response detection.

For example, the system can be modified to create transient pores in cells by scanning. A cell can be exposed to a pore-forming agent, as it is being translated or scanned across a plurality of different fluid streams containing different compounds by providing the pore-forming agent in one or more of the streams. Streams with pore forming agents can be interdigitated with streams that do not comprise pore-forming agents.

Electroporation also can be performed, either in a cell treatment chamber or in the cell measurement chamber, using an electrode device according to the invention. For example, a cell can be selectively permeabilized by positioning an electrode device in sufficient proximity to the cell, to expose the cell to a focused electric field of strength sufficient to obtain electroporation of the cell. Because of their small size, nanoelectrodes according to the invention can selectively permeabilize a single cell or even a subcellular organelle (e.g., such as the cell nucleus, a mitochondria, or a golgi apparatus) in a population of cells, without electroporating other cells.

While different electrode devices may be used to electroporate and record cellular responses, in one aspect, an electrode device comprising a nanotip is used for both electroporation and for recording. For example, the electrode device may comprise two electrode compartments as described above (e.g., such as in the dual barrel or in a coaxial configuration). Alternatively, a single barrel device (e.g., comprising a single electrode compartment) may be used to sequentially electroporate a cell, and to record electrical properties of the cell Preferably, an electrode device used for electroporation generates a voltage at the membrane of a cell or at a cell structure/organelle from about 10 mV to 100 V. In one aspect, a rectangular DC voltage pulse applies the electric field.

The cell may be contacted with cell-impermeable solutes and cell-impermeable solutes may be transported through pores created in the cell by during the electroporation process or after electroporation but before pores have had a chance to reseal. The solutes may be present in medium provided in the cell measurement chamber (e.g., delivered by a microchannel whose outlet opens into the cell measurement chamber). Alternatively, or additionally, solutes may be delivered through the lumen of the housing of an electrode device. The housing may comprise a physiological buffer. Solutes can be delivered to the cell by electrophoresis or electroosmosis and can be chemically separated prior to delivery to the cell.

In one aspect, the cell-impermeable solutes comprise a pharmaceutically active agent, such as a drug, nucleic acid (DNA, RNA, ribozyme, aptamer, antisense molecule, triple helix forming molecule, PNA molecule, or modified forms thereof), small molecule, chelate, peptide, protein, and the like. In another aspect, the cell-impermeable solutes comprise a biological marker or dye that is transported into the cell when the cell is permeabilized.

After transiently electroporating a cell for a sufficient period of time to allow a cell to take up a suitable amount of solute, an electrode device according to the invention is then used to measure electrical properties of the cell. Preferably, properties are monitored over time. Changes in electrical properties may be used as an indicia of a cellular response to the solute. For example, in one aspect, the cellular response measured is a change in the level of intracellular calcium or the activity of an ion channel.

Rapid Alterations of the Solution Environment Around a Sensor

The present invention is preferably used in conjugation with two-dimensional (2D) and three-dimensional (3D) networks of microfabricated channels for the complex manipulation of compounds or reagents contained in the fluid in a way that permits repeated and rapid cycles of delivery of different solutions to a cell in the measurement chamber. For example, the microfluidics used with the system enables the system to programmably deliver a ligand to a cell-based biosensor comprising a receptor. This enables the system to be used for HTS screening of samples (e.g., such as compound libraries) to monitor the effects of compounds on the responses of the biosensor (e.g. such as the electrical properties of the biosensor).

In one aspect, electrical properties of a cell are monitored using nanoelectrodes in combination with suitable amplifiers such as voltage clamp or patch clamp amplifiers. Because the system provides a scanning mechanism for changing the position of microchannels relative to a sensor, the system can be used to flush a cell with buffer after exposure to a sample compound, enabling a receptor or ion channel that is part of the cell to be resensitized prior to exposure to the next compound. Thus, the system can provide a periodically resensitized receptor for exposure to potential modulators of receptor function (e.g., such as agonists or antagonists). For receptors that do not desensitize, the system is still advantageous for providing pulsed delivery of buffer to a receptor, e.g., to remove unbound ligand from the receptor, to enhance the specificity and/or decrease background of a response.

The system's ability to transport one or more cells rapidly across different streams of fluid flowing from microchannel outlets by translating the cells across the microchannels or by translating the substrate comprising the microchannels relative to the cells. The system also can sweep different fluid streams across stationary cells by varying pressure drops across individual microchannels of the substrate. This design is derived from the discovery of a new and unique fluidic behavior; i.e., that lateral interactions and couplings between neighbouring fluid streams as they exit from a set of closely spaced microchannels into a measurement chamber can extend dramatically the distance over which these streams remain collimated. The second design exploits the reversibility of fluid behavior at low Reynold's numbers while the third design is based on the ability to rapidly exchange fluids in microchannels and chambers.

Adjacent fluid streams exiting the plurality of microchannels of a substrate according to the invention have a low Reynold's number and undergo minimal mixing by diffusion. For example, a small molecule with a diffusion coefficient of about $5 \times 10^{-6}$ cm$^2$/s would take approximately 0.1 seconds to diffuse 10 µm, but 10 s to diffuse 100 µm, owing to the square dependence of distance on diffusion time ($x^2 = 2Dt$, where D is the diffusion coefficient). Similarly, for typical proteins having D~$10^{-6}$ cm$^2$/s, it will take 0.5 seconds to diffuse 10 µm and 50 seconds for 100 µm.

However, flow rates in microchannels can vary dramatically from many meters per second to micrometers per second. Flow rate in the present system is limited to the maximum flow rate that can be used without disturbing the activity of a cell in the cell measurement chamber. For example, when a cell comprises an electrode device whose nanotip is inserted into its cell membrane, flow rate is typically on the order of hundreds of µm/s to mm/s, in order to prevent dislodgement of the cell from the nanotip.

Flow profiles of multiple fluid streams are described further in copending U.S. Provisional Application Ser. No. 60/356,377 filed Feb. 12, 2002.

At the preferred flow rates for use with cell measurements and at a cell-to-outlet distance of about 20 µm or less, different fluid streams from different microchannels are essentially distinct and separate and are undisturbed by the presence of a cell into which a nanotip is inserted. Even at much lower flow rates (e.g., <100 µm/s) that may be used, different fluid streams are still well separated. This observed behaviour (e.g., collimation of fluid streams) of fluid flow at the exits of microchannels into a measurement chamber facilitates HTS applications which require relatively rapid translation of cells with respect to different fluid streams. Spacing between microchannel outlets can be optimized to optimize separation between fluid streams, as can flow rate. For example, the more rapid the flow rate, the less mixing is observed.

Preferably, flow rate and interchannel spacing are optimized to minimize the width of a boundary zone (i.e., an area of mixing). Preferably, a boundary zone is less than about 50% of the width of a fluid stream, or less than about 40%, less than about 30%, less than about 20%, less than about 10%, less than about 5%, or less than about 1% of the width of the stream. In one aspect, the boundary zone is about 2-3 microns.

To exploit the unique behaviour of fluid flow into open volumes, the pressure applied to each of a plurality of microchannels can be individually varied for precise manipulation of each flow stream. For example, in the extreme case in which positive pressure is applied to one channel and negative pressure is applied to an adjacent channel, the fluid stream can be made to make a "U-turn", going from the channel with positive pressure to the one with negative pressure while drawing in a sheath of buffer into the channel with negative pressure. Therefore, the position, width, collimation, direction, and rate of flow, as well as the composition of the fluid streams, can be controlled by varying the relative pressure applied to each channel.

Generation of a U-shaped fluid stream has the advantage that sample delivered onto a cell from a microchannel experiencing positive pressure can be withdrawn into a waste microchannel experiencing negative pressure. This minimizes the accumulation of sample components in a measurement chamber comprising a cell into which a nanotip has been inserted. In situations where a sample (e.g., a drug, ligand, and the like) is rare and/or is expensive, the system further can be used to recycle ligand and/or to feed sample back into the system (i.e., the U-shaped stream can be turned into a closed loop).

By controlling pressure, the system can control the velocity (both amplitude and direction) of fluid streams. Velocity control also may be exercised by controlling the resistance of each channel without changing the pressure or by changing both resistance and pressure. Fluid shear also can be varied by using solutions of different viscosity (e.g., adding different amounts of a sugar such as sucrose to a fluid stream) in both the microchannels and measurement chamber. Thus, by varying a number of different parameters, the flow profile of different fluid streams can be precisely tuned.

Because the aqueous solutions flowing through the channels are non-compressible (unlike air), the width and placement of each fluid stream depends on the relative flow rate through each microchannel. Therefore, fluid streams from the microchannels also can be made to move and translate by varying the flow rate through each channel. This is most easily achieved by controlling the pressure drops across each channel or by changing the resistance of each channel.

Both scanning and the pressure and resistances of each channel can be programmed, using a system processor. Parameters which can be programmed include, but are not limited to, scanning rates, scanning direction, linear changes in the pressure and resistance of each channel, stepwise or constantly variable changes in the pressure and resistance of each channel, and the sequence of changes among the different channels. In addition, pressure and resistance changes can be based on real-time feedback signals, and these signals may be processed and computed prior to outputting new pressure and resistance parameters.

Scanning speed can be adjusted depending on the application. For example, when the cell comprises a receptor which is desensitized upon continued exposure to an agonist, the sensor can be moved from a sample-containing stream to a buffer-containing stream to allow the receptor to resensitize. By sequentially sweeping a cell across sample streams and buffer streams (mechanically or through pressure differentials), pulsed delivery of agonist and buffer can be provided, thereby generating a periodically resensitized receptor.

A cell may comprise a receptor/ion channel which does not desensitize, eliminating the need to resensitize the receptor. However, the system may still be used to provide pulsed delivery of buffer, for example, to wash a cell free of unbound compounds. In this scenario, the scan rate can be adjusted based on "noise" observed in the response. For example, the scan rate can be adjusted to achieve a dose-response over certain concentrations of sample compound.

A ligand also may irreversibly block a cell receptor rendering it unresponsive (or partly unresponsive) to other ligands in other fluid streams. In this case, pulsing with buffer will have no (or minor) effect. It is straightforward to ascertain whether the cell is inactivated by introducing compounds of known effect periodically to the cell and verifying whether an appropriate response is obtained. Preferably, the system is able to sense a lack of response by a cell as it is scanned past a selected number of sample fluid streams. For example, the system can provide a feedback signal when no response is observed in sequential recordings as a cell is scanned past a selected number of consecutive fluid streams.

In one aspect, the system executes certain program instructions when a selected number of scanning intervals in which no sensor signal has been received have gone by. For example, the system can vary pressure at particular channels to stop flow in those channels, thereby minimizing sample waste. In another aspect, in response to an absence of a response signal from a sensor over a threshold period, one or more replacement cells are delivered to the measurement chamber (e.g., from the cell treatment chambers described above).

If a sensor is translated at a constant speed compared to flow rate from channel outlets (e.g., mm/s), then the screening rate (e.g., compounds screened per second) for channels having a width and spacing of about 10 µm will be approximately 25 Hz. Using about 100 µm wide channels with channel intervals of about 10 µm, the screening rate will be about 4.5 Hz. If the translation speed is increased, the scan range may be in the range of hundreds of Hz. For some applications, e.g., where cells comprise rapidly desensitizing ion channels, fluidic channels with narrow outlets are preferred as these can provide sharp concentration profile over short periods of time. Preferably, such channels range from about 1 µm to about 100 µm in width.

Scanning rates can be uniform or non-uniform. For example, scanning rates across channels providing sample streams (e.g., providing agonists) can differ from scanning rates across channels providing buffer streams. Variable scanning rates can be based on preprogramming or on feedback signals from the sensor measurements, e.g., such as from nanoelectrode measurements of electrical properties in cells. The actual scan rate will vary depending on the exact screening system, but a typical linear scan rate will range from between about 100 µm/s to hundreds of mm/s for a sensor comprising a mammalian cell having a diameter of about 10 µm.

Pressure can be applied simultaneously to all microchannels such that a steady state flow of solutions is made to flow through all microchannels at the same rate into the measurement chamber that houses the cell. In this way, steady state concentrations of different solutions containing samples (e.g., such as ligands) or pure buffer can be established at the immediate outlet of each of the microchannels. The width of each microchannel may be adjusted to achieve the desired flow rate in each microchannel.

Although the fluid streams exiting from the parallel channels enter a measurement chamber in the embodiment discussed above, it may be more convenient and desirable to provide a set of parallel drain channels opposite the set of sample and buffer channels. A groove having an appropriate width (e.g., about 50 µm) can be placed in between, and orthogonal to, the two sets of channels (i.e., the delivery and drain channels) to accommodate scanning of a sensor in the measurement chamber. To establish an appropriate flow profile, a negative pressure may be applied to all the drain channels while simultaneously applying a positive pressure to the delivery channels. This induces fluid exiting the delivery channels to enter the set of drain channels.

FIG. 15C shows a three-dimensional microfluidic system. The main difference between this 3D structure and the planar structure shown in FIG. 15B is the displacement along the z axis of fluid flowing between the outlet of the parallel array channels (e.g., interdigitated sample and buffer channels) and the inlet of the waste channels. In this embodiment, a positive pressure is applied to all sample and buffer channels while a negative pressure is simultaneously applied to all waste channels. Consequently, a steady state flow is established between the outlets of the sample/buffer channels and the inlets of the waste channels. In this configuration, a cell, such as a cell into which a nanotip is inserted, is scanned across the z-direction flow of fluid, preferably close to the outlet of the sample/buffer microchannels.

Although the fabrication of this 3D structure is more complex than the planar structure, the presence of z-direction flow in many cases will provide better flow profiles (e.g., sharper concentration gradients) across which to scan a cell. The length over which z-direction flow is established should be significantly greater than the diameter/length of a sensor used. For example, the length of z-direction flow of a cell should preferably range from about 10 µm to hundreds of µm.

Another strategy for providing alternating sample streams and buffer streams, in addition to scanning, is shown in FIGS. 17A-N. In this embodiment, rather than providing interdigitating outlets which feed sample and buffer, respectively, into the measurement chamber, all outlet streams are sample streams. Buffer superfusion is carried out through one or more capillaries placed in proximity to one or more cells in the measurement chamber. In FIG. 17A, a cell is positioned in proximity to an outlet using cell holder as described above. A capillary is placed adjacent to the cell and can be used for superfusion, e.g., to resensitize a desensitized cell. By this means, a cell comprising an ion channel can be maintained in a periodically responsive state, i.e., toggled between a ligand non-responsive state (e.g. bound to an agonist when exposed to drugs) and a ligand responsive state (e.g. ligand responsive after superfusion by buffer).

Programmed delivery of buffer through this co-axial or side-capillary arrangement can be pre-set or based on the feedback signal from the cell (e.g., after signal detection, buffer superfusion can be triggered in response to instructions from the system processor to wash off all bound ligands), providing pulsed delivery of buffer to the cell. In one aspect, the longitudinal axis of the capillary is at a 90° angle with respect to the longitudinal axis an electrode device, while in another aspect, the longitudinal axis, is less than 90°.

Microchannel outlets themselves also may be arranged in a 3D array (e.g., as shown in FIGS. 16A-B). A 3D arrangement of outlets can increase throughput (e.g., increasing the number of samples that can be screened) and therefore increase the amount of biological information that the sensor can evaluate. In one aspect, the microfluidic system is used to obtain pharmacological information relating to cellular targets, such as ion channels.

There are several advantages to performing HTS in this format over the scanning format described in the preceding paragraphs: (1) ligand exposure time is determined by the inter-superfusion period (e.g., time between pulses of buffer) rather than by the scan speed and width of the ligand streams; (2) buffer superfusion and re-sensitization time also is determined by the duration of the superfusion pulse rather than by residence time in the buffer stream; (3) higher packing density of the number of ligand streams can be provided, thus resulting in the ability to scan a large number of ligands per experiment.

Cycles of Rapid Delivery

Another feature of the system according to the invention is that fluid can be rapidly delivered through the channels into the measurement chamber, enabling compounds to be introduced into the microenvironment of a sensor and withdrawn from that microenvironment rapidly.

Fluid flows inside micron-sized channels are laminar and reversible, a property that can be gauged by a dimensionless number, called the Reynold's number (Re): For example, typically, fluid flow having a low Re number is reversible, while at high Re numbers, fluid flow becomes turbulent and irreversible. The transition between laminar reversible flow and turbulent flow appears to occur at a Re number of about 2000, an estimation based on flow through a smooth circular channel (e.g., approximating flow through a microchannel). Even at high flow rates (m/s), Re for channels measuring a few microns in width is ~<10. This means that fluid flow in micron-sized channels fall well within the laminar reversible regime. The key feature of fluidic behaviour exploited herein is the reversibility of fluid flow.

In one aspect, positive pressure is applied at a microchannel to introduce a compound or drug into the measurement chamber. After a suitable incubation time to allow interaction between the compound/drug and one or more cells in the chamber, a negative pressure is applied to withdraw the compound/drug from the chamber. Because fluid flow is completely reversible and also because diffusion is negligible under conditions used (e.g., relatively fast flow), the drug is completely withdrawn from the chamber back into the microchannel from which it came. In this way, each compound delivered onto the cell to screen for potential interactions, can be subsequently withdrawn from the cell so the cell is again bathed in buffer, re-sensitized, and ready for interaction with the next compound delivered via a different microchannel.

This scheme is particularly useful because of the small channel and chamber dimensions used in particular aspects of the invention. A number of channel geometries can be suitable to implement this scenario, particularly, the spokes-wheel configuration described further below and shown in FIGS. 10A and 10B.

Positive and negative pressure applied to each of the microchannels can be controlled individually by the system processor such that positive pressure applied to one microchannel will cause its solution content to perfuse over the sensor while negative pressure will cause the withdrawal of this solution back to its respective microchannel, thereby leaving a cell in the measurement chamber bathed in its original buffer solution.

Rapid solution exchange can be achieved using a variety of different microchannel network geometries. In one aspect, a plurality of microchannels converge or feed into the measurement chamber, while in another aspect, a plurality of microchannels converge into a single channel which itself converges into the measurement chamber. The plurality of microchannels can comprise interdigitating channels for sample and buffer delivery respectively.

Regulation of Fluid Flow in Microchannels

Valving and Pumping

Scheme 1: Using Septums to Address Individual Microchannels

In this scheme, the reservoirs that connect to each of the microchannels are sealed by a septum, for example, using polydimethyl siloxane (PDMS) for sealing or another suitable material as is known in the art. Because the septum forms an airtight seal, application of a positive pressure (e.g., with air or nitrogen) via a needle or a tube inserted through the septum will cause fluid to flow down the microchannel onto one or more sensors in a measurement chamber (e.g., to the center of a spokes-wheel where radial microchannels converge). Application of a negative pressure with a small suction through the needle or tubing inserted through the septum will cause fluid to be withdrawn in the opposite direction (e.g., from the chamber at the center of the spokes-wheel to the reservoir feeding into the microchannel).

An array of such needle-septum arrangements allows each reservoir to be individually addressed, and therefore, each microchannel. The use of this scheme permits the simultaneous and sequential pumping and valving of the fluids contained within each of the microchannels. By exercising precise control over positive and negative pressure applied to each of the microchannels, controlled fluid flow and compound delivery onto the one or more sensors can be achieved. For designs that do not require individual addressing of the microchannels (e.g., design 1—the rapid transport of nanoelectrode contacted cells across different streams of fluids), a single or a few septa with a single or a few pressure control devices will suffice.

Scheme 2: Controlling Fluidic Resistance by Varying Channel Dimensions

Although the above design using individual septa offers great flexibility and control, for certain applications in which the sequence of compound delivery and fluid flow is predetermined, a simpler design offers simplicity and ease of implementation. In this scheme, equal positive pressure is applied to all reservoirs, for example, by using pressurized air applied homogeneously to all reservoirs via a single septum, or through the use of gravity flow caused by the difference in height between inlet and outlet reservoirs. The rapid sequential delivery of compounds from each microchannel onto one or more cells is accomplished by varying the fluidic resistance of each microchannel, which is easily achieved by varying the width and length of the each microchannel.

Fluidic resistance increases linearly with length and to the fourth power of the diameter for a circular capillary. By gradually and systematically varying the dimension of each microchannel, the time delay among the microchannels in their delivery of compounds onto one or more sensors in a measurement chamber can be controlled. This scheme is especially pertinent to high-throughput drug screening applications in which a large number of compounds are to be delivered sequentially and rapidly onto patched cell/cells with pre-determined time delays.

Scheme 3: Control of Fluid Flow with External Valves

In this configuration, compounds from each of the wells of an array well plate are introduced through external tubings or capillaries which are connected to corresponding microchannels. External valves attached to these external tubings or capillaries can be used to control fluid flow. A number of suitable external valves exist, including ones actuated manually, mechanically, electronically, pneumatically, magnetically, fluidically, or by chemical means (e.g., hydrogels).

Scheme 4: Control of Fluid Flow with Internal Valves

Rather than controlling fluid flow with external valves, there are also a number of chip-based valves that can be used. These chip-based valves can be based on some of the same principles used for the external valves, or can be completely different, such as ball valves, bubble valves, electrokinetic valves, diaphragm valves, and one-shot valves. The advantage of using chip-based valves is that they are inherently suited for integration with microfluidic systems. Of particular relevance are passive one-way valves, which are preferred for implementing some of the designs mentioned in above (e.g., such as the branched channel format discussed further below).

Maximizing Throughput: Interfacing Microfluidic Structures with Well Plates

Samples (i.e., drugs, etc.) contained in sample-well plates (e.g., industry-standard microtiter plates such as 96-well plates) are manipulated and transferred, preferably, using robotic automated array pipettors as are known in the art (see, e.g., Beckman's Biomek 1000 & 2000 automated workstations, available from Beckman Coulter, Inc., Fullerton, Calif.).

To be able to leverage the same sample transfer platform used to array a sample in a well plate, one important design parameter is to ensure the reservoir arrangements in the chip described above are compatible for use with such array pipettors. For example, preferably, the reservoirs in the microfluidic chip are arranged such that the center-to-center distance between each reservoir is identical to the center-to-center distance between each well of the well plate to which the chip interfaced. Preferably, each reservoir has a diameter suitable for receiving a fluid stream from an array pipetter without significantly impeding the flow of fluid from the array pipettor.

In addition to array pipettors, there are other suitable automated devices for transferring samples from well plates onto chips, such as robotic sequential pipettors. It is important to note that the use of these other devices may permit more flexible placement of reservoirs and microchannels on the chip, providing more flexibility in the design of channel parameters. Although a substrate suitable for interfacing between 96-well array pipettors is described in more detail below owing to the widespread use of these pipettors, it should be obvious to those of skill in the art that the general design of the chip and placement of reservoirs can be modified for interfacing with any desirable sample transfer platform, as such platforms evolve. In general, reference to 96-well plates is not intended to be limiting.

FIGS. 12A and 12B show examples of microfluidic systems according to the invention that are suitable for interfacing with a 96-well plate. FIG. 12A illustrates reservoir arrangements for which no buffer reservoirs are required. FIG. 12B illustrates reservoir arrangements for applications in which alternating (i.e., interdigitating) streams of buffer and sample are provided to a cell. In this arrangement, the center-to-center distances for both the ligand and buffer reservoirs are identical to the center-to-center distance of the wells of a 96-well plate. To compensate for doubling the number of reservoirs on chip, the diameter of all reservoirs are decreased by half.

FIG. 13 illustrates how sample solutions can be transferred from the wells of a 96-well plate into reservoirs on a chip according to one aspect of the invention using traditional robotic automated array pipettors. For a microchip with interdigitated ligand and buffer reservoirs (e.g., as shown in FIG. 12B), buffer solution can be transferred from a bath, where only one buffer is needed, or from a 96-well plate, with wells comprising the same or different buffers.

In addition to the reservoirs needed for interfacing with sources of sample and/or buffer (e.g., such as well plates), there may be additional reservoirs placed on the chip for storing and transferring cells or other samples of interest. FIG. 12C illustrates the possible placement of additional reservoirs and microchannels for storing and transporting cells into reservoirs or the measurement chamber of the system, according to one aspect of the invention.

In the embodiment shown in FIGS. 14A and 15A, microchannels are substantially parallel, having widths of about 100 µm and thicknesses of about 50 µm. The exact thickness of channels may be varied over a wide range, but preferably is comparable to, or greater than, the diameter of a cell. In the Figure, inter-channel spacings of about 10 µm are provided.

Channel Geometries

Planar Radial Spokes-Wheel Format

In this construction, a plurality (e.g. 96-1024) of microchannels are arranged as radial spokes which converge into a chamber with dimensions ranging from about 10 μm to about 10 mm which houses the sensor. The number of microchannels used are selected to accommodate the number of sample wells in an industry-standard microtiter plate, e.g., 96 to 1024 wells. In addition to the number of microchannels that match the number of inputs from the well plates, there are preferably, at least two additional microchannels, one for the delivery of buffer for superfusion/re-sensitization and the other for waste removal. The central measurement chamber can be an open-volume chamber to accommodate one or more electrode devices external to the microfluidic system or can be closed or open volume when one or more electrode devices form part of the base of the measurement chamber.

In order to provide for efficient replacement of fluids contained in the chamber by incoming fluids from the channels, the angle between the input channel and waste channel is optimized. Fluid mixing and replacement is optimal when this angle is about 180° and gets progressively worse as this angle decreases towards 0 degrees. For high flow rates (cm/s to m/s), the effect of this angle becomes progressively more important, while for low flow rates, the angle between the input channel and waste channel is less important.

To maximize efficient replacement of fluids at high flow rates, the number of radial channels can be increased such that each input channel will have a corresponding waste channel, rather than having all input channels share a common waste channel. In this format, all angles between input and output channels are about 180 degrees, ensuring optimal fluid replacement.

Three-Dimensional Spokes-Wheel Format

A three-dimensional radial spokes-wheel arrangement also can be used to efficiently replace fluids entering the measurement chamber. In this construction, one or cells are placed on a filter membrane sandwiched between a substrate comprising radial channels and a substrate comprising a waste reservoir. In this format, fluids are forced to flow down from the top layer where the radial channels reside (e.g., through input channels which feed into the radial channels), past the cell(s), then through the filters and into the waste channel. The filter thus permits the cell(s) to be superfused with fast fluid flow while supporting the cell(s), so they are not carried away or dislodged by the flow. In addition, the fluids are forced to flow past the sensors and to replace all the fluids that surround the sensors.

There are a number of advantages offered by this 3D design: (1) fluids around the cells are completely, efficiently, and rapidly exchanged; (2) cells, are firmly placed on the filter and will not be dislodged by fluid flow even at extremely high flow speed, because in the axial or z-direction, the flow pushes the cells against the filter; and (3) a minimal number of radial channels is required in comparison with the planar radial design described above.

One preferred embodiment of the 3D radial spokes-wheel format is shown in FIG. 13. The main difference between this 3D structure and the planar structure shown in FIGS. 10A-D is the presence of z-direction flow of fluids from the outlets of the microchannels to the inlet of the waste microchannel. Another difference is the presence of a porous membrane on which the sensor(s) (e.g., cells) are placed, which provides mechanical support for the sensors as the z-direction flow pushes the cell against the membrane. In this embodiment, the arrangements and dimensions of the microchannels are comparable to that of the 2D planar format (FIG. 12).

Although the fabrication of this 3D structure is more complex than the planar structure, the presence of the z-direction flow in many cases provides better flow profiles, especially for open volume reservoirs. Because the sensors are placed immediately outside (i.e., on top) of the inlet of the waste channels, both sample streams and superfusion streams are forced to flow past cell (s) in the measurement chamber which results in more efficient and complete dosing of the cell(s) by the different fluid streams. Also, the presence of the porous membrane support permits the use of higher flow rates and thus higher throughput.

Branched Microchannel Format

The invention also provides a microfluidic system comprising branched microchannels. In this design, preferably only two channels are placed directly adjacent to one or cells), one for the delivery of compounds and the other for waste. Rather than separating all the input channels and converging the outlets of each input channel so they feed into a center measurement chamber, channels are arranged in a branched geometry. To interface with 96-1024 well plates, the single delivery channel adjacent to the sensor(s) is connected to a multitude of input microchannels, each input channels receiving input from a different well of the 96-1024 well plate. This format has the advantage that the channel delivering compounds and the waste channel can be placed in very close proximity to the sensor(s), thereby ensuring a rapid response from the system. The delivery of the large number of compounds onto the sensor(s) in rapid succession is achieved by the controlled and multiplexed delivery of fluids containing compounds into the single channel feeding directly into the measurement chamber.

One preferred embodiment of this design is shown in FIGS. 14A-C and 15. In this embodiment, a "fish-bone" structure is fabricated with each "bone" corresponding to a sample (e.g., a ligand) delivery microchannel which intersects with a main "spine" microchannel which is connected to a buffer reservoir. The rapid and sequential delivery of sample and buffer onto one or more sensors in a measurement chamber is achieved by first applying a positive pressure to one of the sample delivery microchannels, thus introducing a plug of sample (e.g., such as a ligand) from that microchannel into the main microchannel containing the buffer. This plug is introduced onto the cell by applying positive pressure to the buffer reservoir, which carries the plug onto the sensor, and then washes the sensor (e.g., resensitizing it) with the buffer solution. This cycle of delivery of sample and buffer superfusion is repeated with different samples contained in different microchannels. The layout of this chip design is shown in FIGS. 14A-C. In the embodiment shown in the Figures, the chip can be interfaced with a 96-well plate.

FIG. 15 is an enlarged view of the area around the main buffer channel and the measurement chamber. The dimensions (width and thickness) of the microchannel (for both sample delivery and buffer delivery) can be highly variable, with typical dimensions ranging from about 1-100 μm, and preferably from about 10-90 μm. Flow rate also may be varied with preferred flow rates ranging from vm/s to cm/s.

Pressure is isotropic, therefore, upon application of a positive or negative pressure, fluids will flow along any pressure drop without preference to any particular direction. Therefore, preferably, passive one-way valves are integrated at the junction between sample delivery microchannels and the main buffer channel. The purpose of these integrated one-way valves is to prevent any flow from the main buffer channel into each of the sample delivery microchannels upon application of a positive pressure to the buffer reservoir, while allowing flow from each of the sample delivery microchannels into the main buffer channels when positive pressure is applied to reservoirs providing sample to these microchannels. There are numerous suitable designs for microfluidic valves as well as pumping mechanisms.

Although the discussion below emphasizes pressure driven flow owing to its simplicity of implementation, a number of appropriate means can be designed for transporting liquids in microchannels, including but not limited to, pressure-driven flow, electro-osmotic flow, surface-tension driven flow, moving-wall driven flow, thermo-gradient driven flow, ultrasound-induced flow, and shear-driven flow. These techniques are known in the art.

Measuring Electrical Properties of Cells

The system can be used to monitor cellular responses by measuring changes in electrical properties (such as transmembrane voltage and current) of cells. In one aspect, the system comprises an amplifier for monitoring the response of cells in the measurement chamber to solution flow from the channels. One response which can be monitored is a change in an electrical property of the biosensor in response to gating of an ion channel. For example, a change in current/voltage flowing across the membrane of the biosensor can be measured using a voltage clamp/current clamp technique. Currents can be in the range of a few picoampere (pA) (e.g., for single ion-channel openings) to several µA (for cell membranes of larger cells such as *Xenopus oocytes*).

Preferably, a change in one or more electrical properties of the cell is monitored as a means of determining the presence of a ligand or other compound in a fluid stream coming into contact with the cell. For example, an electrical signal can be recorded by an electrode in the micropipette and transmitted, preferably with amplification, and via an analog/digital converter to the system processor. A reference electrode, which contacts solution in the measurement chamber, also is required.

Various supporting solutions can be adapted for use in measurement chamber. The type of solution will depend on the sensor and compounds being evaluated. For example, a sensor solution can be a recording solution used for traditional patch clamp analysis of an ion channel. In general, the exact composition of a solution for patch clamp recording will vary depending on the type of channel being evaluated (see, e.g., U.S. Pat. No. 6,333,337, for potassium channels; U.S. Pat. No. 6,323,191, for Cl⁻ channels, and PCT/US99/02008 9938889, for sodium channels); such solutions are well known in the art.

In one aspect of the invention, recording is automated and controlled by the system processor. For example, the system processor may direct the movement of one or more electrode devices to pre-programmed locations. In another aspect, the system processor directs the movement of the one or more electrode devices in response to image analyses of cells in the measurement chamber (e.g., the system monitors the delivery of cells to the from one or more treatment chambers). In a preferred aspect, acquisition and analysis of data, followed by a feedback control to vary microfluidic settings (e.g., pressure, valves and switches) and to control scanning parameters (e.g., speed and trajectory of scanning), is implemented by the system processor.

This invention exploits the potential for using microfluidic systems to control the delivery of a large number of different biologically active molecules and compounds (e.g., candidate drugs) to a sensor comprising a target molecule. Suitable molecules/compounds which can be evaluated include, but are not limited to, drugs; irritants; toxins; proteins; polypeptides; peptides; receptor modulators (e.g. such as lectins), amino acids; analogs and modified forms of proteins; polypeptides, peptides, and amino acids; antibodies and analogs thereof; immunological agents (e.g., such as antigens and analogs thereof, haptens, pyrogens, and the like); cells (e.g., such as eukaryotic cells, prokaryotic cells, infected cells, transfected cells, recombinant cells, bacteria, yeast, gametes) and portions thereof (e.g., cell nuclei, organelles, secretogogues; portions of cell membranes); viruses; receptors; modulators of receptors (e.g., agonists, antagonists, and the like); enzymes; enzyme modulators (e.g., such as inhibitors, cofactors, and the like); enzyme substrates; hormones; metabolites and analogs thereof; nucleic acids (e.g., such as oligonucleotides; polynucleotides; fibrinotides; genes or fragments, including regulatory sequences, and/or introns, and/or coding regions; allelic variants; RNA; antisense molecules, ribozymes, nucleotides, aptamers), including analogs and modified forms thereof; metal clusters; and inorganic ions.

Combinations of two or more of any of these molecules also can be delivered, sequentially or simultaneously, to one or more sensors in the measurement chamber. Compounds also can be obtained from synthetic libraries from drug companies and other commercially available sources known in the art (e.g., including, but not limited, to the LeadQuest® library comprising greater than 80,000 compounds, available through http://www.tripos.com/compounds/; ChemRx Diversity Library, comprising 1000 to 5000 compounds per scaffold, available through http://www.chemrx.com; the Nanosyn Pharma library, available through Nanoscale Combinatorial Synthesis Inc., Menlo Park, Calif., and the like) or can be generated through combinatorial synthesis using methods well known in the art. In aspects in which molecules are delivered to cells, any of the molecules described above may be taken up by cells by transiently exposing the cells to an electric field (e.g., in a cell treatment chamber or in a measurement chamber which is adapted for electroporation) as described above.

Providing Periodically Resensitized Ion Channel Sensors

In one aspect, the invention provides a biosensor comprising an ion channel and the system is used to monitor ion channel activity. Suitable ion channels include ion channels gated by voltage, ligands, internal calcium, other proteins, peptides, lectins, membrane stretching (e.g., lateral membrane tension) and phosphorylation (see e.g., as described in Hille B., In *Ion Channels of Excitable Membranes* 1992, Sinauer, Sunderland, Mass., USA). In another aspect, the ion-gated channel is a voltage-gated channel. Voltage-gated channels open in response to a threshold transmembrane voltage. Voltage-gated sodium, potassium, and calcium channels are all essential for conducting an action potential (or a nerve pulse) down an axon (e.g. a nerve terminal), thereby initiating the release of neurotransmitter which activates (by depolarizing the cell membrane) or inactivates (by hyperpolarizing the cell membrane) the firing of another nerve cell. These ion channels typically comprise a transmembrane sequence with a lysine and/or arginine-rich S4 consensus sequence. The positive amino acids within the S4 sequence are thought to "sense" voltage across a cell membrane, causing an ion channel containing the sequence to either open or close under different voltage conditions.

In another aspect, the ion channel biosensor is a ligand-gated channel. Ligand-gated channels open or close in response to ligand binding. There are two types of ligand-gated channels, those gated when bound by ligands inside the cell and those gated by ligands outside the cell. Ion channels gated by ligands from outside of the cell are very important in chemical-mediated part of neurotransmission. These types of ion channels are gated by neurotransmitters, which are the small molecules that actually carry the signal in synapses between two nerve cells. Ion channels gated from the inside of the cell are generally controlled by second messengers, which are small signaling molecules inside the cell. Intracellular calcium ions, cAMP and cGMP are examples of second messengers. The most common calcium-gated channel is the calcium-activated potassium channel. This ion channel can generate oscillatory behavior (e.g., for frequency tuning of hair cells in the ear) upon changes in membrane voltage when placed in a positive feedback environment.

In yet another aspect, the ion channel is gated by another protein. Certain signaling proteins have been found to directly gate ion channels. One example of this is a potassium channel gated by the beta-gamma subunit of the G protein, which is a common signaling protein activated by certain membrane receptors.

In a further aspect, the ion channel is modulated by phosphorylation. Phosphorylation can be mediated by a protein kinase (e.g., a serine, threonine, or tyrosine kinase), e.g., as part of a signal transduction cascade.

In still a further aspect, the cell-based biosensor comprises a mechanotransduction channel that can be directly gated by a mechanical trigger. For example, the cell-based biosensor can comprise the cation channel of an inner ear hair cell, which is directly gated by a mechanical vibration such as sound. Bending of the hair bundle in a particular direction will affect the probability of channel gating, and therefore, the amplitude of a depolarizing receptor current.

In another aspect, the cell-based biosensor comprises a receptor, preferably, a receptor coupled to a signal transduction pathway. For example, the cell-based biosensor can comprise a G Protein Coupled Receptor or GPCR, glutamate receptor, a dopamine receptor, a serotonin receptor, a noradrenergic receptor, a metabotropic glutamate receptor, a hematopoietic receptor, or a tyrosine kinase receptor. Biosensors expressing recombinant receptors also can be designed to be sensitive to drugs which may inhibit or modulate the development of a disease.

Binding a compound (such as an agonist or modulator or drug) to a broad range of ion channels not only evokes conformational changes in these channels, allowing a flux of ions across a cell membrane, but also causes the ion channel to desensitize, i.e., to reside in a long-lasting, ligand-bound, yet shut-off and non-conducting state (see, e.g., Jones and Westbrook, 1996, *GL Trends Neurosci.* 19: 96-101). Desensitization of many types of ion-channels usually occurs within a few milliseconds and is thought to be one of the mechanisms by which synaptic information in the central nervous system is processed and modified. Densitization also may serve as a negative feedback mechanism that prevents excitotoxic processes caused by excessive activation of ion channels by neurotransmitters or other neuromodulators (see, e.g., Nahum-Levy, et al., 2000, *Biophys J.* 80: 2152-2166; Swope, et al., 1999, *Adv. Second Messenger Phosphoprotein. Res.* 33: 49-78).

In one aspect, to achieve high screening rates in, for example, HTS applications, cell(s) in the measurement chamber are moved from the outlet of one microchannel to the next in rapid succession. To achieve rapid resensitizaton of ion channels and receptors, microchannels delivering samples comprising suspected modulators, agonists, or drugs of receptor/ion channels are interdigitated with microchannels delivering buffer for resensitization of the receptor/ion channels (e.g., buffer free of any agonist). In addition to resensitizing ion channels and receptors, this delivery of buffer onto cells between ligand and drug exposure serves to wash out ligands and drugs previously administered to the cell. Thus, in this aspect, the system is used to screen for an agonist or modulator or drug of a specific ion-channel by providing a cell or cell membrane fraction comprising a periodically responsive ion channel sensor.

In another embodiment, an additional superfusion pipette proximal to a cell, e.g., in an arrangement that is adjacent to or coaxial with respect to the cell is used to continuously resensitize/wash receptors/ion channels on the cell surface. This enables cells to be extremely rapidly resensitized and washed (e.g., within ms) and enables several different readings/registrations of ion channel activation to be made as a cell moves across a channel outlet. Agonists with known pharmacological action (e.g., known efficacy, or potency) have been included in certain channels to serve as internal standards or test compounds. This type of repeated superfusion of cells during their passage across a single microchannel outlet allows dose-response information and high signal-to-noise ratios to be obtained for receptors/channels that rapidly desensitize.

To obtain desired data, variable scan rates of cell(s) across individual streams of sample and buffer and variable pressure drops across each microchannel can be implemented by the system, either from pre-programmed instructions or in response to feed-back signals from a detector in electrical communication with the nanoelectrode (e.g., based on a detected signal or in real-time).

The system thus can be used to change microenvironments rapidly around a cell comprising a receptor/ion-channel. For example, the system can provide a periodically responsive ion channel. Because of the small dimensions of the substrates and microchannels used herein, which allows for rapid mass transport, the system enables a user to screen for drugs at the rate of hundreds per second (i.e., hundred of thousands per hour) using one cell biosensor, provided drugs and resensitization solutions are delivered sequentially at a comparable rate to the sensor. As discussed above, scanning rates can be modified to account for the physiological responses or kinetics (e.g., for kinetics of a population of ion channels included in the cell-based sensor) of a cell-based sensor, e.g., providing slower scanning rates for receptors that equilibrate slowly.

Generating Dose-Response Curves and Analyzing Ion-Channel Pharmacology

Dose-response curves provide valuable information regarding the actions and potencies of drugs. Obtaining dose-response curves using traditional methods involving micropipettes often can be time consuming and tedious. The present invention, which uses microfluidics for the rapid and controlled manipulation of the microenvironemnt around cell(s), is uniquely suited for dose-response measurements. Dose-response relationships most often follow a sigmoidal curve in a lin-log plot, and can be described by the Hill logistic functions:

$$I = I_{max}/[1+(EC_{50}/C)^n]$$

Where I is the whole-cell current, C is the concentration of ligands, $I_{max}$ is the maximal current (i.e., when all channels are in the open state), $EC_{50}$ is the half-maximal value (i.e., when half of the receptor population is activated, and often equals $K_D$, the dissociation constant of the ligand), and n is the Hill coefficient that reflects the stoichiometry of ligand binding to the receptor.

In one aspect, to achieve dose-response information for agonists, nanoelectrode contacted cell(s) in the measurement chamber are moved from the outlet of one microchannel to the next in rapid succession. Microchannels delivering agonists at different concentration are interdigitated with microchannels delivering buffer free of agonist (e.g., to resensitize receptors/ion channels and/or to wash out compounds previously administered to the cell, as described above). Preferably, the serially or sequentially diluted agonists are loaded into different channels.

Similarly, with some modifications, dose-response curves can be obtained for antagonists as well using the system which is described in more detail below. Furthermore, the system can provide a wide range of information about the actions of modulators on ion-channels, e.g., such as the association and dissociation constants of a ligand for its receptor, and whether a modulator is an agonist or an antagonist of a receptor. It is also possible, however, to obtain dose-response information from accumulated responses of ligands without washing or resensitizing the receptors with interdigitated flows of buffer. In this aspect, the microchannels need only contain ligand solutions at different concentrations.

(i) Detection and Characterization of Agonists

Partial Agonists

The ability of a drug molecule to activate a receptor is a graded property, rather than an all-or-nothing property. If a series of chemically related agonists acting on the same receptor are tested on a cell, the maximal response (i.e., the largest response that can be produced by an agonist in high concentration) generally differs from one agonist to another. Some compounds (known as "full agonists") can produce a maximal response whereas others, referred to "partial agonists", can only produce a submaximal response. Some partial agonists can even act as inhibitors when they reach a certain concentration level, and thereby block the action of a "full agonist" when binding to the receptor, provided that the "partial agonist" has a higher affinity for the receptor compared to the "full agonist". Thus, by using a defined ion-channel together with a known agonist that produces a maximal response, the grade of an agonist's activity can be monitored.

(ii) Detection and Characterization of Antagonists

In one aspect, the system is used to screen for antagonists of ion-channel activity. Suitable ion-channels which can be evaluated include: (i) ion channels that do not desensitize; (ii) ion-channels that desensitize (iii) ion-channels that desensitize but which mediate large current fluctuations when activated; and (iv) ion-channels whose desensitizing property is blocked by irrevesible binding of an allosteric modulator (e.g., such as a lectin). To detect antagonists, the ion-channels or receptors expressed by a biosensor need to be activated or "tested" by an agonist during, before, or after, application of the antagonist. For example, different antagonists can be applied together with a well-defined agonist with known pharmacological properties. Antagonists at different concentrations also can be loaded into microchannels together with agonists at a constant concentration.

To achieve rapid resensitizaton of ion channels and receptors, microchannels containing agonist and antagonist (e.g., such as ligands and drugs) are interdigitated with microchannels delivering buffer free of any agonist or antagonist (e.g., buffer for resensitization of the receptor/ion channels). In addition to resensitizing ion channels and receptors, exposure of cells to buffer between periods of exposure to ligands and drugs serves to wash out ligands and drugs previously administered to the cell. Thus, in this aspect, the system is used to provide a periodically responsive ion channel sensor. Antagonists are detected in this system by their inhibition of the agonist-induced response.

In another aspect, the system is used to screen for antagonists which can be detected through attenuation in the signal mediated by constantly pre-activated receptors/ion-channels. In this particular setup, different channels are loaded with different antagonists, or with the same antagonist at different concentrations, or a combination of both, while each channel comprising antagonist comprises agonist at a constant concentration. To achieve continuous activation of receptors and ion channels, microchannels containing agonist and antagonist are interdigitated with microchannels delivering buffer and agonist at the same concentration as in the channels supplemented with antagonist. This delivery of buffer supplemented with agonist onto cells between ligand and drug exposure serves to wash out ligands and drugs previously administered to the cell and also can serve to resensitise a receptor/ion channel. Antagonists can also be detected through their attenuation of responses mediated by voltage-dependent ion channels, which are activated by changing the voltage acroos the membrane of a cell-based biosensor.

Competitive Antagonism

This type of antagonism refers to competition between agonists and antagonists at the same binding site on the receptor. Reversible competitive antagonism is characterized by a shift in the slope of a dose response curve to higher concentrations while maintaining the same maximum response and the slope of the curve. In irreversible competitive antagonism, no change in antagonist occupancy is observed when the cell is exposed to agonist.

Non-Competitive Antagonism

Non-competitive antagonism describes the situation where the antagonist blocks, at some point, the chain of events that leads to the production of a response by the agonist. In this type of antagonism, the agonist and antagonist either bind to different sites on the receptor/ion channel or the antagonists simply block the ion channel pore. The net effect is to reduce the slope and maximum of the agonist's dose-response curve.

Isosteric Inhibition

This type of antagonism refers to the self-inhibition of agonists above a certain concentrations; that is, an agonist will start to antagonize its own action at a sufficiently high concentration. A bell-shaped dose-response curve often signals the presence of this kind of antagonism.

Detection of Modulators of Presynaptically Expressed Ion-Channels

In another aspect, the system is used to detect a modulator of a presynaptically expressed ion channel. Strategies for studying presynaptically localized ion-channels often include patch clamp recordings of synaptosomes (i.e., pinched-off nerve terminals produced by homogenizing brain tissue) inserted in proteoliposomes or planar phospholipid bilayers (see, as described in Farley and Rudy, 1988, *Biophys. J.* 53: 919-934; Hirashima and Kirino, 1988, *Biochim Biophys Acta* 946: 209-214, for example). The method of Hirashima and Kirino, 1988, supra, is particularly preferred, as it is a simple and rapid technique for generating giant proteoliposomes comprising presynaptically expressed ion-channels which can be used as biosensors for electropysiological analysis in the system according to the invention.

Detection of Ligands Acting on Orphan Receptors/Ion-Channels

Conventional drug discovery approaches often are initiated by the discovery of ligand's biological activity which is subsequently used to characterize its tissue pharmacology and physiological role. Typically, after the ligand is characterized, the corresponding receptor is identified as target for drug screening in HTS applications. A relatively novel strategy for characterizing orphan receptors (i.e., receptors with an undefined biological activity) is often referred to as a "reverse pharmacology" approach. The reverse approach starts with an orphan receptor of unknown function that is used as target for detection of its ligand. The ligand is then used to explore the biological and pathophysiological role of the receptor. High-throughput screening is initiated on the receptor at the same time that the ligand is being biologically characterized in order to develop antagonists that will help determine the therapeutic value of the receptor.

The present invention is particularly useful for a reverse pharmacological approach. In one aspect, the system comprises a cell-based biosensor which is a non-native cell line which expresses an exogenous orphan receptor (e.g., such as an ion channel). Suitable native cell lines, include, but are not limited to, HEK-293, CHO-KI, and COS-7. There are several benefits coupled to screening ion channels in a non-native cell background. First, a transfected cell line containing a null background (e.g., which does not ordinarily express the orphan receptor) allows one to be certain of the molecular identity of the gene responsible for the observed signal. Second, the orphan receptor can be over-expressed, thus improving the signal-to-noise of the screening read-out. Third, host cells with low background conductances can be chosen to allow very sensitive assays of certain types of ion channels. Finally, these cell lines are relatively easy to culture and are robust enough to be handled by automated screening systems.

Detection of Modulators of Neurotransmitter Vesicular Release

Patch-clamp techniques to measure membrane capacitance, developed over ten years ago (see, e.g., Neher and Marty, 1982, *Proc. Natl. Acad. Sci. USA* 79: 6712-6716), provide a powerful tool to study the underlying mechanism and control of exocytosis.

The surface area of a cell depends on the balance between exocytosis and endocytosis. Exocytosis results in the discharge of vesicle contents (i.e., such as neurotransmitters) into the extracellular space and the incorporation of vesicle membrane into the plasma membrane, leading to an increase in cell surface area. During endocytosis, parts of the plasma membrane are retrieved, resulting in a decrease in the surface area. Changes in net exocytotic and endocytotic activity thus can be monitored by measuring changes in cell surface area.

Membrane capacitance is an electrical parameter of the cell that is proportional to the plasma membrane area. Thus, providing the specific capacitance remains constant, changes in plasma membrane area resulting from drug-induced modulation of exocytotic and endocytotic activity through presynaptically located ion-channels, can be monitored by electrophysiological recordings of membrane capacitance in the open measurement chamber of the system.

Determining Permeability Properties of a Cell

When a cell used in a screening procedure expresses a broad range of ion-channel types, characterizing the ion permeability properties of the cell's activated ion-channels can be used to characterize a drug's interaction with the cell. Information about permeability properties of an ion-channel can be determined by monitoring reversal potential which can be determined by evaluating current-to-voltage relationships, created from measurements of agonist-evoked currents at different holding potentials. By employing the reversal potential and knowledge about intra- and extra-cellular ion concentrations, the relative ion-channel permeability properties are determined from different models.

EXAMPLES

The invention will now be further illustrated with reference to the following examples. It will be appreciated that what follows is by way of example only and that modifications to detail may be made while still falling within the scope of the invention.

Example 1

Intracellular Recording of Ion Channel Activity

Traditionally, intracellular recordings are used in brain slice preparations. In this technique, the tip resistance varies normally between 50-150 MΩ. The electrode is lowered in the bath solution above the submerged slice which is fixed between two nylon nets. The resistance of the electrode is slightly increased when the tip reaches the surface of a cell in the slice. When the electrode penetrates (see below) the cell a negative deflection of the cell's membrane potential is registered. The seal between the electrode and the cell membrane is greatly improved by injection of a hyperpolarizating current into the cell. When a proper seal is formed, the penetrated cell should maintain a physiological relevant membrane potential without injection of the hyperpolarizating current.

The intracellular voltage-clamp technique works best with large transmembrane currents (>5 nA), leading to a concern that the error due to the uncompensated series resistance might be significant. If the sampling rate is correctly chosen and the capacitance compensation correctly set, there is no error due to series resistance. For small currents, the intracellular voltage clamp is less attractive because of noisier signals.

Bridge Balance: In intracellular recordings, the intracellular potential cannot be measured if the current injected to the micropipette is a variable waveform (e.g. a pulse). The variable current waveform causes a corresponding voltage drop across the micropipette. This causes problem when the intracellular potential is to be estimated. However, a special compensation circuitry can be used to eliminate the micropipette voltage drop from the recording of the membrane potential. The essence of the technique is to generate a signal that is proportional to the product of the micropipette current and the micropipette resistance. This signal is then subtracted from the amplifier output. This subtraction technique is commonly known as "Bridge Balance" because in the early days of micropipette recording, a resistive circuit, a "Wheatstone Bridge" was used to achieve the subtraction. In all modern micropipette amplifiers, operational amplifier circuits are used to perform the subtraction.

The electrode devices and electrode arrays according to the invention are inserted into cells using either mechanical force (stab injection), as illustrated in FIGS. 5A-C, or preferably by using a microelectroinjection protocol as illustrated in FIGS. 5D-E. See, e.g., as described in WO 02/330,066. Preferably, electrodes are inserted into surface-adherent cells. FIG. 6 shows an example where an array of nanoelectrodes are inserted into a plurality of adherent cells. Alternatively the method can be used on suspension cell transiently arrested in holding pipettes, as illustrated in FIGS. 7A-B, or in wells or orifices created on the surface of a substrate, or by using porous substrates (see, e.g., FIG. 7C). Cells can be trapped in these structures using hydrodynamic focusing (focusing with flows), optical trapping, or trapping by electrical fields. All above described electrode types can be used in array setups.

Example 2

Fabrication of Electrode Devices

A number of methods exist to microfabricate protruded cell contact surfaces having suitable geometries for carrying out electrophysiological measurements. Here, one particular procedure is described, by which a circular opening at the tip of a pyramidal structure in a cell chamber is microfabricated.

Masks for photolithography were produced using standard e-beam writing on a JEOL JBX-5DII electron beam lithography system (medium reflective 4" chrome masks and Shipley UV5 resists, 50 keV acc. voltage, dose 15 $\mu C/cm^{-2}$, exposure current 5 nA). The resist was spin coated at 2000 rpm for 60 s giving 250 nm of resist and soft baked for 10 minutes at 130° C. on a hotplate before exposure. The pattern was post exposure baked for 20 minutes in an oven at 130° C. and developed for 60 s in Shipley MF24-A, rinsed in DI water and ashed in a reactive ion etcher (Plasmatherm RIE m-95, 30 s, 50 W, 250 mTorr, 10 ccm $O_2$). The chrome was etched for 1-2 minutes in Balzers' chrome etch #4. The mask was stripped of the remaining resist using Shipley 1165 remover and rinsed in acetone, isopropanol and DI water. A 3", [100], low N-doped Silicon wafers polished on two sides with 700 nm of thermally grown silicon dioxide and a total thickness of 380 μm were cleaned in a reactive ion etcher (Plasmatherm RIE m-95 (30 s, 50 W, 250 mTorr, 10 ccm $O_2$)), spin coated with Shipley S-1813 photoresist at 4000 rpm, giving 1.3 μm of resist, and exposed through mask No. 1 for a dose of 110 $mJ/cm^{-2}$ at 400 nm wavelength on a Carl Süss MA6 mask aligner. The unit cell of pattern No. 1 consisted of 450-500 μm squares, where the quality and thickness of the wafer determined size of the square (see, e.g., FIG. 4A).

The wafer was developed for 45 s in Shipley MF319, rinsed in DI water, and ashed in a reactive ion etcher (Plasmatherm RIE m-95, 30 s, 50 W, 250 mTorr, 10 ccm $O_2$). The wafer was finally hard baked for 10 minutes at 130° C. The other side of the wafer was coated with S-1813 resist in the same manner and immediately hard baked for 10 minutes at 130° C. The silicon dioxide was etched with SioTech buffered oxide etch for 12-14 minutes rinsed in DI water. The wafer was stripped of the remaining resist with acetone, rinsed in isopropanol and DI water (FIG. 4B). The wafer was immersed in a bath of anisotropic enchant (an aqueous solution of 25% tetramethylammonium hydroxide) and etched for approximately 9.5 hours at 90° C. (FIG. 4C). The etching rate was typically 0.65 $\mu m \times min^{-1}$ and the anisotropy 40:1. The wafers was stripped of the remaining Silicon dioxide and immersed in RCA-1 (a 1:1:5 mixture of $NH_3:H_2O_2:H_2O$ at 75° C.) for 10 minutes, in 2% HF for 10 minutes, and in RCA-2 (a 1:1:5 mixture of $HCl:H_2O_2:H_2O$ at 80° C.) for 10 minutes.

The wafer was finally rinsed with DI water in a combined rinse- and dryer. The wafer was oxidized thermally at 1050° C. for 25 minutes yielding about 300 nm of Silicon dioxide (FIG. 4E). The unpatterned side of the wafer was spin coated with Shipley S-1813 photoresist at 4000 rpm, giving 1.3 μm of resist, and exposed through mask No. 2 (the unit cell of pattern No. 2 consisted in a 1 μm circle) for a dose of 110 $mJ/cm^{-2}$ at 400 nm wavelength on a Carl Süss MA6 mask aligner. The wafer was developed for 45 s in Shipley MF319 rinsed in DI water and ashed in a reactive ion etcher (Plasmatherm RIE m-95, 30 s, 50 W, 250 mTorr, 10 ccm $O_2$). The Silicon dioxide was etched in the same system (Plasmatherm RIE m-95, 15 minutes, 100 W, 100 mTorr, 32 ccm $CF_4$, 8 ccm $H_2$, 1 ccm $O_2$). The exposed Silicon was etched in a STS Multiplex deep reactive ion etcher using $SF_6$ as etching gas and $C_4F_8$ as passivation gas operating at 800 W of RF power, at a constant APC angle of 68% and the etching time was 7 s with an overrun time of 0.5 s, and the passivation time 4 s with an overrun time of 1 second. The pattern was etched until it reached the pyramidal Silicon dioxide structure buried in the Silicon. The exposed Silicon dioxide in the bottom of the aperture was etched a reactive ion etcher (Plasmatherm RIE m-95, 30 minutes, 100 W, 100 mTorr, 32 ccm $CF_4$, 8 ccm $H_2$, 1 ccm $O_2$) producing an aperture in the top of the pyramidal structure.

The wafer was once again exposed, this time through mask No. 3 (the unit cell of pattern No. 3 consisted in a 50 μm circle), for a dose of 110 $mJ/cm^{-2}$ at 400 nm wavelength on a Carl Süss MA6 mask aligner. The wafer was developed for 45 seconds wavelength on a Carl Süss MA6 mask aligner. The wafer was developed for 45 seconds in Shipley MF319, rinsed in DI water, and ashed in a reactive ion etcher (Plasmatherm RIE m-95, 30 s, 50 W, 250 mTorr, 10 ccm $O_2$) (FIG. 4I). The Silicon dioxide was etched in the same system (Plasmatherm RIE m-95, 15 minutes, 100 W, 100 mTorr, 32 ccm $CF_4$, 8 ccm $H_2$, 1 ccm $O_2$). The structure was finally released by etching away the silicon around it in a STS Multiplex deep reactive ion etcher using $SF_6$ as etching gas and $C_4F_8$ as passivation gas operating at 800 W of RF power, at a constant APC angle of 68% and the etching time was 7 seconds with an overrun time of 0.5 seconds, and the passivation time 4 seconds with an overrun time of 1 seconds.

The pattern was etched until 5-10 μm of the structure was visible. The wafer was stripped of the remaining resist with acetone, rinsed in isopropanol and DI water and ashed in a reactive ion etcher (Plasmatherm RIE m-95, 30 s, 50 W, 250 mTorr, 10 ccm $O_2$).

Variations, modifications, and other implementations of what is described herein will occur to those of ordinary skill in the art without departing from the spirit and scope of the invention as claimed herein.

All of the references, patents, patent publications, and international applications, cited herein are incorporated by reference herein in their entireties.

What is claimed is:

1. A microfluidic system comprising:
  a) at least one measurement chamber wherein the measurement chamber comprises walls and a base;
  b) at least one hollow nanotip protruding from the walls or base of the measurement chamber and having an aperture at an end of the nanotip; and
  c) at least one microchannel connected to the measurement chamber, the microchannel having at least one inlet positioned to receive an aqueous solution and at least one outlet positioned to deliver the aqueous solution into the measurement chamber.

2. The microfluidic system of claim 1, wherein at least one of the measurement chambers is circular.

3. The microfluidic system of claim 1, wherein the nanotip lumen comprises a conducting medium.

4. The microfluidic system of claim 3, wherein the conducting medium is a liquid conducting medium.

5. The microfluidic system of claim 4, wherein the liquid conducting medium comprises an electrolyte solution, or an electrically conducting polymer.

6. A microfluidic system comprising:
  a) at least one measurement chamber comprising walls and a base;
  b) a plurality of electrode tips wherein the electrode tips protrude from the walls or base of the measurement chamber; and
  c) at least one microchannel connected to the measurement chamber, wherein the microchannel comprises at least one inlet positioned to receive an aqueous solution and at least one outlet positioned to deliver the aqueous solution into the measurement chamber.

7. The system of claim 1 or 6, wherein the at least one tip is tapered to facilitate insertion into a cell or cell structure.

8. The system of claim 1 or 6, wherein at least one tip comprises a contacting surface for contacting biological molecules or macromolecules and wherein the contacting surface comprises a hydrophilic material.

9. The system of claim 8, wherein the at least one contacting surface has a diameter of less than 5 μm.

10. The system of claim 8, wherein the at least one contacting surface has a diameter of less than 1 μm.

11. The system of claim 1 or 6, further comprising a pressure control device connected to the at least one microchannel, for controlling positive and negative fluid pressure in the at least one microchannel.

12. The system of claim 1 or 6, wherein the microchannel in the microfluidic system is connected to a multiwell plate through one or more external tubings or capillaries.

13. The system of claim 1 or 6, further comprising an amplifier connected to the at least one nanotip electrode.

14. The system of claim 1 or 6, further comprising a plurality of buffer delivery and agonist delivery channels, each channel comprising an outlet for delivering a substantially separate aqueous stream into the chamber.

15. The system of claim 1 or 6, wherein at least one microchannel delivers at least one agent into the measurement chamber.

16. The system of claim 1, wherein the at least one tip protrudes extends from a substantially planar portion of the measurement chamber.

17. The system of claim 6, wherein the plurality of tips protrude from a substantially planar portion of the measurement chamber.

* * * * *